(12) United States Patent
Thoma

(10) Patent No.: US 6,589,530 B1
(45) Date of Patent: *Jul. 8, 2003

(54) HEPATITIS B SURFACE ANTIGEN VACCINE

(75) Inventor: Hans A. Thoma, München (DE)

(73) Assignee: Medeva Holdings B.V., Amsterdam (NL)

(*) Notice: Subject to any disclaimer, the term of this patent is extended or adjusted under 35 U.S.C. 154(b) by 0 days.

This patent is subject to a terminal disclaimer.

(21) Appl. No.: 08/480,757

(22) Filed: Jun. 7, 1995

Related U.S. Application Data

(62) Division of application No. 08/258,549, filed on Jun. 10, 1994, now Pat. No. 6,022,543, which is a continuation of application No. 07/340,172, filed on Feb. 21, 1989, now abandoned.

(30) Foreign Application Priority Data

Jun. 22, 1987 (EP) ............................................ 87108914
Jun. 22, 1987 (EP) ............................................ 87108915

(51) Int. Cl.⁷ ............................ A61K 39/29; C07K 1/00
(52) U.S. Cl. ................................ 424/189.1; 424/227.1; 435/69.1; 435/69.3; 530/350; 536/23.72
(58) Field of Search ........................... 435/69.1, 69.3; 424/189.1, 227.1; 530/350; 536/23.72

(56) References Cited

U.S. PATENT DOCUMENTS

| | | |
|---|---|---|
| 3,636,191 A | 1/1972 | Blumberg et al. ........ 424/227.1 |
| 4,415,491 A | 11/1983 | Vyas ........................... 530/327 |
| 4,428,941 A | 1/1984 | Galibert et al. ................. 514/2 |
| 4,563,423 A | 1/1986 | Murray et al. ............. 435/69.3 |
| 4,599,230 A | 7/1986 | Milich et al. ............. 424/189.1 |
| 4,599,231 A | 7/1986 | Milich et al. ............. 424/189.1 |
| 4,639,371 A | 1/1987 | Prince et al. ............. 424/227.1 |
| 4,649,192 A | 3/1987 | Van Wijnendaele et al. ........................... 530/371 |
| 4,683,136 A | 7/1987 | Milich et al. .......... 424/189.11 |
| 4,696,898 A | 9/1987 | Fitts et al. ................. 435/69.3 |
| 4,710,463 A | 12/1987 | Murray .................... 435/172.3 |
| 4,722,840 A | 2/1988 | Valenzuela et al. ...... 424/192.1 |
| 4,741,901 A | 5/1988 | Levinson et al. ........ 435/172.3 |
| 4,742,158 A | 5/1988 | Lehman et al. ............. 530/371 |
| 4,758,507 A | 7/1988 | Murray et al. .................. 435/5 |
| 4,777,240 A | 10/1988 | Moriarty et al. ............ 530/326 |
| 4,816,564 A | 3/1989 | Ellis et al. .................. 530/350 |
| 4,818,527 A | 4/1989 | Thornton et al. ........ 424/189.1 |
| 4,847,080 A | 7/1989 | Neurath et al. ............. 530/324 |
| 4,861,588 A | 8/1989 | Neurath et al. ............. 530/324 |
| 4,882,145 A | 11/1989 | Thornton et al. ........ 424/189.1 |
| 4,883,865 A | 11/1989 | Kubek ........................ 530/415 |
| 4,895,800 A | 1/1990 | Tschopp et al. ........... 435/69.3 |
| 4,935,235 A | 6/1990 | Rutter et al. ............. 424/189.1 |
| 4,942,125 A | 7/1990 | Moriarty .................... 435/7.92 |
| 4,945,046 A | 7/1990 | Horii et al. ................ 435/69.3 |
| 4,959,323 A | 9/1990 | Acs et al. ............... 435/252.33 |
| 4,963,483 A | 10/1990 | Ellis et al. ................. 435/69.1 |
| 4,977,092 A | 12/1990 | Bitter ....................... 435/320.1 |
| 5,011,915 A | 4/1991 | Yamazaki .................... 530/414 |
| 5,024,938 A | 6/1991 | Nozaki et al. ............. 435/68.1 |
| 5,039,522 A | 8/1991 | Neurath .................... 424/194.1 |
| 5,068,185 A | 11/1991 | Hopper et al. ............. 435/69.1 |
| 5,098,704 A | 3/1992 | Valenzuela ................ 424/227.1 |
| 5,102,989 A | 4/1992 | Sitrin et al. .................. 530/371 |
| 5,133,961 A | 7/1992 | Ellis et al. ............... 424/189.1 |
| 5,143,726 A | 9/1992 | Thornton et al. ........ 424/189.1 |
| 5,158,769 A | 10/1992 | Neurath et al. .......... 424/189.1 |
| 5,196,194 A | 3/1993 | Rutter et al. ............. 424/189.1 |
| 5,198,348 A | 3/1993 | Bitter ........................ 435/69.1 |
| 5,204,096 A | 4/1993 | Neurath et al. .......... 424/189.1 |
| 5,242,812 A | 9/1993 | Even-Chen ................ 435/70.3 |
| 5,314,808 A | 5/1994 | Tiollais et al. ............. 435/69.3 |
| 5,324,513 A | 6/1994 | Sobczak et al. ........... 435/69.3 |
| 5,436,139 A | 7/1995 | Rutter et al. .............. 435/69.3 |
| 5,462,863 A | 10/1995 | Hsieh et al. ............... 435/69.3 |
| 5,565,548 A | 10/1996 | Neurath et al. ............. 530/524 |
| 5,591,638 A | 1/1997 | Tiollais et al. ........... 435/320.1 |
| 5,620,844 A | 4/1997 | Neurath et al. ................. 435/5 |
| 5,792,463 A | 8/1998 | Valenzuela et al. ...... 424/202.1 |
| 5,837,249 A | 11/1998 | Heber-Katz et al. ..... 424/186.1 |
| 6,022,543 A | * 2/2000 | Thoma .................... 424/189.1 |
| 6,072,049 A | * 6/2000 | Thoma .................... 536/23.72 |
| 6,100,065 A | * 8/2000 | Thoma ...................... 435/69.3 |
| 6,110,706 A | * 8/2000 | Thoma ...................... 435/69.3 |
| 6,117,653 A | * 9/2000 | Thoma ...................... 435/69.3 |

FOREIGN PATENT DOCUMENTS

| | | |
|---|---|---|
| AU | 1093088 | 8/1988 |
| CN | 1094311 A | 11/1994 |
| CN | 1108306 A | 9/1995 |
| CN | 1109784 A | 10/1995 |
| EP | 0013828 | 8/1980 |
| EP | 0020251 | 12/1980 |

(List continued on next page.)

OTHER PUBLICATIONS

P. Winckur et al., "The Hepatitis A Virus Polyprotein Expressed by a Recombinant Vaccinia Virus Undergoes Protcolytic Processing and Assembly into Virus–like Particles", Journal of Virulogy, vol. 65, pp. 5029–5036. (1991).

(List continued on next page.)

Primary Examiner—Mary K. Zeman
(74) Attorney, Agent, or Firm—Popovich & Wiles, P.A.

(57) ABSTRACT

HBV surface antigen particles, prepared by recombinant DNA technology are described, said particles being composed of epitopes from the group of surface peptides and/or core peptide of non-A, non-B hepatitis virus, hepatitis A virus, or hepatitis virus B. Respective particles are especially characterized by a composition of different epitopes selected from pre-S and S peptides. There are also described DNA-sequences, plasmids, and cell lines coding for respective HBV surface antigen particles as well as a new vaccine containing the same.

16 Claims, 38 Drawing Sheets

FOREIGN PATENT DOCUMENTS

| | | |
|---|---|---|
| EP | 0 044 710 A1 | 1/1982 |
| EP | 0 072 318 B1 | 2/1983 |
| EP | 0 120 551 B1 | 10/1984 |
| EP | 0 154 902 B1 | 9/1985 |
| EP | 0154902 | 9/1985 |
| EP | 0155146 | 9/1985 |
| EP | 0155198 | 9/1985 |
| EP | 0156712 | 10/1985 |
| EP | 0 171 908 A2 | 2/1986 |
| EP | 0 174 759 A1 | 3/1986 |
| EP | 0175261 | 3/1986 |
| EP | 0180012 | 5/1986 |
| EP | 0 182 442 B2 | 5/1986 |
| EP | 0198474 | 10/1986 |
| EP | 0 199 480 A2 | 10/1986 |
| EP | 0 201 416 B1 | 11/1986 |
| EP | 0 218 474 A2 | 4/1987 |
| EP | 0243913 | 11/1987 |
| EP | 0244924 | 11/1987 |
| EP | 0 248 410 A2 | 12/1987 |
| EP | 0250253 | 12/1987 |
| EP | 0251460 | 1/1988 |
| EP | 0257507 | 3/1988 |
| EP | 0271302 | 6/1988 |
| EP | 0 278 940 A2 | 8/1988 |
| EP | 0 299 242 A2 | 1/1989 |
| EP | 0 300 213 A1 | 1/1989 |
| EP | 0304578 | 3/1989 |
| EP | 0 339 567 A1 | 11/1989 |
| EP | 0 344 864 A2 | 12/1989 |
| EP | 0 344 864 A3 | 9/1990 |
| EP | 0385610 | 9/1990 |
| EP | 0 414 374 A2 | 2/1991 |
| EP | 0 421 626 A1 | 4/1991 |
| EP | 0 448 126 A1 | 9/1991 |
| EP | 0 491 077 A1 | 6/1992 |
| EP | 0 511 854 A1 | 11/1992 |
| EP | 0 511 855 A1 | 11/1992 |
| EP | 0 563 093 B1 | 8/1998 |
| JP | 58194897 A | 11/1983 |
| JP | 59074985 A | 4/1984 |
| JP | 59080615 A | 5/1984 |
| WO | 8301783 | 5/1983 |
| WO | 8402534 | 7/1984 |
| WO | WO 86/05189 | 9/1986 |
| WO | 8810300 | 12/1988 |
| WO | WO 92/11368 | 7/1992 |

OTHER PUBLICATIONS

A.R. Neurath et al., "Hepatitis B Virus Surface Antigen (HBsAg) as Carrier for Synthetic Peptides Having an Attached Hydrophobic Tail", Molecular Immunology, vol. 26, pp. 53–62. (1989).

B.E. Clarke et al., "Improved Immunogenicity of a Peptide Epitope After Fusion to Hepatitis B Core Protein", Nature, vol. 330, pp. 381–384. (1987).

D.R. Milich et al., "A Single 10–Residue Pre–S(1) Peptide Can Prim T Cell Help for Antibody Production to Multiple Epitopes Within the Pre–S(1), Pre–S(2), and S Regions of HBsAg[1]", The Journal of Immunology, vol. 138, pp. 4457–4465. (1987).

P. Valenzuela et al., "Synthesis and Assembly in Yeast of Hepatitis B Surface Antigen Particles Containing the Poly–albumin Receptor", Bio/Technology, vol. 3, pp. 317–320. (1985).

K. Cheng et al., "Hepatitis B Virus Large Surface Protein is Not Secreted but is Immunogenic When Selectively Expressed by Recombinant Vaccinia Virus", Journal of Virology, vol. 60, pp. 337–344. (1986).

D. Standring et al., "Assembly of Viral Particles in Xenopus Oocytes: Pre–Surface–Antigens Regulate Secretion of the Hepatitis B Viral Surface Envelope Particle", Proc. Natl. Acad. Sci. USA, vol. 83, pp. 9338–9342. (1986).

A. Neurath et al., "Location and Chemical Synthesis of a Pre–S Gene Coded Immunodominant Epitope of Hepatitis B Virus", Science, vol. 224, pp. 392–395. (1984).

D. Persing et al., "A Frameshift Mutation in the pre–S Region of the Human Hepatitis B Virus Genome Allows Production of Surface Antigen Particles but Eliminates Binding to Polymerized Albumin", Proc. Natl. Acad. Sci. USA, vol. 82, pp. 3440–3444. (1985).

M. Michel et al., "Synthesis in Animal Cells of Hepatitis B Surface Antigen Particles Carrying a Receptor for Polymerized Human Serum Albumin", Proc. Natl. Acad. Sci. USA, vol. 81, pp. 7708–7712. (1984).

A. Neurath et al., "Hepatitis B Virus Contains pre–S Gene–Encoded Domains", Nature, vol. 315, pp. 154–156. (1985).

V. Bruss and R. Thomssen, "Mapping a Region of the Large Envelope Protein Required for Hepatitis B Virion Maturation," Journal of Virology, vol. 68, No. 3, pp. 1643–1650 (1994).

Carloni et al., "A Transformed Vero Cell Line Stably Producing the Hepatitis B Virus Surface Antigen," Gene, vol. 31, pp. 49–57 (1984).

Delpeyroux, "A Poliovirus Neutralization Epitope Expressed on Hybrid Hepatitis B Surface Antigen Particles," Science, vol. 233, pp. 472–475 (1986).

Fritsch et al., "Virologie," C.R Academy of Sciences, pp. 1453–1456 (1978) (English abstract).

F. Galibert et al., "Nucleotide Sequence of the Hepatitis B Virus Genome (Subtype ayw) Cloned in *E. coli*," Nature, vol. 281, pp. 646–650 (1979).

W. H. Gerlich and V. Bruss, "Functions of Hepatitis B Virus Proteins and Molecular Targets for Protective Immunity," in *Hepatitis B Vaccines in Clinical Practice*, R. W. Ellis, ed., Marcel Dekker, Inc., pp. 41–82 (1993).

Hsiung et al., "Efficient Production of Hepatitis B Surface Antigen Using a Bovine Papilloma Virus–Metallothionein Vector," Journal of Molecular and Applied Genetics, vol. 2, pp. 497–506 (1984).

E. Jacobs et al., "Hepatitis B Recombinant Vaccines," Biotech International, pp. 349–354 (Jul. 1991).

W. N. Katkov et al., "Immunogenicity of a 'pre–S2 plus S' Hepatitis B Vaccine in Healthy Adults," Journal of Viral Hepatitis, vol. 1, pp. 79–83 (1994).

LeClerc et al., "A Synthetic Vaccine Constructed by Copolymerization of B and T Cell Determinants," European Journal of Immunology, vol. 17, pp. 269–273 (1987).

O. Marquardt et al., "Cell–Type Dependent Expression and Secretion of Hepatitis B Virus pre–S1 Surface Antigen," Postgraduate Medical Journal, vol. 63, Supp. 2, pp. 41–50 (1987).

W. J. McAleer et al., "Human Hepatitis B Vaccine from Recombinant Yeast," Nature, vol. 307, pp. 178–180 (1984).

Milich et al., "Immune Response to Hepatitis B Virus Core Antigen (HBcAg): Localization of T Cell Recognition Sites within HBcAg/HBeAg," Journal of Immunology, vol. 139, pp. 1223–1231 (1987).

Milich et al., "Nonoverlapping T and B Cell Determinants on an Hepatitis B Surface Antigen Pre–S(2) Region Synthetic Peptide," J. of Exp. Med., vol. 164, pp. 532–547 (1986).

Milich et al., "T Cell and B Cell Recognition of Native and Synthetic Pre–S Region Determinants on Hepatitis B Surface Agent," Vaccines, vol. 86, pp. 377–382 (1986).

Milich et al., "Two Distinct But Overlapping Anitbody Binding Sites in the Pre–S(2) Region of HBsAg Localized Within 11 Continuous Residues," Journal of Immunology, vol. 137, pp. 2703–2710 (1986).

Milich et al., Enhanced Immunogenicity of the Pre–S Region of Hepatitis B Surface Antigen, Science, vol. 228, 1195–1199 (1985).

E. Miskovsky et al., "Comparative Safety and Immunogenicity of Yeast Recombinant Hepatitis B Vaccines Containing S and pre–S2+S Antigens," Vaccine, vol. 9, pp. 346–350 (1991).

Okamoto et al., "Nucleotide Sequence of a Cloned Hepatitis B Virus Genome, Subtype ayr: Comparison with Genomes of the Other Three Subtypes," Journal of General Virology, vol. 67, pp. 2305–2314 (1986).

Y. Ono et al., "The Complete Nucleotide Sequences of the Cloned Hepatitis B Virus DNA; Subtype adr and adw," Nucleic Acids Research, vol. 11, pp. 1747–1757 (1983).

Pavlakis et al., "Regulation of a Metallothionein–Growth Hormone Hybrid Gene in Bovine Papilloma Virus," Proc. Natl. Acad. Sci. USA, vol. 80, pp. 397–401 (1983).

D. H. Persing et al., "Inhibition of Secretion of Hepatitis B Surface Antigen by a Related Presurface Polypeptide," Science, vol. 234, pp. 1388–1391 (1986).

J. Pêtre et al., "Development of Hepatitis B Vaccine from Transformed Yeast Cells," Postgraduate Medical Journal, vol. 63, Supp. 2, pp. 73–81 (1987).

J. Pillot et al., "Weak Immunogenicty of the PreS2 Sequence and Lack of Circumventing Effect on the Unresponsiveness to the Hepatitis B Virus Vaccine," Vaccine, vol. 13, No. 3, pp. 289–294 (1995).

Rutgers et al., "Potential Future Recombinant Vaccines," in Hepatitis B Vaccines in Clinical Practice, R. W. Ellis, ed., Marcel Dekker, Inc., pp. 383–407 (1993).

P. Valenzuela et al., "Nucleotide Sequence of the Gene Coding for the Major Protein of Hepatitis B Virus Surface Antigen," Nature, vol. 280, pp. 815–819 (1979).

Adams et al., "The Expression of Hybrid HIV:TY Virus–like Particles in Yeast," Nature, 329:68–70 (Sep. 3, 1987).

Bruss et al., "Functions of the Internal Pre–S Domain of the Large Surface Protein in Hepatitis B Virus Particle Morphogenesis," Journal of Virology, 69(11):6652–6657 (1995).

Deepen et al., "Assay of PreS Epitopes and PreS1 Antibody in Hepatitis B Virus Carriers and Immune Persons," Med. Microbiol. Immunol., 179:49–60 (1990).

Dehoux et al., "Expression of the Hepatitis B Virus Large Envelope Protein in Saccharomyces Cerevisiae," Gene, 48:155–163 (1986).

Delpeyroux et al., "Insertions in the Hepatitis B Surface Antigen Effect on Assembly and Secretion of 22–nm Particles from Mammalian Cells," J. Mol. Biol., 195:343–350 (1987).

Delpeyroux et al., "Presentation and Immunogenicity of the Hepatitis B Surface Antigen and a Poliovirus Neutralization Antigen on Mixed Empty Envelope Particles," Journal of Virology, 62(5):1836–1839 (May 1988).

Dyson et al., "Selection of Peptide Inhibitors of Interactions Involved in Complex Protein Assemblies: Association of the Core and Surface Antigens of Hepatitis B Virus," Proc. Natl. Acad. Sci. USA, 92:2194–2198 (Mar. 1995).

Feitelson et al., "The Nature of Polypeptides Larger in Size than the Major Surface Antigen Components of Hepatitis B and Like Viruses in Ground Squirrels, Woodchucks, and Ducks," Virology, 130:76–90 (1983).

Francis et al., "Peptides with Added T–Cell Epitopes can Overcome Genetic Restriction of the Immune Response," CSH, pp. 9–13 (Sep. 1987) (abstract only).

Gallina et al., "A C–Terminal PreS1 Sequence is Sufficient to Retain Hepatitis B Virus L Protein in 293 Cells," Virology, 213:57–69 (1995).

Ganem et al., "The Molecular Biology of the Hepatitis B Viruses," Ann. Rev. Biochem., 56:651–693 (1987).

Good et al., "Construction of Synthetic Immunogen: Use of New T–Helper Epitope on Malaria Circumsporozite Protein," Science, 235:1059–1062 (Feb. 27, 1987).

Heermann et al., "Large Surface Proteins of Hepatitis B Virus Containing the Pre–S Sequence," Journal of Virology, 52(2):396–402 (Nov. 1984).

Heermann et al., "Immunogenicity of the Gene S and Pre–S Domains in Hepatitis B Virions and HBsAg Filaments," Intervirology, 28:14–25 (1987).

Lo et al., "Characterization of Restriction Endonuclease Maps of Hepatitis B Viral DNAs," Biochemical and Biophysical Research Communications, 129(3):797–803 (Jun. 28, 1985).

Machein et al., "Deletion and Insertion Mutants of HBsAg Particles," Arch. Virology, 4:133–136 (1992).

Najarian et al., "Primary Structure and Gene Organization of Human Hepatitis A Virus," Proc. Nat'l. Acad. Sci., 82:2627–2631 (May 1985).

Neurath et al., "The Pre–S Region of Hepadnavirus Envelope Proteins," Academic Press, Inc., 34:65–142 (1988).

Persing et al., "The Pre S1 Protein of Hepatitis B Virus is Acylated at its Amino Terminus with Myristic Acid," Journal of Virology, pp. 1672–1677 (May 1987).

Pontisso et al., "Human Liver Plasma Membranes Contain Receptors for the Hepatitis B Virus Pre–S1 Region and, via Polymerized Human Serum Albumin, for the Pre–S2 Region," Journal of Virology, pp. 1981–1988 (May 1989).

Pontisso et al., "Identification of an Attachment Site for Human Liver Plasma Membranes on Hepatitis B Virus Particles," Virology, 173:522–530 (1989).

Prange et al., "Properties of Modified Hepatitis B Virus Surface Antigen Particles Carrying PreS Epitopes," Journal of General Virology, 76:2131–2140 (1995).

Stibbe et al., "Structural Relationships Between Minor and Major Proteins of Hepatitis B Surface Antigen," Journal of Virology, 46(2):626–628 (May 1983).

Summers et al., "Genome of Hepatitis B Virus: Restriction Enzyme Cleavage and Structure of DNA Extracted from Dane Particles," Proc. Nat. Acad. Sci. USA, 72(11):4597–4601 (Nov. 1975).

Valenzuela et al., "Antigen Engineering in Yeast: Synthesis and Assembly of Hybrid Hepatitis B Surface Antigen–herpes Simplex 1 gD Particles," Bio/Technology, 3:323–326 (Apr. 1985).

Valenzuela et al., "Synthesis and Assembly of Hepatitis B Virus Surface Antigen Particles in Yeast," Nature, 298:347–350 (Jul. 22, 1982).

Wampler et al., "Multiple Chemical Forms of Hepatitis B Surface Antigen Produced in Yeast," *Proc. Natl. Acad. Sci. USA*, 82:6830–6834 (Oct. 1985).

Waters et al., "A Study of the Antigenicity and Immunogenicity of a new Hepatitis B Vaccine Using a Panel of Monoclonal Antibodies," *DRAFT* (20 pages).

Wong et al., "Identification of Hepatitis B Virus Polypeptides Encoded by the Entire Pre–S Open Reading Frame," *Journal of Virology*, 55(1):223–231 (Jul. 1985).

Xu et al., "A Modified Hepatitis B Virus Surface Antigen with the Receptor–binding Site for Hepatocytes at its C Terminus: Expression, Antigenicity and Immunogenicity," *Journal of General Virology*, 75:3673–3677 (1994).

Zuckerman et al., "Immune Response to a New Hepatitis B Vaccine in Healthcare Workers who had not Responded to Standard Vaccine: Randomised Double Blind Dose–response Study," *BMJ*, 314:329–333 (Feb. 1, 1997).

Zuckerman et al., "Immunogenicity of a Novel Triple–S Hepatitis B Vaccine in Non–responder Healthcare Workers," *DRAFT* (22 pages).

*Press Release*, "Medeva PLC Announces New Positive Clinical Trial Results for Hepatitis B Product Hepagene as Vaccine and Treatment" (Oct. 16, 1997).

Dienstag et al., "Hepatitis B Vaccine Administered to Chronic Carriers of Hepatitis B Surface Antigen," *Annals of Internal Medicine*, 96(5):575–579 (1982).

Dusheiko et al., "Synthesis of Antibodies to Hepatitis B Virus by Cultured Lymphocytes from Chronic Hepatitis B Surface Antigen Carriers," *The Journal of Clinical Investigation*, 71:1104–1113 (May 1983).

Farci et al., "Lack of Protective Immunity Against Reinfection with Hepatitis C Virus," Science, 258:135–140 (Oct. 2, 1992).

Wilson et al., *Principles of Internal Medicine*, p. 1339 (1991).

Dubois et al., "Excretion of Hepatitis B Surface Antigen Particles from Mouse Cells Transformed with Cloned Viral DNA," *Proc. Natl. Acad. Sci. USA*, 77(8):4549–4553 (Aug. 1980).

Fattovich et al., "Cellular Immunity to the Hepatitis B Virion in Acute Hepatitis Type B," *Clin. Exp. Immunol.*, 53(3):645–650 (Sep. 1983).

Ganem, "Assembly of Hepadnaviral Virions and Subviral Particles," *Current Topics in Microbiol. Immunol.*, 168:61–83 (1991).

Gerfaux et al., Constituents of HBs Particle: Characterization and Purity of HBsAg In <<HEVAC B>>, *Developments in Biological Standardization*, 54:45–52 (1983).

Haubitz et al., "Clinical Experience with a new Recombinant Hepatitis–B Vaccine in Previous Non–responders with Chronic Renal Insufficiency," *Clinical Nephrology*, 45(3):180–182 (1996).

Kent et al., "Approaches to a Totally Synthetic Vaccine for Hepatitis B Virus Based on Determinants Coded by the Pre–S Gene", *Peptide Chemistry 1984*, N. Izumiya (ed.), Protein Research Foundation, Osaka, Japan, 1985, 22:167–170.

Laub et al., "Synthesis of Hepatitis B Surface Antigen in Mammalian Cells: Expression of the Entire Gene and the Coding Region," *J. Virol.*, 48(1):271–280 (Oct. 1983).

McDermott et al., "HLA Haplotypes in Non–responders to Hepatitis B Vaccine and in Response to a Novel Recombinant Vaccine".

"Application for a Clinical Trial Exemption for Hep B–3 Hepatitis B Vaccine (rDNA)," Medeva Scientific and Regulatory Affairs (Sep. 1994).

Mishiro et al., "A 49,000–Dalton Polypeptide Bearing all Antigenic Determinants and Full Immunogenicity of 22–nm Hepatitis B Surface Antigen Particles," *Journal of Immunology*, 124(4):1589–1593 (Apr. 1980).

Offensperger et al., "Expression in *Escherichia Coli* of a Cloned DNA Sequence Encoding the Pre–S2 Region of Hepatitis B Virus," *Proc. Natl. Acad. Sci. USA*, 82(22):7540–7544 (Nov. 1985).

Pfaff et al., "Characterization of Large Surface Proteins of Hepatitis B Virus by Antiibodies to PreS–S Encoded Amino Acids," *Virology*, 148(1):15–22 (Jan. 15, 1986).

Wagner et al., "Hepatitis B Vaccination of Immunosuppressed Heart Transplant Recipients with the Vaccine Hepa Gene 3 Containg Pre–S1, Pre–S2, and S Gene Products," *The Clinical Investigator*, 72(5):350–353 (May 1994).

Alberts et al., *Molecular Biology of the Cell*, second edition, Garland Publishing Inc., New York and London, pp. 172–173 (1989).

Atassi, "Antigenic Structures of Proteins," *Eur. J. Biochem.*, 145:1–20 (1984).

Atassi et al., "Localization, Synthesis, and Activity of an Antigenic Site on Influenza Virus Hemagglutinin," *Proc. Natl. Acad. Sci. USA*, 80:840–844 (1983).

Baron et al., "Antibodies Against a Synthetic Peptide of the Poliovirus Replicase Protein: Reaction with Native, Virus–Encoded Proteins and Inhibition of Virus–Specific Polymerase Activities In Vitro," *Journal of Virology*, 43(3):969–978 (Sep. 1982).

Bittle et al., "Protection Against Foot–and–Mouth Disease by Immunization with a Chemically Synthesized Peptide Predicted from the Viral Nucleotide Sequence," *Nature*, 298:30–33 (Jul. 1, 1982).

Burrell et al., "Expression in *Eschericia coli* of Hepatitis B Virus DNA Sequences Cloned in Plasmid pBR322," *Nature*, 279:43–47 (May 3, 1979).

Dreesman et al., "Antibody to Hepatitis B Surface Antigen after a Single Inoculation of Uncoupled Synthetic HBsAg Peptides," *Nature*, 295:158–160 (Jan. 14, 1982).

Emtage et al, "The Production of Vaccines by Recombinant DNA Techniques," *New Developments With Human and Veterinary Vaccines*, pp. 367–409 (1980).

Fritsch et al., "Virology–Cloning the Genome of the Hepatitis B Virus in *E. Coli,*" *C.R. Acad. Sci.*, Paris, 287:1453–1456 (Dec. 18, 1978).

Ganem, "Assembly of Hepadnaviral Virions and Subviral Particles," *Current Topics in Microbiology and Immunology*, 168:61–83 (1991).

Green et al., "Immunogenic Structure of the Influenza Virus Hemagglutinin," *Cell*, 28:477–487 (Mar. 1982).

Hemmerling et al., "Comparison of the Entire Pre–S Peptide Sequence to Selected Epitope Sequences in a New Hepatitis B Vaccine Development," *International Symposium on Progress in Hepatitis B Immunization* (May 3–5, 1989).

Hopp et al., "Prediction of Protein Antigenic Determinants from Amino Acid Sequences," *Proc. Natl. Acad. Sci. USA*, 78(6):3824–3828 (Jun. 1981).

Landers et al., "Structure of Hepatitis B Dane Particle DNA and Nature of the Endogenous DNA Polymerase Reaction," *Journal of Virology*, 23(2):368–376 (Aug. 1977).

Lenkei et al., "Receptors for Polymerized Albumin on Liver Cells," *Experientia*, 33:1046–1047 (1977).

Lerner et al., "Chemically Synthesized Peptides Predicted from the Nucleotide Sequence of the Hepatitis B Virus Genome Elicit Antibodies Reactive with the Native Envelope Protein of Dane Particles," *Proc. Natl. Acad. Sci. USA*, 78(6):3403–3407 (Jun. 1961).

Machida et al., "A Hepatitis B Surface Antigen Polypeptide (P31) with the Receptor for Polymerized Human as Well as Chimpanzee Albumins," *Gastroenterology*, 85:268–274 (1983).

Neurath et al., "Antibodies as Immunological Probes for Studying the Denaturation of HBsAg," *Journal of Medical Virology*, 6:309–322 (1980).

Neurath, "Chemical Synthesis of Hepatitis B Vaccine," *Recent Developments in Prophylactic Immunization*, vol. 12, Ed. Zuckermann, Kluwer Academic Publishers (1989).

Pasek et al., "Hepatitis B Virus Genes and their Expression in *E. Coli,*" *Nature*, 282:575–579 (Dec. 6, 1979).

Peterson et al., "Partial Amino Acid Sequence of Two Major Component Polypeptides of Hepatitis B Surface Antigen," *Proc. Natl. Acad. Sci. USA*, 74(4):1530–1534 (Apr. 1977).

Playfair, "Immune Intervention," *New Trends in Vaccines*, vol. 1, Ed. I. M. Roitt, Academic Press, London, 1984, pp. 4–7.

Poma et al., "The Superior Immunogenicity of a Pre–S1 Containing HBV Vaccine Compared to a S–Vaccine in Comparative Clinical Trials," *Pre–Print of Poster from the 1990 International Symposium on Viral Hepatitis and Liver Disease*.

Stibbe et al., "Characterization of Pre–S Gene Products in Hepatitis B Surface Antigen," *Developments in Biological Standardization*, 54:33–43 (1983).

Stibbe et al., "Structural Relationships Between Minor and Major Proteins of Hepatitis B Surface Antigen," *Journal of Virology*, 46:626–628 (1983).

Stibbe et al., "Variable Protein Composition of Hepatitis B Surface Antigen from Different Donors," *Virology*, 123:436–442 (1982).

Thoma et al., "Does the Pre–S2 Have the Same Effect in Improving the HBV Immune Response Compared to Pre–S1?", Pre–Print of Paper Presented at the 1990 International Symposium on Viral Hepatitis and Liver Disease, Apr. 1990 in Houston, Texas.

Thoma et al., "Evaluation of Immune Response in a Third Generation Hepatitis B Vaccine Containing Pre–S Proteins in Comparative Trials," *Progress in Hepatitis B Immunization*, 194:35–42 (1990).

Thoma et al., "Improvement of the Hepatitis–B Immune Response Through Pre–S Incorporation with Specific Respect to Elderly," Pre–Print of Poster from the 1990 International Symposium on Viral Hepatitis and Liver Disease.

Thoma et al., "Recombinant Hepatitis B Particles Containing Pre–S1 and Pre–S2 as a Third Generation Hepatitis B Vaccine," International Conference, *Current Trends in Chronically–Evolving Viral Hepatitis*, Oct. 5–8, 1988, Fiuggi, Italy.

Thoma et al., "Third Generation Hepatitis B Vaccine Based on Variable Recombinant Control of Amount of Pre–S, S, and Subtypes Secreted as Particles from Mammalian Cells," *Reprint of Presentation from the II International Symposium on Viral Hepatitis and Hepatocellular Carcinoma*, Dec. 1988, Taipei, Taiwan.

Tiollais et al, "Biology of Hepatitis B Virus," *Science*, 213:406–411 (Jul., 1981).

Valenzuela et al., "The Nucleotide Sequence of the Hepatitis B Viral Genome and the Identification of the Major Viral Genes," *Animal Virus Genetics*, pp. 57–70 (1980).

Villa–Komaroff et al., "A Bacterial Clone Synthesizing Proinsulin," *Proc. Natl. Acad. Sci. USA*, 75:3727–3731 (Aug. 1978).

Wands et al., "Immunodiagnosis of Hepatitis B by Epitope Binding with High–Affinity 1gM Monoclonal Antibodies," *Viral Hepatitis 1981 International Symposium*, Ed. Szmuness, Alter and Maynard, The Franklin Institute, pp. 707–708 (1982).

Zuckerman, "Developments with Hepatitis B Vaccines," *New Trends and Developments in Vaccines*, Ed. A. Voller and H. Friedman, MTP Press Limited, pp. 171–177 (1978).

Summons to Attend Oral Proceedings Pursuant to Rule 71(1) EPC, 5 pages, Nov. 27, 1997.

Opposition by Medeva PLC to European Patent No. 154 902 (New York Blood Center Inc. et al.), 14 pages, Feb. 1996.

Counterstatement by the Patentee, European Patent No. 154 902 (New York Blood Center et al.), pp. 1–22; Amended Claims (Main Request); Basis Schedule for Claims of the Main Request, pp. 1–5 (Oct. 1996).

Supplementary Counterstatement by the Patentee, European Patent No. 154 902 (New York Blood Center et al.) Apr. 17, 1998, including 5 pages of counterstatement, 19 pages of claims, and 1 page of cover letter.

Bruss et al., "Functions of the Large Hepatitis B Virus Surface Protein in Viral Particle Morphogenesis," *Intervirology*, 39:23–31 (1996).

Gerhardt et al., "Phenotypic Mixing of Rodent but Not Avian Hepadnavirus Surface Proteins into Human Hepatitis B Virus Particles," *J. Virology*, 69(2):1201–1208 (Feb. 1995).

Hofmann et al., "Hepatocyte–Specific Binding of L/S–HBV Particles Expressed in Insect Cells," *Biol. Chem. Hoppe–Seyler*, 376:173–178 (Mar. 1995).

Melegari et al., "Properties of Hepatitis B Virus Pre–S1 Deletion Mutants," *Virology*, 199:292–300 (1994).

Milich et al., "Immune Response to the Pre–S(1) Region of the Hepatitis B Surface Antigen (HBsAg): A Pre–S(1)–Specific T–Cell Response can Bypass Nonresponsiveness to the Pre–S(2) and S Regions of HBsAg.," *J. Immunology*, 137(1):315–322 (Jul. 1, 1986).

Neurath et al., "Identification and Chemical Synthesis of a Host Cell Receptor Binding Site on Hepatitis B Virus," *Cell*, 46:429–436 (Aug. 1, 1986).

Petre et al., "Properties of a recombinant yeast–derived hepatitis B surface antigen containing S, preS2 and preS1 antigenic domains," *Arch. Virol.*, [Suppl] 4:137–141 (1992).

Sonveaux et al., "Characterization of the HBsAg particle lipid membrane," *Res. Virol.*, 146:43–51 (1995).

Wand et al., "Chronic Hepatitis", Chapter 23 in Harrison's *Principles of Internal Medicine*, $12^{th}$ Edition, pp. 1337–1340 (1991).

Acute Hepatic Failure Study Group, "Failure of Specific Immunotherapy in Fulminant Type B Hepatitis," *Annals of Internal Medicine*, 86:272–277 (1977).

André et al., "Review: Protective Efficacy of Hepatitis B Vaccines in Neonates," *Journal of Medical Virology*, 44:144–151 (1994).

Cramp et al., "Hepatitis C Virus (HCV) Specific Immune Responses in Anti–HCV Positive Patients Without Hepatitis C Viraemia," *Gut*, 44:424–429 (1999).

Deinhardt, "Human Viral Hepatitis: Hypothesis to Fact," in Hollinger et al., eds., *Proceedings of the 1990 Symposium on Viral Hepatitis and Liver Disease: Contemporary Issues and Future Prospects*, Williams & Wilkins, Baltimore, 1991, pp. 5–11.

Gerlach et al., "Recurrence of Hepatitis C Virus After Loss of Virus-Specific CD4+ T–Cell Response in Acute Hepatitis C," *Gastroenterology*, 117:933–941 (1999).

Mohite et al., "Mechanisms of Liver Cell Damage in Acute Hepatitis B," *Journal of Medical Virology*, 2:199–210 (1987).

Moriyama et al., "Immunobiology and Pathogenesis of Hepatocellular Injury in Hepatitis B Virus Transgenic Mice," *Science*, 248:361–364 (1990).

Naoumov, "Hepatitis C Virus–Specific CD4+ T Cells: Do They Help or Damage?," *Gastroenterology*, 117(4):1012–1014 (1999).

Perrillo, "Treatment of Chronic Hepatitis B," in Hollinger et al., eds., *Proceedings of the 1990 International Symposium on Viral Hepatitis and Liver Disease: Contemporary Issues and Future Prospects*, Williams & Wilkins, Baltimore, 1991, pp. 616–622.

Pol et al., "Immunotherapy of Chronic Hepatitis B by Anti HBV Vaccine," *Acta Gastro–Enterologica Belgica*, vol. LXI:228–233 (Apr.–Jun. 1998).

Stanberry et al., "Herpes Simplex Virus Glycoprotein Immunotherapy of Recurrent Genital Herpes: Factors Influencing Efficacy," *Antiviral Research*, 11:203–214 (1989).

Stanberry et al., "Herpes Simplex Virus Glycoprotein Treatment of Recurrent Genital Herpes," *Journal of Infectious Diseases*, 157(1):156–163 (Jan. 1988).

Hervás–Stubbs et al., "Therapeutic Vaccination of Woodchucks Against Chronic Woodchuck Hepatitis Virus Infection," *Journal of Hepatology*, 27:726–737 (1997).

Hadziyannis et al., "Immunopathogenesis and Natural Course of Anti–Hbe–Positive Chronic Hepatitis with Replicating B Virus," in Hollinger et al., eds., *Proceedings of the 1990 Symposium on Viral Hepatitis: Contemporary Issues and Future Prospects*, Williams & Wilkins, Baltimore, 1991, pp. 673–676.

Couillin et al., "Specific Vaccine Therapy in Chronic Hepatitis B: Induction of T Cell Proliferative Responses Specific for Envelope Antigens," *Journal of Infectious Diseases*, 180:15–26 (1999).

"Immunobiology," edited by Kenji Takeya, Asakura Publications, date unknown, pp. 10–15 and 250 and English translation.

Anonymous third party observations in Opposition to European Patent No. 0 563 093 mailed by EPO on Nov. 11, 1999 (15 pages).

Observations of the Proprietor (Medeva Holdings BV) in response to the opposition and the third party observations against European Patent No. 563093 (43 pages including cover page).

Amended claim 1 of EP 0 563 093 B1 (1 page).

Declaration of Mark Page in opposition to European Patent No. 0 563 093 (22 pages including attachments).

Jin et al., "Human T Cell Response to the Surface Antigen of Hepatitis B Virus (HbsAg)," *Journal of Experimental Medicine*, 168:293–306 (1988).

Cooper et al., "Analysis of a Successful Immune Response against Hepatitis C Virus," *Immunity*, 10:439–449 (Apr. 1999).

Nisini et al., "Human CD4+ T–Cell Response to Hepatitis Delta Virus: Identification of Multiple Epitopes and Characterization of T–Helper Cytokine Profiles," *J. Virol.*, 71(3):2241–2251 (Mar. 1997).

Mar. 22, 2000 Press Release from Celltech Website (8 pages).

Choo et al., "Genetic organization and diversity of the hepatitis C virus," *Proc. Natl. Acad. Sci. USA*, 88:2451–2455 (Mar. 1991).

Rothbard et al., "A sequence pattern common to T cell epitopes," *EMBO J.*, 7(1):93–100 (Jan. 1988).

Borisova et al., "Recombinant Core Particles of Hepatitis B Virus Exposing Foreign Antigenic Determinants on Their Surface", *FEBS Lett*, 259(1):121–124 Dec. 1989).

Brown et al., "Foreign Epitopes in Immunodominant Regions of Hepatitis B Core Particles are Highly Immunogenic and Conformationally Restricted," *Vaccine*, 9:595–601 (Aug. 1991).

May 26, 1999 Notice of Opposition to EP 0 563 093 B1 by SmithKline Beecham (2 pages), Memorandum of Opposition (22 pages), Annex 1 (6 pages), and Annex 2 (3 pages including cover sheet).

Brzosko et al., "Immunostimulation for Chronic Active Hepatitis, "*Lancet*, 2 (8084):311 (1978).

Kassur et al., "Principles and theoretical considerations in the treatment of chronic hepatitis B with immunostimulation, "*Pol Arch Med Wewn (Poland)*, 60(4):305–312 (1978).

Ferrari et al., "The preS1 Antigen of hepatitis B virus is Highly Immunogenic at the T Cell Level in Man," *J. Clin. Invest*, 84:1314–1319 (1989).

Ferrari et al., "Cellular Immune Response to Hepatits B Virus–Encoded Antigens in Acute and Chronic Hepatitis B Virus Infection," *J. Immunology*, 145:3442–3449 (1990).

"Viral Liver Disease," *Lancet*, 3:944–945 (Nov. 3, 1979).

Hong et al., "Seroconversion from HBsAg to antibody after allogeneic bone marrow transplantation," in *Viral Hepatitis and Hepatocellular Carcinoma, Proceedings of the Second International Symposium on Viral Hepatitis and Hepatocellular Carcinoma, Taipei, Dec. 7–9, 1988*, Excerpta Medica Asia Ltd., Hong Kong, pp. 201–205 (1990).

Welmar et al., "Prophylaxis and Therapy of HbsAg Positive Hepatitis," *Biomedicine*, 30:135–138 (1979).

Murray et al., "Protective Immunisation against Hepatitis B with an Internal Antigen of the Virus," *J. Med. Virol.*, 23:101–107 (1987).

Raimondo et al., "Interrupted Replication of Hepatitis B Virus in Liver Tissue of HbsAg Carriers with Hepatocellular Carcinoma," *Virology*, 166:103–112 (1988).

Rehermann et al., "Differential cytotoxic T–lymphocyte responsiveness to the hepatitis B and C viruses in chronically infected patients," *J. Virol.*, 70 (10):7092–102 (Abstract only) (1996).

\* cited by examiner

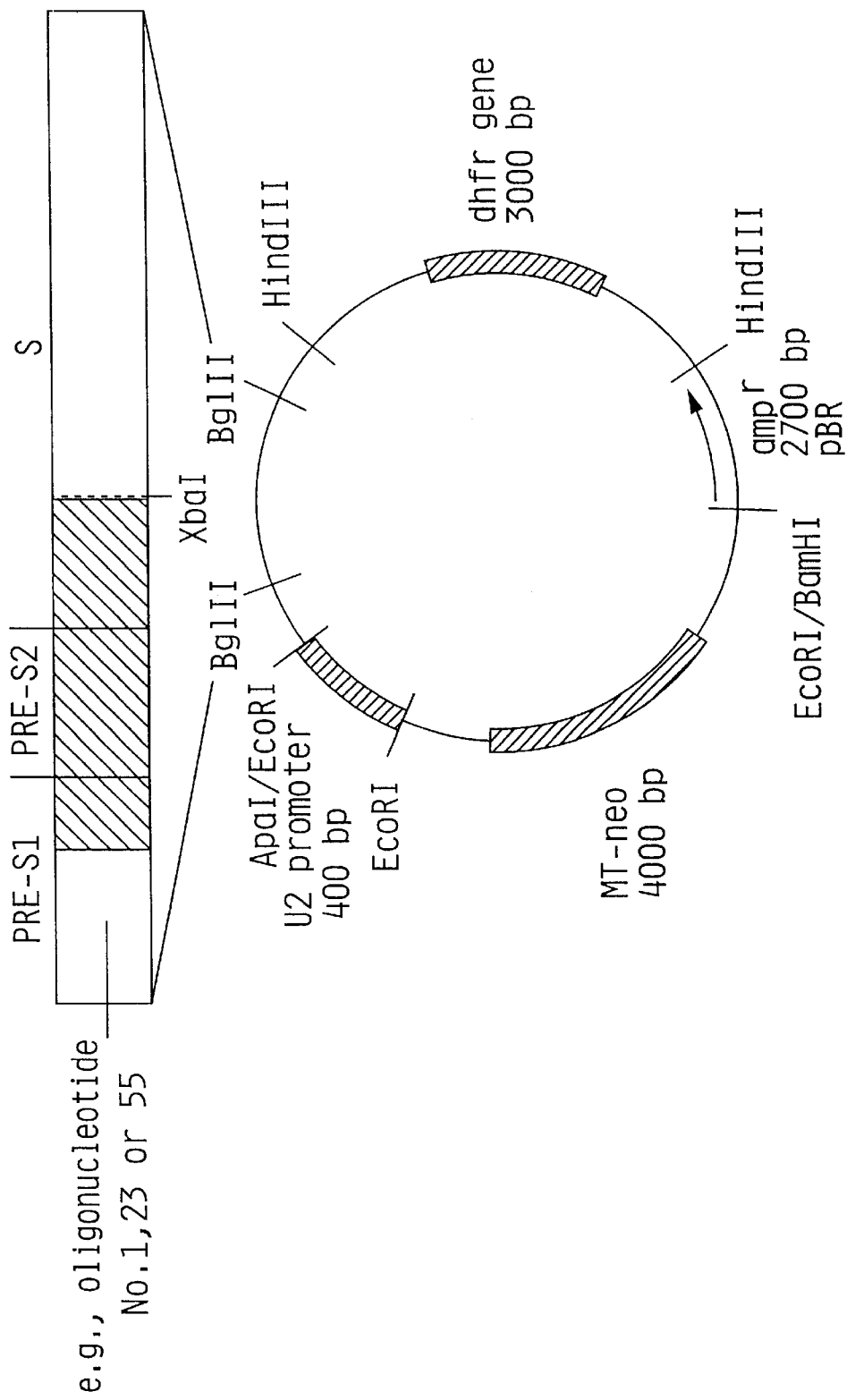

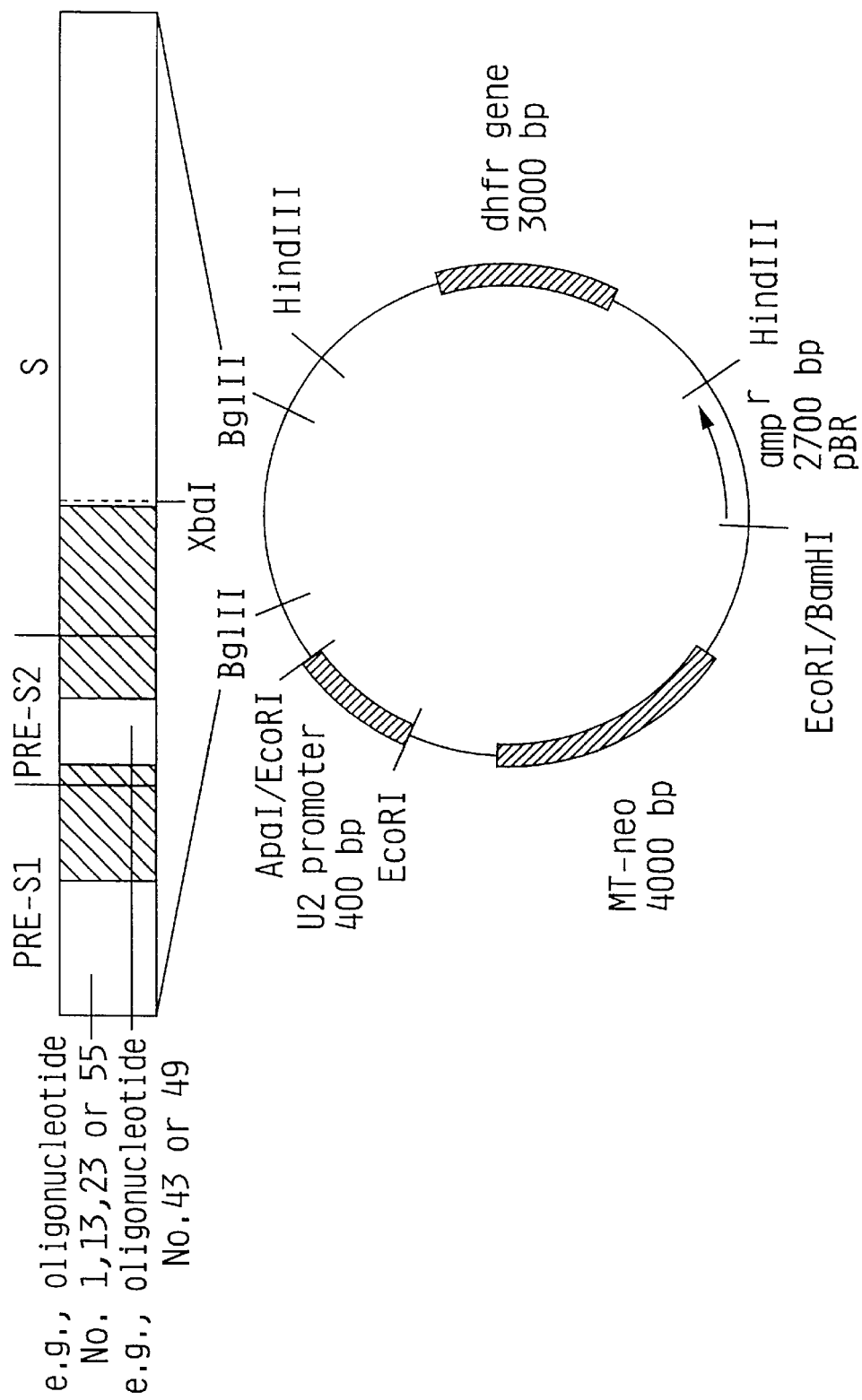

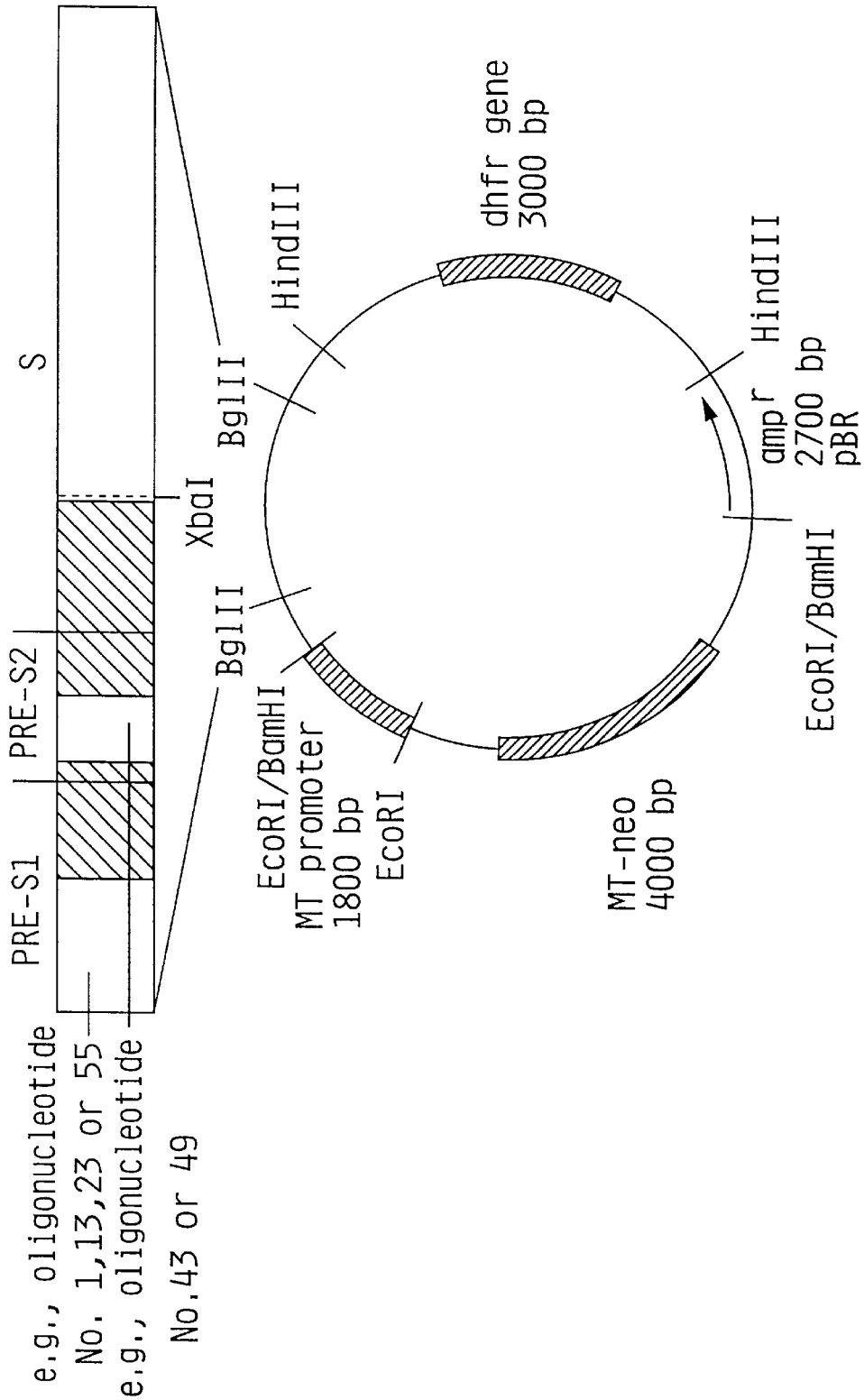

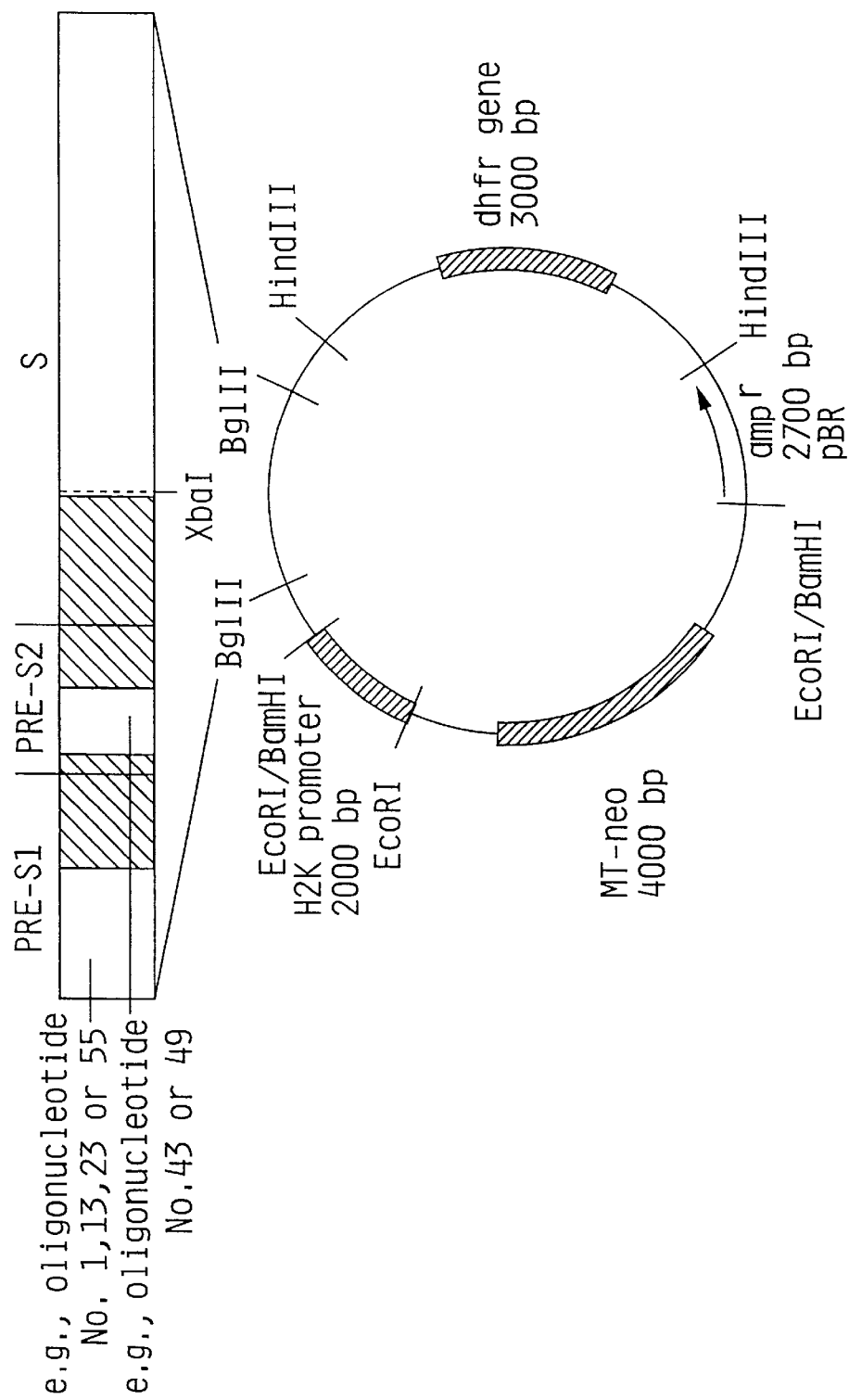

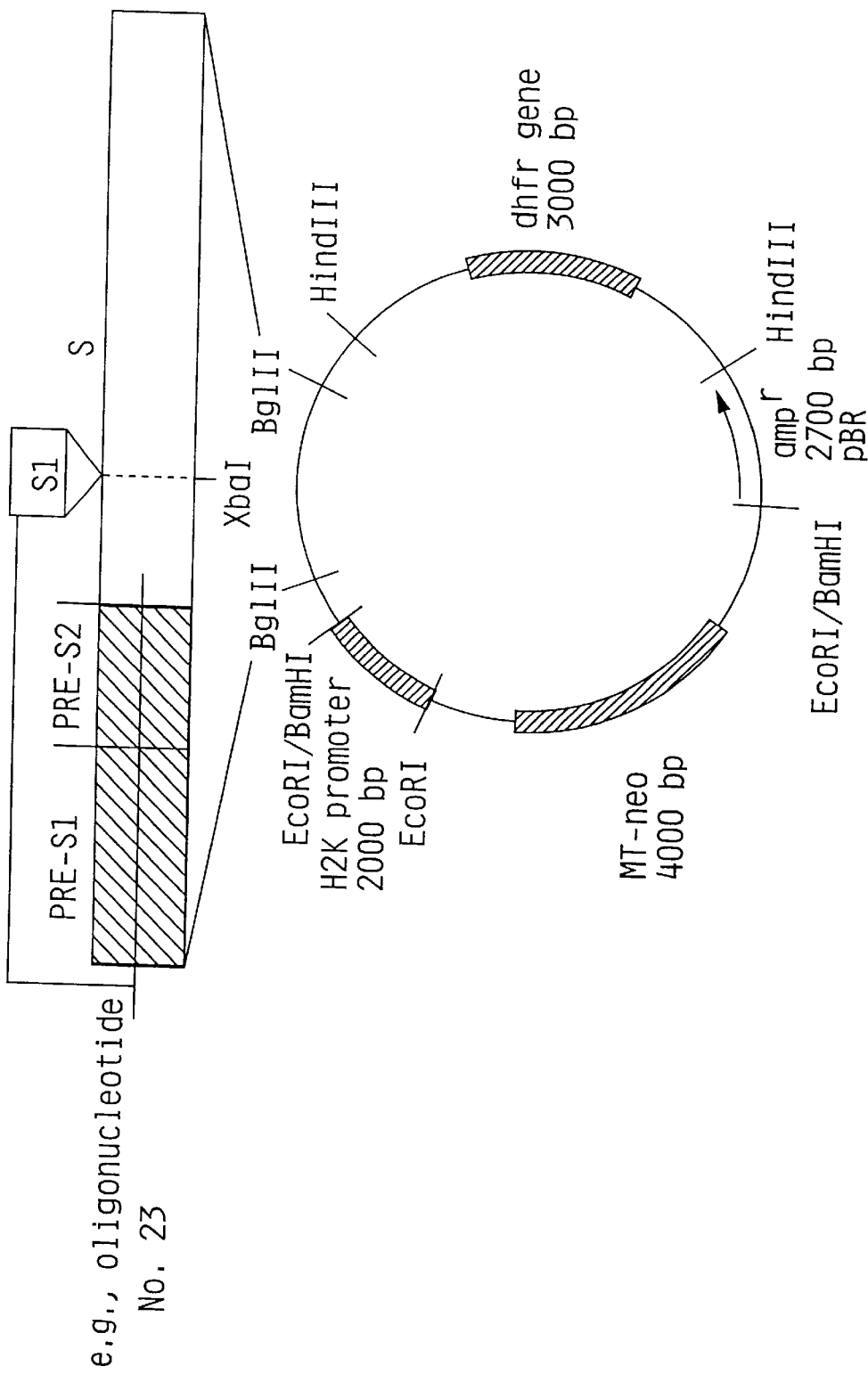

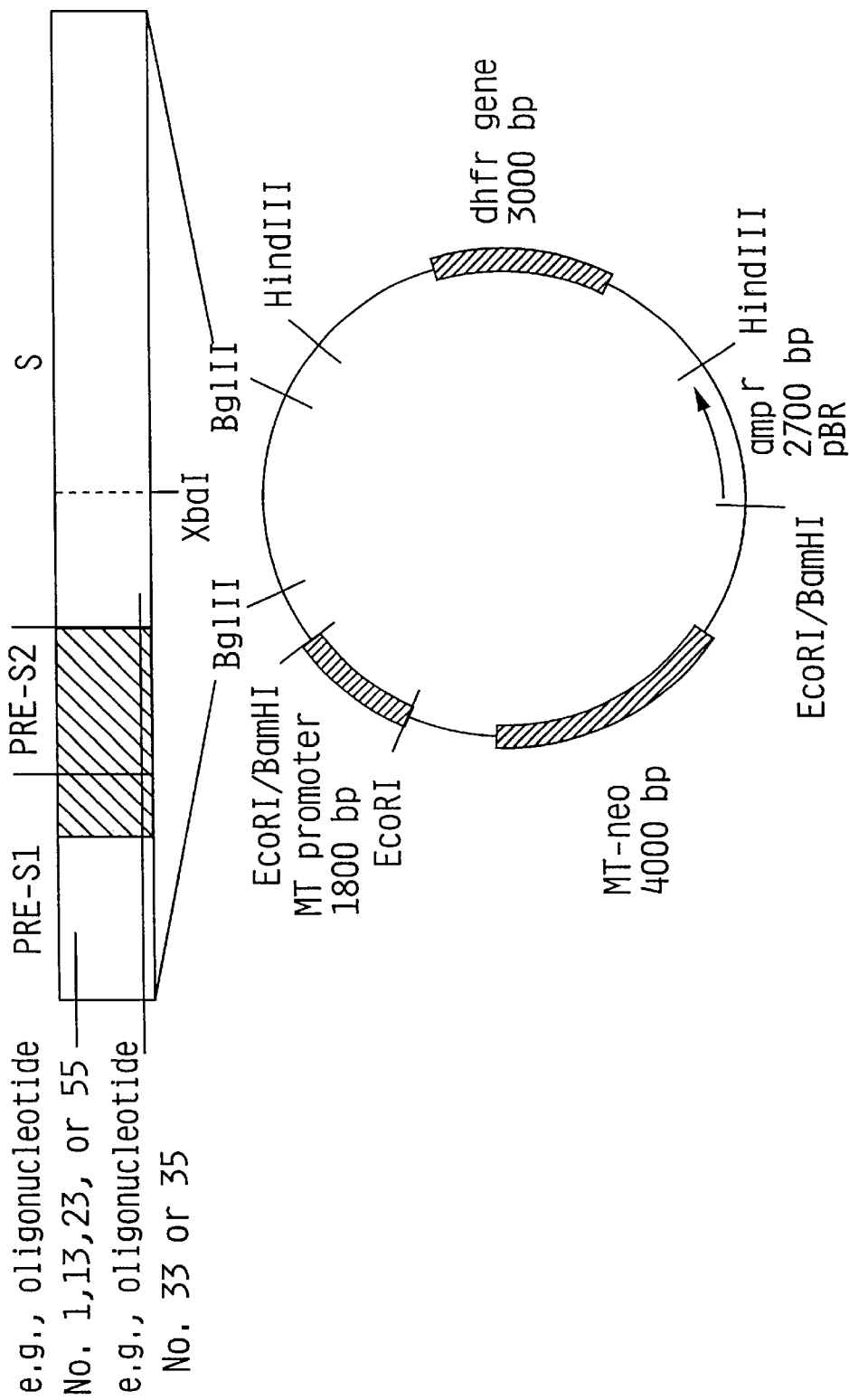

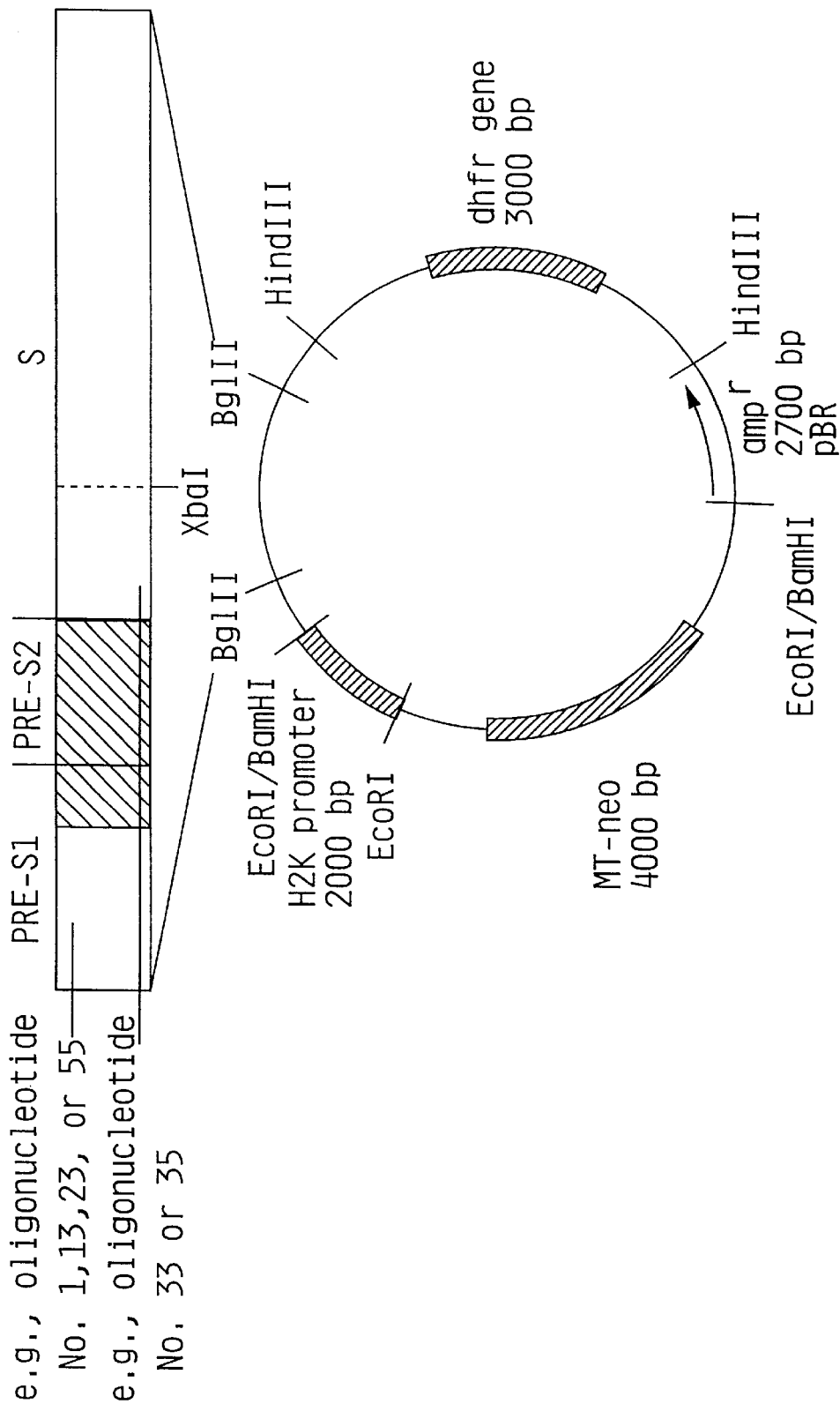

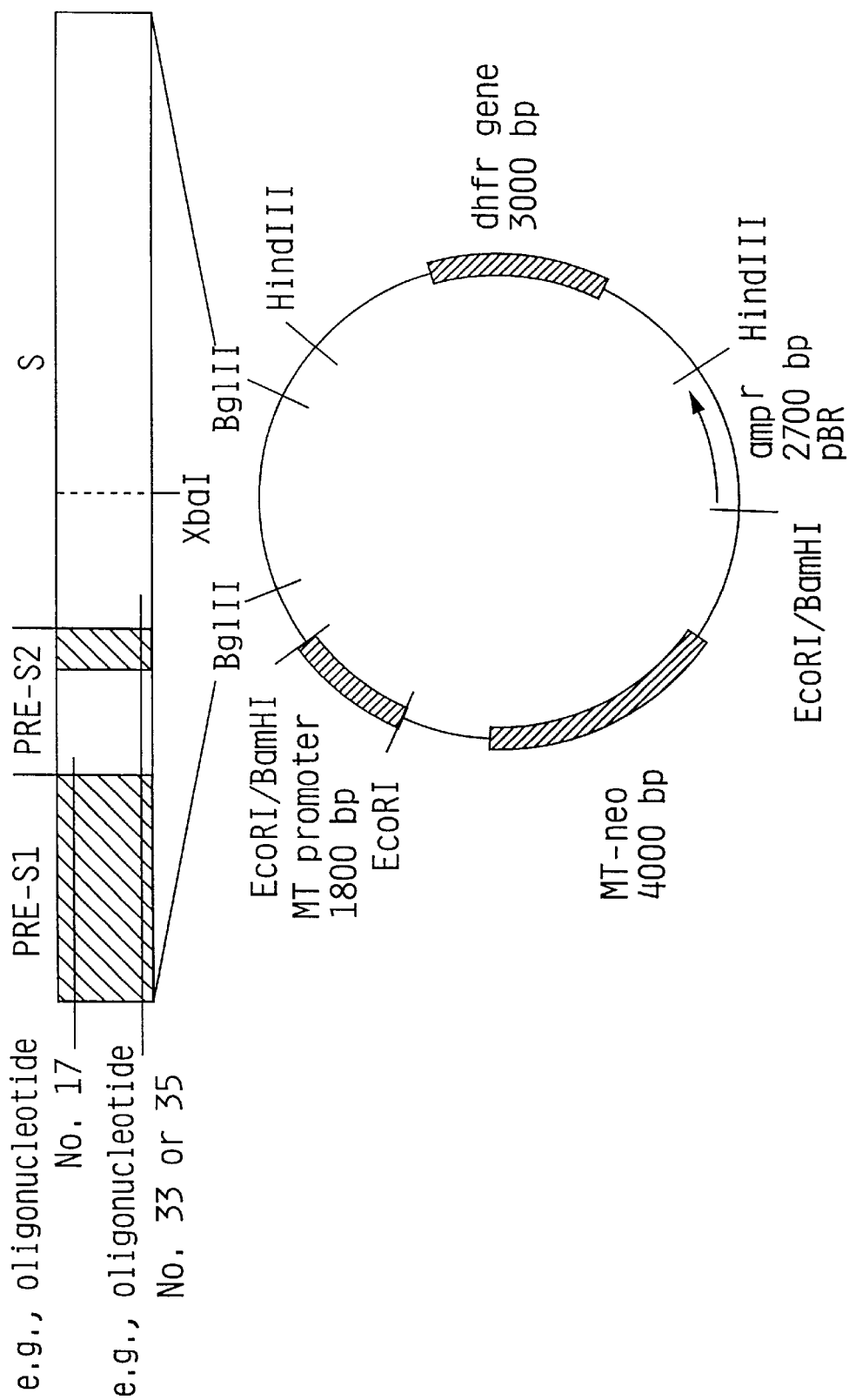

Fig. 9A

```
AGATCTACAGCATGGGGCAGAATCTTTCCACCAGCAATCCTCTGGGATTCTTTCCCGACCA
 BglII    S1
CCAGTTGGATCCAGCCTTCAGAGCAAACACCGCAAATCCAGATTGGGACTTCAATCCCAA

CAAGGACACCTGGCCAGACGCCAACAAGGTAGGAGCTGGAGCATTCGGCCTGGGTTTCAC

CCCACCGCACGGAGGCCTTTTGGGGTGGAGCCCTCAGGCTCAGGGCATACTACAAACTTT
                                 MstII
GCCAGCAAATCCGCCTCCTGCCTCCACCAATCGCCAGTCAGGAAGGCAGCCTACCCCGCT

GTCTCCACCTTTGAGAAACACTCATCCTCAGGCCATGCAGTGGAATT
                          MstII    S2
CCACAACCTTCCACCAAACTCTGCAAGATCCCAGAGTGAGAGGCCTGTATTTCCCTGCTG

GTGGCTCCAGTTCAGGAACAGTAAACCCTGTTCTGACTACTGCCTCTCCCTTATCGTCAA

TCTTCTCGAGGATTGGGGACCCTGCGCTGAACATGGAGAACATCACATCAGGATTCCTAG
                                   S
GACCCCTTCTCGTGTTACAGGCGGGGTTTTTCTTGTTGACAAGAATCCTCACAATACCGC

AGAGTCTAGACTCGTGGTGGACTTCTCTCAATTTTCTAGGGGGAACTACCGTGTGTCTTG
     XbaI
GCCAAAATTCGCAGTCCCCAACCTCCAATCACTCACCAACCTCTTGTCCTCCAACTTGTC

CTGGTTATCGCTGGATGTGTCTGCGGCGTTTTATCATCTTCCTCTTCATCCTGCTGCTAT

GCCTCATCTTCTTGTTGGTTCTTCTGGACTATCAAGGTATGTTGCCCGTTTGTCCTCTAA

TTCCAGGATCCTCAACAACCAGCACGGGACCATGCCGGACCTGCATGACTACTGCTCAAG

GAACCTCTATGTATCCCTCCTGTTGCTGTACCAAACCTTCGGACGGAAATTGCACCTGTA

TTCCCATCCCATCATCCTGGGCTTTCGGAAAATTCCTATGGGAGTGGGCCTCAGCCCGTT

TCTCCTGGCTCAGTTTACTAGTGCCATTTGTTCAGTGGTTCGTAGGGCTTTCCCCCACTG

TTTGGCTTTCAGTTATATGGATGATGTGGTATTGGGGGCCAAGTCTGTTACAGCATCTTG

AGTCCCTTTTTACCGCTGTTACCAATTTTCTTTTGTCTTTGGGTATACATTTAAACCCTA

ACAAAACAAAGAGATGGGGTTACTCTCTAAATTTTATGGGTTATGTCATTGGATGTTATG

GGTCCTTGCCACAAGAACACATCATACAAAAAATCAAAGAATGTTTTAGAAAACTTCCTA

TTAACAGGCCTATTGATTGGAAAGTATGTCAACGAATTGTGGGTCTTTTGGGTTTTGCTG

CCCCTTTTACACAATGTGGTTATCCTGCGTTGATGCCTTTGTATGCATGTATTCAATCTA

AGCAGGCTTTCACTTTCTCGCCAACTTACAAGGCCTTTCTGTGTAAACAATACCTGAACC

TTTACCCCGTTGCCCGGCAACGGCCAGGTCTGTGCCAAGTGTTTGCTGACGCAACCCCCA

CTGGCTGGGGCTTGGTCATGGGCCATCAGCGCATGCGTGGAACCTTTTCGGCTCCTCTGC

CGATCCATACTGCGGAACTCCTAGCCGCTTGTTTTGCTCGCAGCAGGTCTGGAGCAAACA

TTATCGGGACTGATAACTCTGTTGTCCTATCCCGCAAATATACATCGTTTCCATGGCTGC
```

Fig. 9B

```
TAGGCTGTGCTGCCAACTGGATCCTGCGCGGGACGTCCTTTGTTTACGTCCCGTCGGCGC
TGAATCCTGCGGACGACCCTTCTCGGGGTCGCTTGGGACTCTCTCGTCCCCTTCTCCGTC
TGCCGTTCCGACCGACCACGGGGCGCACCTCTCTTTACGCGGACTCCCCGTCTGTGCCTT
CTCATCTGCCGGACCGTGTGCACTTCGCTTCACCTCTGCACGTCGCATGGAGACCACCGT
GAACGCCCACCAAATATTGCCCAAGGTCTTACATAAGAGGACTCTTGGACTCTCAGCAAT
GTCAACGACCGACCTTGAGGCATACTTCAAAGACTGTTTGTTTAAAGACTGGGAGGAGTT
GGGGGAGGAGATTAGGTTAAAGGTCTTTGTACTAGGAGGCTGTAGGCATAAATTGGTCTG
CGCACCAGCACCATGCAACTTTTTCACCTCTGCCTAATCATCTCTTGTTCATGTCCTACT
GTTCAAGCCTCCAAGCTGTGCCTTGGGTGGCTTTGGGGCATGGACATCGACCCTTATAAA
GAATTTGGAGCTACTGTGGAGTTACTCTCGTTTTTGCCTTCTGACTTCTTTCCTTCAGTA
CGAGATCTTCTAGA
  ‾‾‾‾‾‾
   BglII
```

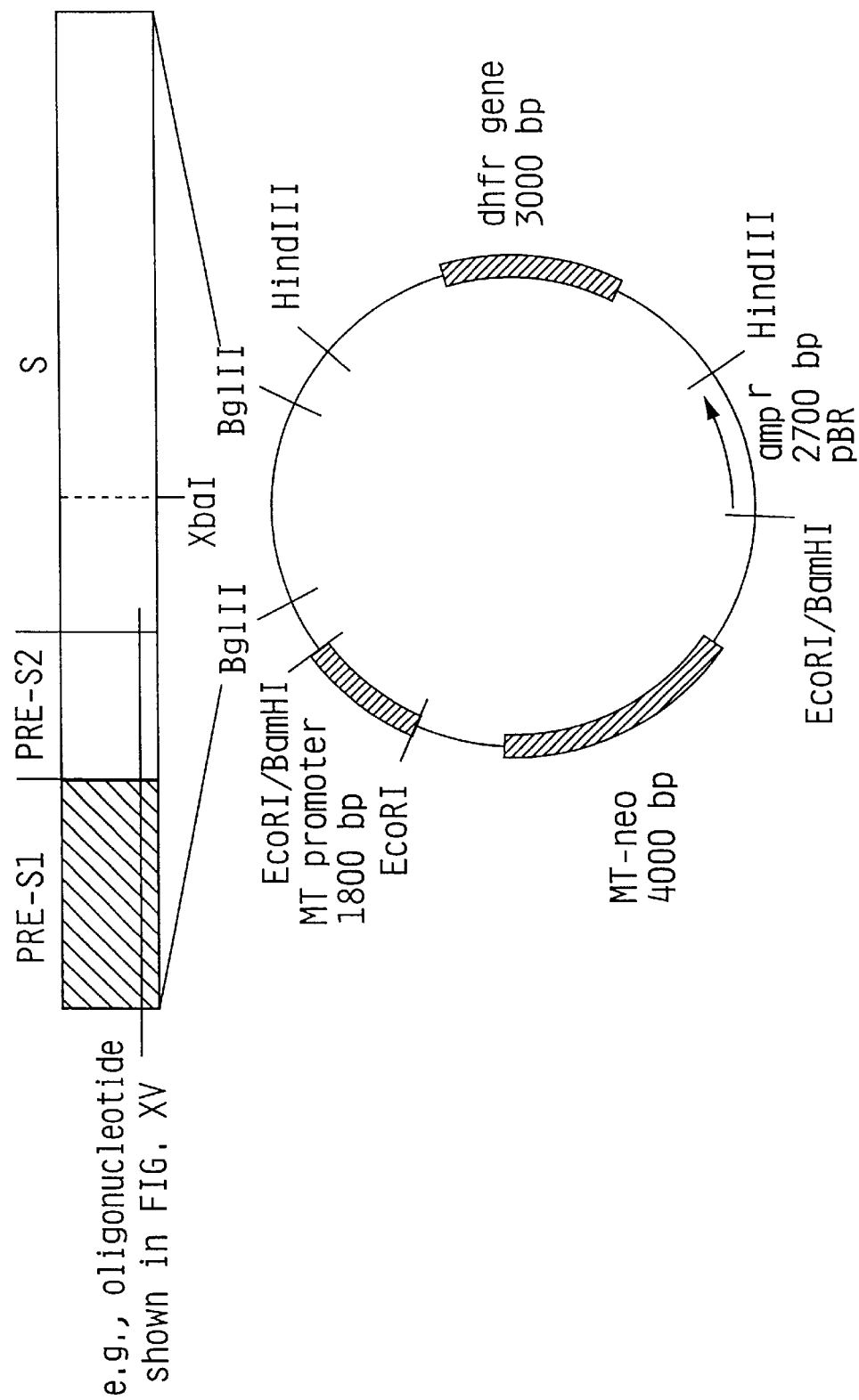

CHARACTERIZATION OF PARTICLES WITH PRE-S$_1$ AND PRE-S$_2$ EPITOPES

□ = OD 283
● = S-ELISA
△ = pre-S1 ELISA
○ = pre-S2 ELISA

Fig. 15

OLIGO SEQUENCE BglII/XbaI of Fig. 10B

AGATCTCCATGCAGTGGAATT
BglII     S2
CCACAACCTTCCACCAAACTCTGCAAGATCCCAGAGTGAGAGGCCTGTATTCCCTGCTG
GTGGCTCCAGTTCAGGAACAGTAAACCCTGTTCTGACTACTGCCTCTCCCTTATCGTCAA
TCTTCTCGAGGATTGGGGACCCTGCGCTGAACACGGAGAACATCACATCAGGATTCCTAG
GACCCCTTCTCGTGTTACAGGCGGGGTTTTTCTTGTTGACAAGAATCCTCACAATACCGC
AGAGTCTAGA
XbaI

Fig. 16

Pre-S PROTEIN

```
                    1         2         3         4         5         6
           12345678901234567890123456789012345678901234567890123456789012

1 ayw      GHHILGNKIYSMGQNLSTSNPLGFFPDHQLDPAFRANTANPDWDFNPNKDTWPDANKVGAGA
2 adyw     GHHILGNKSYSMGQNLSTSNPLGFFPDHQLDPAFRANTNNPDWDFNPNKDTWPDANKVGAGA
3 adw2     MGGWSSKPRKGMTNLSVPNPLGFFPDHQLDPAFGANSNNPDWDFNPVKDDWPAANQVGVGA
4 adw      LGNKSYSIRKGMGTNLSVPNPLGFLPDHQLDPAFGANSTNPDWDFNPIKDHWPAANQVGVGA
5 adr      MGGWSSKPRQGMGTNLSVPNPLGFFPDHQLDPAFGANSNNPDWDFNPNKDQWPEANQVGAGA

MG NLS  NPLGF PDHQLDPAF AN  NPDWDFNP KD WP AN VG GA 6         7         8         9        10        11        12
           345678901234567890123456789012345678901234567890123456789012345678901234

1 ayw      FGLGFTPPHGGLLGWSPQAQGILQTLPANPPPASTNRQSGRQPTPLSPPLRNTHPQAMQWNS
2 adyw     FGLGFTPPHGGLLGWSPQAQGIMQTLPANPPPASTNRQSGRQPTPLSPPLRTTHPHAMHWNS
3 adw2     FGPRLTPPHGGILGWSPQAQGILTTVSTIPPPASTNRQSGRQPTPISPPLRDSHPQAMQWNS
4 adw      FGPGLTPPHGGILGWSPQAQGILTTVSTIPPPASTNRQSGRQPTPISPPLRDSHPQAMQWNS
5 adr      FGPGFTPPHGGLLGWSPQAQGILTTVPAAPPPASTNRQSGRQPTPISPPLRDSHPQAMQWNS

FG   TPPHGG LGWSPQAQGI  T    PPPASTNRQSGRQPTP SPPLR  HPQAM WNS 12   13        14        15        16        17
           5678901234567890123456789012345678901234567890123456789012345678901234

1 ayw      TTFHQTLQDPRVRGLYFPAGGSSSGTVNPVLTTASPLSSIFSRIGDPALN
2 adyw     TTFHQTLQDPRVRGLYFPAGGSSSGTVNPVPTTTSPISSIFSRIGDPALN
3 adw2     TAFHQTLQDPRVRGLYLPAGGSSSGTVNPAPNIASHISSISARTGDPVTN
4 adw      TALHQALQDPRVRGLYLPAGGSSSGTVNPAPNIASHISSISARTGDPVTI
5 adr      TTFHQALLDPRVRGLYFPAGGSSSGTVNPVPTTASPISSIFSRTGDPAPN

T HQ L DPRVRGLY PAGGSSSGTVNP    S  SSI  R GDP
```

Fig. 17

PRE-S1 SEQUENCE
adw

```
Met Gly Gly Trp Ser Ser Lys Pro Arg Gln Gly Met Gly Thr Asn Leu Ser Val Pro Asn Pro Leu Gly Phe Phe
ATG GGA GGT TGG TCT TCC AAA CCT CGA CAA GGC ATG GGG ACG AAT CTT TCT GTT CCC AAT CCT CTG GGA TTC TTT
‾‾‾                                     ‾‾‾‾‾‾‾
Start Pre-S(1)                            TaqI Pro Asp His Gln Leu Asp Pro Ala Phe Gly Ala Asn Ser Asn Asn Pro Asp Trp Asp Phe Asn Pro Asn Lys Asp
CCC GAT CAC CAG CTT GAC CCT GCG TTC GGA GCC AAC TCA AAC AAT CCA GAT TGG GAC TTC AAC CCC AAC AAG GAT
                                    ‾‾‾‾‾‾‾
                                    Sau 961

Gln Trp Pro Glu Ala Asn Gln Val Gly Ala Gly Ala Phe Gly Pro Gly Phe Thr Pro Pro His Gly Gly Leu Leu
CAA TGG CCA GAG GCA AAT CAG GTA GGA GCG GGA GCA TTC GGG CCA GGG TTC ACC CCA CAC GGC GGT CTT TTG
    ‾‾‾‾‾‾‾
    BalI

Gly Trp Ser Pro Gln Ala Gln Gly Ile Leu Thr Thr Val Pro Ala Ala Pro Pro Ala Ser Thr Asn Arg Gln
GGG TGG AGC CCT CAG GCT CAG GGC ATA TTG ACA ACA GTG CCA GCA GCA CCT CCT GCC TCC ACC AAT CGG CAG

Ser Gly Arg Gln Pro Thr Pro Ile Ser Pro Pro Leu Arg Asp Ser His Pro Gln Ala Met Gln Trp Asn Ser Thr
TCA GGA AGA CAG CCT ACT CCC ATC TCT CCA CCT CTA AGA GAC AGT CAT CCT CAG GCC ATG CAG TGG AAT TCC ACA
                                                                            ‾‾‾         ‾‾‾‾‾‾‾
                                                                            Start        EcoRI
                                                                            Pre-S(2)
```

Fig. 18

PRE-S1 SEQUENCE ayw

```
Met Gly Gln Asn Leu Ser Thr Ser Asn Pro Leu Gly Phe Phe
ATG GGG CAG AAT CTT TCC ACC AGC AAT CCT CTG GGA TTC TTT
———
Start Pre-S(1)

Pro Asp His Gln Leu Asp Pro Ala Phe Arg Ala Asn Thr Ala Asn Pro Asp Trp Asp Phe Asn Pro Asn Lys Asp
CCC GAT CAC CAG TTG GAT CCA GCC TTC AGA GCA AAC ACC GCA AAT CCA GAT TGG GAC TTC AAT CCC AAC AAG GAC

Thr Trp Pro Asp Ala Asn Lys Val Gly Ala Gly Ala Phe Gly Leu Gly Phe Thr Pro Pro His Gly Gly Leu Leu
ACC TGG CCA GAC GCC AAC AAG GTA GGA GCT GGA GCA TTC GGG CTG GGT TTC ACC CCA CCG CAC GGA GGC CTT TTG
                                                                ———
                                                                BalI

Gly Trp Ser Pro Gln Ala Gln Gly Ile Leu Glu Thr Leu Pro Ala Asn Pro Pro Pro Ala Ser Thr Asn Arg Gln
GGG TGG AGC CCT CAG GCT CAG GGC ATA CTA CAA ACT TTG CCA GCA AAT CCG CCT CCT GCC TCC ACC AAT CGC CAG

Ser Gly Arg Gln Pro Thr Pro Leu Ser Pro Pro Leu Arg Asn Thr His Pro Gln Ala Met Gln Trp Asn Ser Thr
TCA GGA AGG CAG CCT ACC CCG CTG TCT CCA CCT TTG AGA AAC ACT CAT CCT CAG GCC ATG CAG TGG AAT TCC ACT
                                                                              ———      ———
                                                                              Start    EcoRI
                                                                              Pre-S(2)
```

Fig. 19

PRE-S1 SEQUENCE

```
Met Gly Gly Trp Ser Ser Lys Pro Arg Lys Gly Met Gly Thr Asn Leu Ser Val Pro Asn Pro Leu Gly Phe Phe
ATG GGA GGT TGG TCA TCA AAA CCT CGC AAA GGC ATG GGG ACG AAT CTT TCT GTT CCC AAT CCT CTG GGA TTC TTT
─────────
Start Pre-S(1)

Pro Asp His Gln Leu Asp Pro Ala Phe Gly Ala Asn Ser Asn Asn Pro Asp Trp Asp Phe Asn Pro Val Lys Asp
CCC GAT CAT CAG TTG GAC CCT GCA TTC GGA GCC AAC TCA AAC AAT CCA GAT TGG GAC TTC AAC CCC GTC AAG GAC
                                        ──────
                                        Sau 961

Asp Trp Pro Ala Ala Asn Gln Val Gly Val Gly Ala Phe Gly Pro Arg Leu Thr Pro Pro His Gly Gly Ile Leu
GAC TGG CCA GCA GCC AAC CAA GTA GGA GTG GGA GCA TTC GGG CCA AGG CTC ACC CCT CCA CAC GGC GGT ATT TTG
                                ─────
                                BalI

Gly Trp Ser Pro Glu Ala Gln Gly Ile Leu Thr Thr Val Ser Thr Ile Pro Pro Pro Ala Ser Thr Asn Arg Gln
GGG TGG AGC CCT CAG GCT CAG GGC ATA TTG ACC ACA GTG TCA ACA ATT CCT CCT CCT GCC TCC ACC AAT CGG CAG

Ser Gly Arg Gln Pro Thr Pro Ile Ser Pro Pro Leu Arg Asp Ser His Pro Gln Ala Met Gln Trp Asn Ser Thr
TCA GGA AGG CAG CCT ACT CCC ATC TCT CCA CCT CTA AGA GAC AGT CAT CCT CAG GCC ATG CAG TGG AAT TCC ACT
                                                                         ─────     ─────
                                                                         Start     EcoRI
                                                                         Pre-S(2)
```

Fig. 20

PRE-S1 SEQUENCE

```
Met Gly Gly Trp Ser Ser Lys Pro Arg Lys Gly Met Gly Thr Asn Leu Ser Val Pro Asn Pro Leu Gly Phe Phe
ATG GGA GGT TGG TCA TCA AAA CCT CGC AAA GGC ATG GGG ACG AAT CTT TCT GTT CCC AAC CCT CTG GGA TTC TTT
Start Pre-S(1)

Pro Asp His Gln Leu Asp Pro VAL Phe Gly Ala Asn Ser Asn Asn Pro Asp Phe Asn Pro Ile Lys Asp
CCC GAT CAT CAG TTG GAC CCT GTA TTC GGA GCC AAC TCA AAC AAT CCA GAT TGG GAC TTC AAC CCC ACT AAG GAC
                                              Sau 961

His Trp Pro Ala Ala Asn His Val Gly Val Gly Ala Phe Gly Pro Arg Phe Thr Pro Pro His Gly Gly Val Leu
CAC TGG CCA GCA GCC AAC CAC GTA GGA GTG GGA GCA TTC GGG CCA AGG TTC ACC CCT CCA CAC GGC GGT GTT TTG
                       BalI

Gly Trp Ser Pro Gln Ala Gln Gly Met Leu Thr Pro Val Ser Thr Ile Pro Pro Pro Ala Ser Ala Asn Arg Gln
GGG TGG AGC CCT CAG GCT CAG GGC ATG TTG ACC CCA GTA TCA ACA ATT CCT CCT CCT GCC TCC GCC AAT CGG CAG

Ser Gly Arg Gln Pro Thr Pro Ile Ser Pro Pro Leu Arg Asp Ser His Pro Gln Ala Met Gln Trp
TCA GGA AGG CAG CCT ACT CCC ATC TCT CCA CCT CTA AGA GAC AGT CAT CCT CAG CCC ATG CAG TGG
                                                                        Start
                                                                        Pre-S(2)
```

HEPATITIS B SURFACE ANTIGEN VACCINE

This is a divisional of U.S. application Ser. No. 08/258, 549, filed Jun. 10, 1994, U.S. Pat. No. 6,022,543, which is a continuation of U.S. application Ser. No. 07/340,172, filed Feb. 21, 1989, now abandoned, which was the National Stage of International Application No. PCT/EP88/00551, filed June 22, 1988.

FIELD OF THE INVENTION

The invention relates to Hepatitis B surface antigen ("HBs antigen" or "HBsAG") particles which are composed of polypeptides prepared by recombinant DNA processes, DNA sequences coding for these polypeptides and cell lines for the expression of the same. The present invention relates especially to new particles having increased immunogenicity.

BACKGROUND OF THE INVENTION

Expression in Host Cells

Advances in vaccine production techniques have made it possible to synthesize polypeptides corresponding to the HBs antigen in bacteria, yeast and mammalian cells. Transcription of eukaryotic genes in bacteria and yeast, however, adversely affects the efficaciousness of these polypeptides as antigens due to several drawbacks concerning the glycosilation and secretion of the polypeptides and composition of the particle formed therefrom.

For example, in the case of the Hepatitis B virus, the polypeptide antigens produced in vivo are heavily glycosilated (Gerlich, 1984: J. Virol.: 52 (2), 396). In prokaryotes, glycosilation is not an essential process so that polypeptides produced by genetically engineered bacteria are either not glycosilated or are incompletely glycosilated. In either case, polypeptides corresponding to HBsAg, when expressed in bacteria, do not raise antibodies which will see HBsAg sufficiently well for an effective vaccine. Although yeast as a eukaryotic host is capable of more complete glycosilation, polypeptides corresponding to HbsAg expressed in yeast share the same deficiency as in the case of bacterial expression. (Murray et al., 1979: Nature, 282, 575; Valenzuela et al., 1982: Nature, 298, 347; Miyariohara et al., 1983: PNAS, 80, 1).

As a further example, in bacteria the eukaryotic structural gene of the HBsAg is in most cases not efficiently transcribed. Furthermore the structure and function of the eukaryotic HBsAg gene product may be dependent on the additional post-translational processes of the linkage of disulfide bonds which can not be accomplished by the bacterial host.

Still further, the expressed polypeptide is rarely secreted from the bacterial host cells. They must be lysed to harvest the expressed polypeptide. During the purification process bacterial wall components may contaminate the polypeptide and cause serious allergic reactions or lead to anaphylactic shock in patients.

Finally, eukaryotic promoters usually do not work in bacteria and must be substituted by a bacterial promoter which can result in modification of the polypeptide expressed. (Offensperger et al., 1985: PNAS, 82, 7540; Valenzuela et al., 1980: ICN-UCLA Symp, Mol. Cell. Biol., 18 57).

FORMATION AND SECRETION OF PARTICLES

The natural forms of Hepatitis B virus ("HBV") and HBV protein occur in three distinct morphologies:

- the HBV-virion (Dane particle), which is thought to be the infectious material,
- the filaments, and
- the 20 or 22 nm particles (hereinafter "20 nm particle") which consist only of a protein envelope.

The most interesting form for an efficient vaccine is the 20 nm particle because 1) the coding sequences are entirely known, 2) it is completely uninfectious, and 3) it causes some useful immunogenicity in a human organism.

The three known components of HBV particles differ in their relative amounts of the protein composition. There are three monomers called the major protein with 226 amino acids, the middle protein with 281 amino acids, and the large protein with 389 or 400 amino acids, depending on the subtype ayw and adw, respectively. The large protein is encoded by the complete sequence of the pre-$S_1$-, pre-$S_2$- and S-regions, whereas the middle protein is derived from only the pre-$S_2$- and S-regions, and finally the major protein from only the S-region (Tiollais et al., 1985; Nature, 317, 489; Dubois et al., 1980: PNAS, 77, 4549; McAlzer et al., 1984: Nature, 307, 178).

The infectious virion of HBV (Dane particle) contains 40-80 times more of the high molecular monomers—the pre-$S_1$ and pre-$S_2$ peptides—compared to the 20 nm particle. It is now known that these pre-S polypeptides may be associated Faith some biological and clinical implications. The polyalbumin receptor on the pre-S polypeptides can bind polymerized albumins from humans and chimpanzees which are susceptible to HBV (Thung et al., 1983: Liver, 3, 290; Machida et al., 1984: Gastroenterology, 86, 910). This narrow host range and the known receptor for poly human serum albumin on human hepatocytes explain the hepatotropism of HBV: Dane particles are able to contact hepatocytes via poly human serum albumin taken up by hepatocytes from circulation. Based on this evidence the pre-S peptides should be helpful for an efficient vaccine against HBV because its antibody could be expected to block the significant site on Dane particles that are required for entering hepatocytes (Tiollais et al., 1985: Nature, 317, 489; Millich et al., 1985: Science, 228, 1195).

Literature data would also suggest a better protection against the infectious Dane-particle where the pre-$S_1$ epitope is present in much higher ratio than on the envelope particles.

The vaccine obtained from natural sources (e.g., donor blood), which causes a limited immunogenic protection, contains (almost) none of the pre-S proteins; this is due to two different reasons. First, the purification process is focused on the noninfectious 20 nm particles. These contain at most 1% pre-$S_1$ peptide compared to 15–20% in the Dane particle (Gerlich, 1984: J. Vir., 52 (2), 396: Tiollais et al., 1985: Nature, 317, 489; Gerlich, 1982: Virology, 123, 436). Second, the 20 nm particles are isolated from sera of anti-HBE positive carriers (Hevac B, HepaVac B) or are digested by proteases during the purification process. This proteolytic digestion has been shown to cut the pre-S-polypeptides leaving only the S monomers. As a result these vaccines contain none or very little pre-S polypeptides.

Therefore there is a demand for a vaccine in the form of HBs antigen particles which possess a high immunogenicity due to the composition of the particle, which undergo glycosilation in the cell and which are secreted continuously from the particle-producing cell.

REFERENCES AND PATENTS

EP-A-72 318 describes the expression of HBsAg in yeast cells, which have been transformed by a vector comprising a yeast replicon, a yeast promoter and a DNA sequence coding for the S peptide.

Laub et al., J. Virol., Vol. 48, No. 1, pp. 271–280, 1983, disclose the construction of a vector starting from simian virus 40 into which the HBsAq including the 163 codon precursor sequence was incorporated. Laub et al. report that CV-1 cells transformed with said vector yield a better expression when the vector contains only the coding sequence for the S protein as compared to the above vector which comprises additionally also the 163 codon precursor sequence.

Also Takeda Chemical Ind., Japanese Patent Application No. J5-8194-897-A describes the expression of the entire pre-S and S peptides. Reference is also made to the expression of the adw subtype.

Feitilson et al., Virology, Vol. 130, pp. 75–90, 1983, have described the partial expression of polypeptides within the pre-S coding sequence, including species with 24000, 28000, 32000, 43000 and 50000 dalton.

Further, DE-OS 34 39 400 describes the expression of an immunogenic polypeptide sequence of Hepatitis B virus. Said sequence represents a partial sequence of the pre-S$_1$ polypeptide, comprises 108 or 119 codons and starts with the first starting codon of HBsAg, and terminates 281 codons in front of the stop codon.

EP-A-154 902 discloses a Hepatitis B vaccine which contains a peptide with an amino acid chain of at least six consecutive amino acids within the pre-S chain coding region of the envelope of Hepatitis B virus. This vaccine is free of an amino acid sequence corresponding to the naturally occurring envelope proteins of Hepatitis B virus.

Also Kent et al. have described in Pept. Chem., Vol 22, pp. 16770, 1984, that a chemically synthesized peptide comprising the N-terminal 26 amino acids of the pre-S$_2$ region can serve as an antigen and may therefore be suitable as a synthetic vaccine.

OBJECTS OF THE INVENTION

None of the above discussed references consider the possibility that, by altering the composition of the monomers making up the 20 nm particles and approaching thereby the natural composition of the Dane particle, the antigenicity of the particle can be improved.

As discussed mentioned above, the immunogenicity of the peptide monomers of the virus envelope protein is very poor compared to assembled protein particles. The object of this invention is the development of protein particles which contain an amount of the pre-S polypeptide epitopes comparable to the natural composition of the surface structure of the infectious Dane particle.

It is a further object to utilize additional pre-S peptides containing important protective epitopes in the development of a better immune response, a longer protection and lower non-responder rate as compared to all the other products either already marketed or under development.

It is a further object to express HBsAg in mammalian cells. This requires overcoming known difficulties where expression of the desired peptide in a mammalian cell can result in:

different regulatory mechanisms for the three translational/(transcriptional) products
promoter-promoter inhibition
different strength of the start codons
not all peptides expressed.

SUMMARY OF THE INVENTION

The term "HBV S peptide" as used herein refers to the peptide encoded by the entire S region of the HBV genorne. The term "HBV pre-S$_2$ peptide" as used herein refers to the peptide encoded by the entire pre-S$_2$ and S regions of the HBV genome. The term "HBV pre-S$_1$ peptide" as used herein refers to the polypeptide encoded by the entire pre-S$_1$, pre-S$_2$ and S regions of the HBV genome. The term "epitope" as used herein refers to a sequence of at least six consecutive amino acids encoded by the designated genome region (e.g., a "HBV pre-S$_2$ epitope" refers to a sequence of at least six amino acids encoded by the pre-S$_2$ region of the HBV genome). As used herein "antigenicity" means the ability to provoke an immune response (e.g., acting as a vaccine or an antigen), the ability to cause the production of antibodies (e.g. acting as an antigen) and/or the ability to interact with a cell surface receptor so as to enhance an immune response or production of antibodies (e.g., reacting with a T-cell surface receptor to enhance immune response).

The term "HBV" means any subtype of the virus, particularly adw, ayw, adr and ayr, described in the literature (P. Valenzuela, Nature Vol. 280, p. 815 (1979), Gerlich, EP-A-85 111 361, Neurath, EP-A-85 102 250). Examples of peptide sequences thereof, from which the epitopes of this invention can be derived, are shown in Figures XVI to XX.

In accordance with the present invention, recombinant DNA molecules are disclosed which comprise a first DNA sequence and a second DNA sequence. The first DNA sequence encodes for expression of an amino acid sequence a portion of which displays the antigenicity of an epitope selected from the group consisting of an HBV pre-S$_1$ epitope and an HBV pre-S$_2$ epitope. The second DNA sequence encodes for expression of a peptide which upon secretion will form particles which are at least 10 nm in diameter. These particles are believed to be the smallest particles which will effectively form a good vaccine. Preferably the peptide which upon secretion will form particles which are at least 10 nm in diameter is either HBV S peptide, HBV core antigen, polio surface antigen, Hepatitis A surface antigen, Hepatitis A core antigen, HIV surface antigen and HIV corehtigen. A substantial portion or all of the HBV S peptide is especially preferred as the peptide encoded by the second DNA sequence. In the recombinant DNA molecules encoding for the first and second DNA sequences must be (1) in the same reading frame, (2) encode for respective discrete regions of a single peptide, and (3) be operatively linked to an expression control sequence. Finally, these recombinant DNA molecules are free of DNA sequences encoding for the expression of the entire HBV pre-S$_1$ peptide or HBV pre-S$_2$ peptide.

Specific recombinant DNA molecules of the present invention are also disclosed wherein the first DNA sequence comprises a nucleotide sequence corresponding to the nucleotide sequence of (1) the HBV pre-S$_1$ and pre-S$_2$ regions from which the pre-S$_2$ start codon ATG has been deleted, (2) the HBV pre-S$_1$ and pre-S$_2$ regions and wherein the sequences flanking the pre-S$_1$ ATG have been changed from the natural sequence, (3) the HBV pre-S$_1$ and pre-S$_2$ regions and wherein the sequences flanking the pre-S$_2$ ATG have been changed from the natural sequence, (4) the HBV pre-S$_1$ and pre-S$_2$ regions and wherein the 5' terminus of the pre-S$_1$ region has been deleted, (5) the HBV pre-S$_1$ and pre-S$_2$ regions and wherein the 5' terminus of the pre-S$_2$ region has been deleted, (6) the HBV pre-S$_1$ region and wherein the 3' terminus of the pre-S$_1$ region has been deleted, (7) the HBV pre-S$_2$ region and wherein the 3' terminus of the pre-S$_2$ region has been deleted, (8) the HBV pre-S$_1$ and pre-S$_2$ regions from which the pre-S$_2$ ATG has been deleted and the second DNA sequence comprises a sequence corresponding to the nucleotide sequence of the HBV S region from which the S ATG has been deleted, and/or (a) an oligonucleotide described in Table I.

Host cells transfected with the recombinant DNA molecules of the present invention are also disclosed. As used herein, "transfected" or "transfection" refer to the addition of exogenous DNA to a host cell whether by transfection, transformation or other means. Host cells include any unicellular organism capable of transcribing and translating recombinant DNA molecules including without limitation mammalian cells, bacteria and yeast. Host cells of the present invention may also be cotransfected with a second recombinant DNA molecule comprising a DNA sequence encoding for expression of an amino acid sequence corresponding to a substantial portion or all of the amino acid sequence of the HBV S peptide.

Peptides are also disclosed comprising a first discrete region and a second discrete region. The first region displays the antigenicity of an epitope of an HBV pre-S$_1$ epitope or an HBV pre-S$_2$ epitope. The second region correspond to a substantial portion of a peptide which upon secretion will form particles which are at least 10 nm in diameter. Preferably the peptide which upon secretion will form particles which are at least 10 nm in diameter is either HBV S peptide, HBV core antigen, polio surface antigen, Hepatitis A surface antigen, Hepatitis A core antigen, HIV surface antigen and HIV core antigen. A substantial portion or all of the HBV S peptide is especially preferred. Preferably, the first region is located closer to the N-terminus of the peptide than the second region.

Immunogenic particles are also disclosed which comprise a plurality of first peptide monomers. Each of said first peptide monomers comprises a first discrete region and a second discrete region which can be the same as the first and second discrete regions of the peptides described above. Immunogenic particles are also disclosed which further comprise a plurality of second peptide monomers and wherein the first and second peptide monomers are bound together by interactive forces between the monomers. Each of said second peptide monomers comprising an amino acid sequence corresponding to a substantial portion of or all of the amino acid sequence of the HBV S peptide.

Immunogenic particles are also disclosed which contain substantially more than one percent, preferably more than five percent, of the pre-S$_1$ epitope. As used herein, a particle "contains one percent" of a designated epitope if peptide monomers having the designated epitope constitute one percent of all protein in the particle. Immunogenic particles which contain substantially more than ten percent, preferably more than fifteen percent, of the pre-S$_2$ epitope are also disclosed.

Pharmaceutical preparations and preparations useful for production of antibodies comprising the above-described immunogenic particles in sufficient concentration to elicit an immune response upon administration of said preparation and a suitable carrier are also disclosed. Suitable carriers are known to those skilled in the art and may include simple buffer solutions. other preparations useful for production of antibodies are disclosed comprising the above-described immunogenic particles in sufficient concentration to elicit an immune response upon administration of said preparation and a suitable carrier. Suitable carriers are known to those skilled in the art and may include simple buffer solutions.

A process for producing a transfected host call is disclosed which comprises providing host cells which have been made competent for uptake of DNA, exposing the host cells to a first preparation of DNA comprising one of the above-described recombinant DNA molecules, allowing under suitable conditions the host cells to take up DNA from the first preparation of DNA, and selecting for host cells which have taken up (exogenous DNA. The process may further comprise exposing the host cells to a second preparation of DNA comprising a DNA molecule encoding for a peptide including the amino acid sequence of the HBV S peptide and allowing under suitable conditions the host cells to take up DNA from the second preparation of DNA. The exposure and uptake of the second preparation of DNA can be done before or after exposure to and uptake of the first DNA preparation. Alternatively, the first DNA preparation can also include a DNA molecule encoding for a peptide including the amino acid sequence of the HBV S peptide.

A method for producing a peptide is also disclosed which comprises preparing an above-described recombinant DNA molecule, transfecting a host cell with the recombinant DNA molecule, culturing the host cell under conditions allowing expression and secretion of protein by the host cell, and collecting the peptide produced as a result of expression of DNA sequences within the recombinant DNA molecule. The peptide produced by such method can contain less than the entire amino acid encoded by the coding region of the recombinant DNA molecule. This may result from transcription and/or translation of only a portion of the coding region of the recombinant molecule or by deletions made in the peptide after translation.

A method of producing immunogenic particles is disclosed comprising preparing an above-described recombinant DNA molecule, transfecting a host cell with the recombinant DNA molecule, culturing the host cell under conditions allowing expression and secretion of protein by the host cell, and allowing under suitable conditions the aggregation of peptide monomers produced as a result of expression of exogenous DNA sequences within the host cell. A method of producing immunogenic particles is also disclosed which further comprises transfecting (cotransfection) the host cell with a DNA molecule encoding for a peptide including the amino acid sequence of the HBV S peptide. The cotransfection can occur before, after or simultaneous with the transfection of the above-described recombinant DNA molecule. Presence of peptides encoded by the cotransfected DNA molecule are necessary to obtain more than trace amounts of particles secreted from the host cell.

Methods of manufacturing a pharmaceutical preparation and a preparation useful for production of antibodies are disclosed comprising preparing an above-described recombinant DNA molecule, transfecting a host cell with the recombinant DNA molecule, culturing the host cell under conditions allowing expression and secretion of protein by the host cell, allowing under suitable conditions the aggregation of peptides produced as a result of expression of DNA sequences within the host cell to form immunogenic particles, and combining the immunogenic particles with a suitable carrier such that the immunogenic particles are present in sufficient concentration to cause production of antibodies upon administration of a preparation to an individual. Host cells used in these methods can also be cotransfected as previously described.

BRIEF DESCRIPTION OF THE FIGURES

FIGS. 1A–1C shows gene constructs encoding a polypeptide including the HBV pre-S1 region and a portion of the S region. The gene constructs also include the U2 promoter (FIG. 1A), the MT promoter (FIG. 1B) or the H2K promoter (FIG. 1C). The open boxes at the top of each figure signify inserts derived from the HBV genome, and the extent of deletions are indicated by the shaded segments thereof.

FIGS. 3A–3C shows gene constructs encoding a polypeptide including a portion of the HBV pre-S1 region, a portion of the pre-S2 region, and a portion of the S region. The gene constructs also include the U2 promoter (FIG. 3A), the MT promoter (FIG. 3B) or the H2K promoter (FIG. 3C). The open boxes at the top of each figure signify inserts derived from the HBV genome, and the extent of deletions are indicated by the shaded segments thereof FIGS. 4A–4C shows gene constructs encoding a polypeptide including at least a portion of the HBV pre-S1 region inserted within the S region at the XbaI site within S with a total deletion of the pre-S2 region. The gene constructs also include the U2 promoter (FIG. 4A), the MT promoter (FIG. 4B) or the H2K promoter (FIG. 4C). The open boxes at the top of each figure signify inserts derived from the HBV genome, and the extent of deletions are indicated by the shaded segments thereof.

FIGS. 6A–6C shows gene constructs encoding a polypeptide including a portion of the HBV pre-S1 region and the S region with deletion of the S ATG. The gene constructs also include the U2 promoter (FIG. 6A), the MT promoter (FIG. 6B) or the H2K promoter (FIG. 6C). The open boxes at the top of each figure signify inserts derived from the HBV genome, and the extent of deletions are indicated by the shaded segments thereof.

FIGS. 7A–7C shows gene constructs encoding a polypeptide including a portion of the HBV pre-S2 region and the S region with deletion of the S ATG. The gene constructs also include the U2 promoter (FIG. 7A), the MT promoter (FIG. 7B) or the H2K promoter (FIG. 7C). The open boxes at the top of each figure signify inserts derived from the HBV genome, and the extent of deletions are indicated by the shaded segments thereof.

FIGS. 9A–9B shows the nucleotide sequence of the pre-S1/pre-S2/S region of the HBV genome. Restriction sites (BglII, MstII, and XbaI) and start codons for pre-S1 protein ("S1"), pre-S2 protein ("S2"), and S protein ("S") are underlined.

FIGS. 10A–10B shows gene constructs encoding a polypeptide including at least a portion of the HBV pre-S2 region and the S region with deletion of the S ATG. The gene constructs also include the U2 promoter (FIG. 10A), the MT promoter (FIG. 10B) or the H2K promoter (FIG. 10C). The open boxes at the top of each figure signify inserts derived from the HBV genome, and the extent of deletions are indicated by the shaded segments thereof.

FIG. 15 shows the nucleotide sequence that encodes the HBV pre-S2 region and a portion of the S region, found in the gene construct of FIG. 10B.

FIG. 16 shows the amino acid sequences of pre-S polypeptides from HBV subtypes ayw, adyw, adw2, adw, and adr, from which pre-S1 epitopes of the invention can be derived.

FIG. 17 shows the nucleotide and amino acid sequences of the pre-S1 region from HBV subtype adr.

FIG. 18 shows the nucleotide and amino acid sequences of the pre-S1 region from HBV subtype ayw.

FIG. 19 shows the nucleotide and amino acid sequences of the pre-S1 region from HBV subtype adw2.

FIG. 20 shows the nucleotide and amino acid sequences of the pre-S1 region from HBV subtype adw.

DESCRIPTION OF THE PREFERRED EMBODIMENTS

Figure 1B:
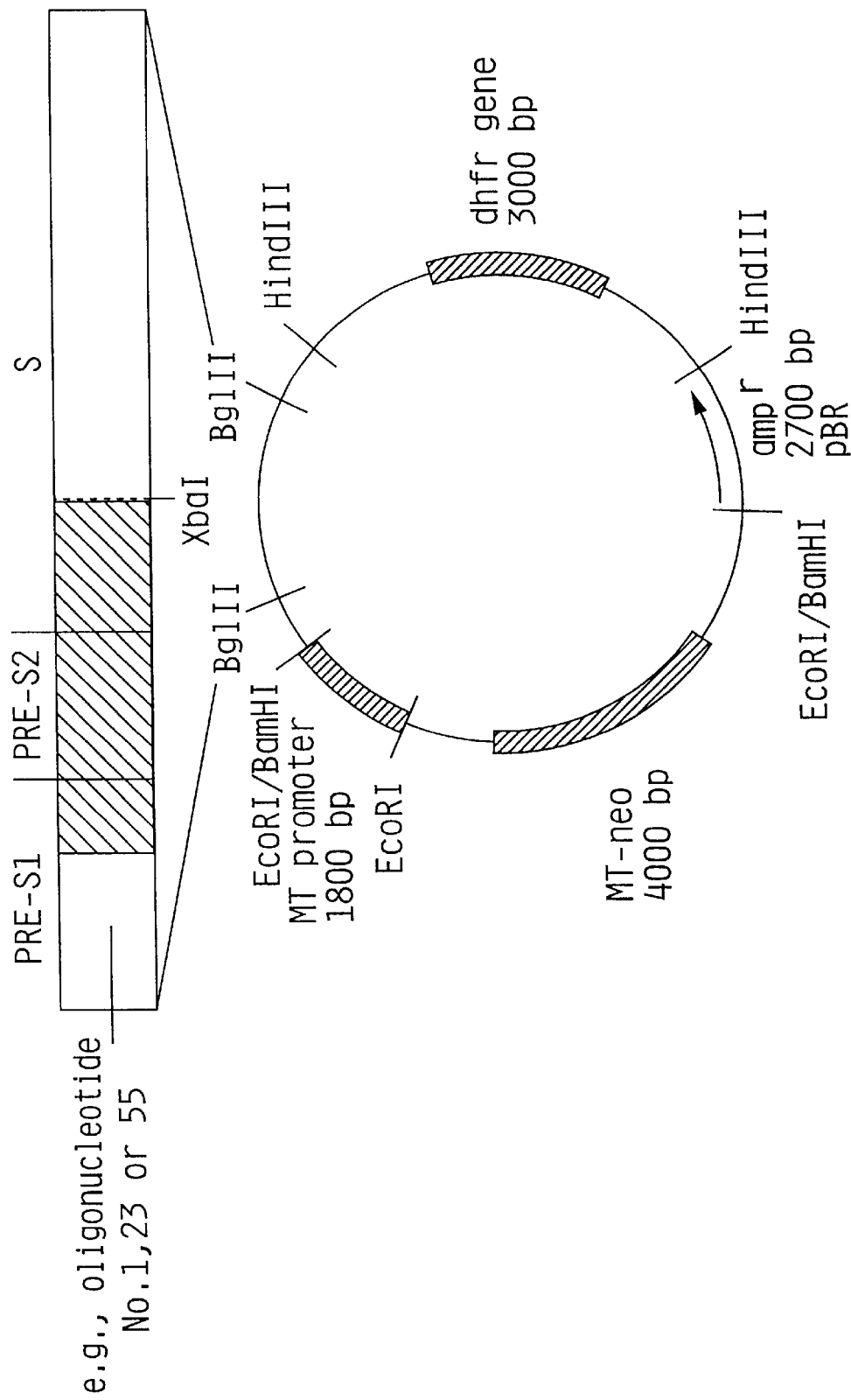
Figure 1C:
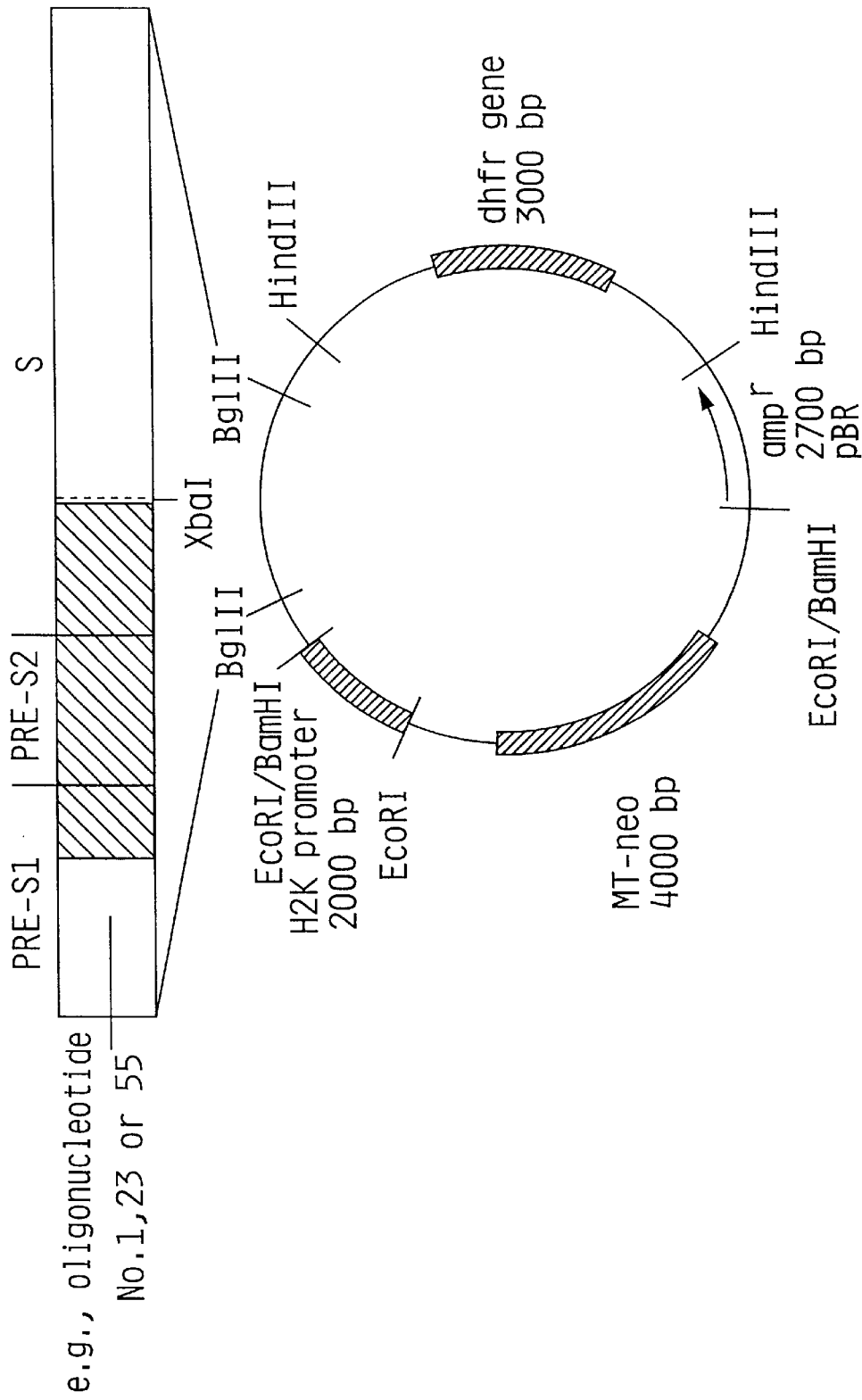
Figure 2A:
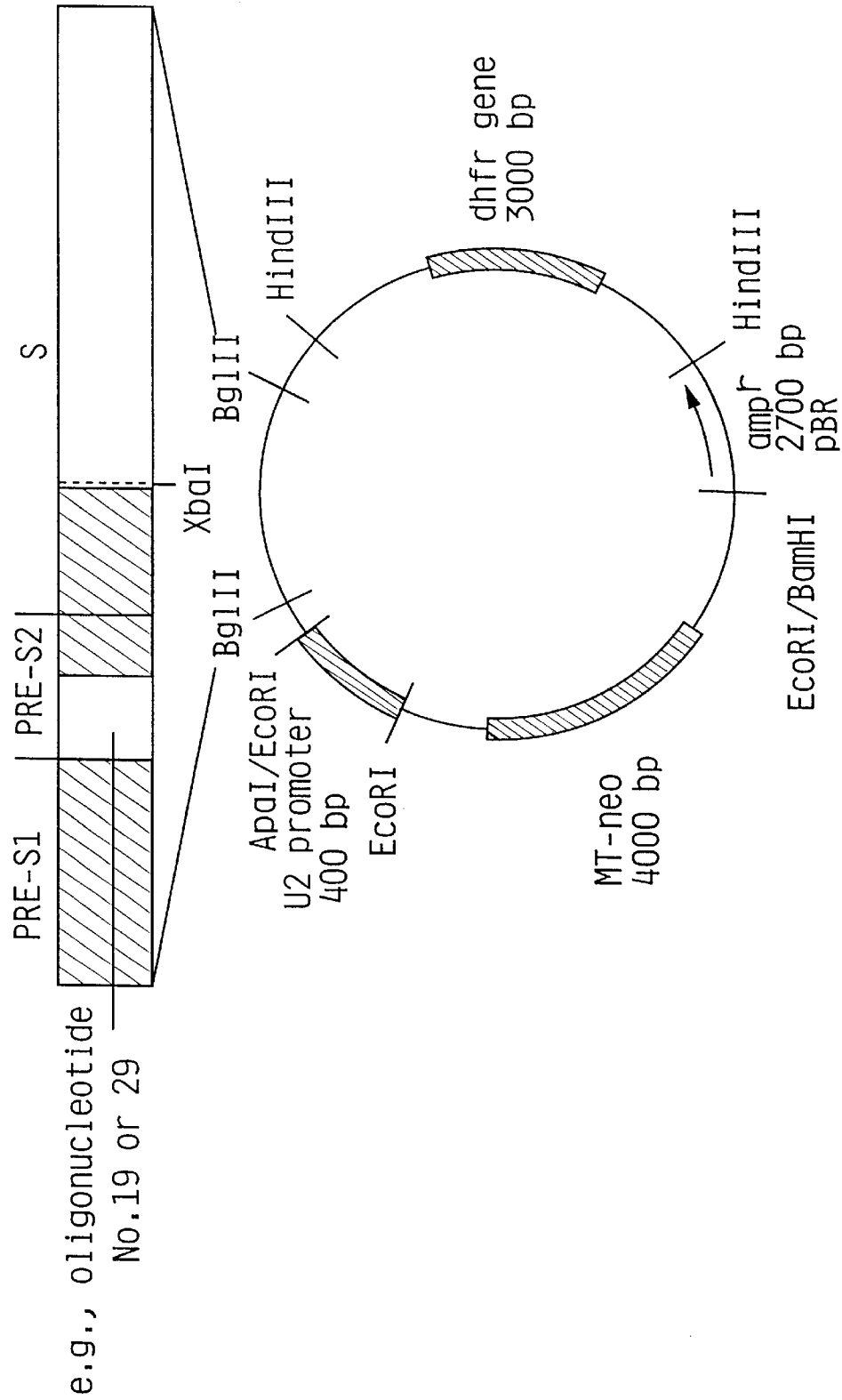
FIGS. 2A–2C shows gene constructs encoding a polypeptide including a portion of the HBV pre-S2 region and a portion of the S region. The gene constructs also include the U2 promoter (FIG. 2A), the MT promoter (FIG. 2B) or the H2K promoter (FIG. 2C). The open boxes at the top of each figure signify inserts derived from the HBV genome, and the extent of deletions are indicated by the shaded segments thereof.
Figure 2B:
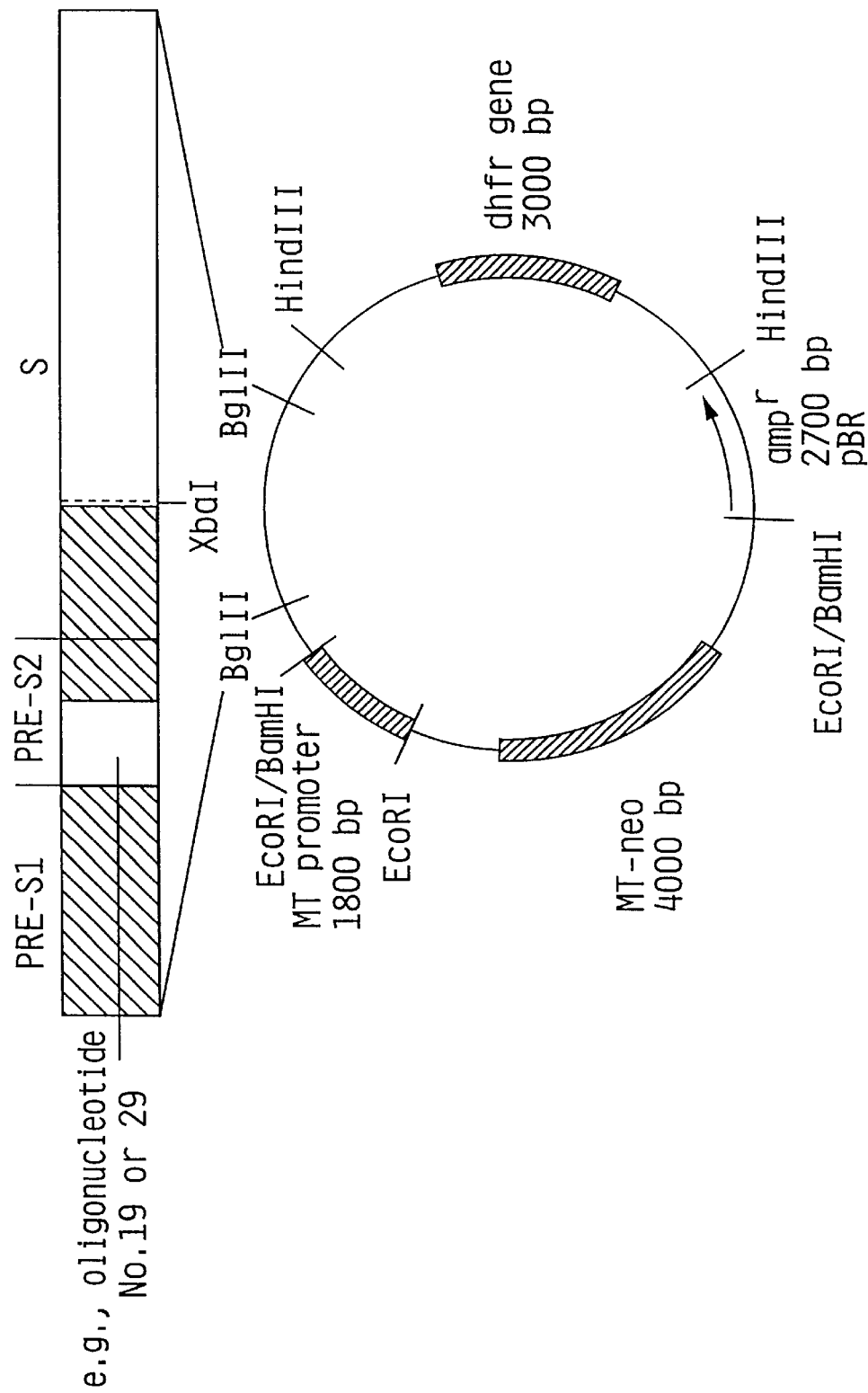
Figure 2C:
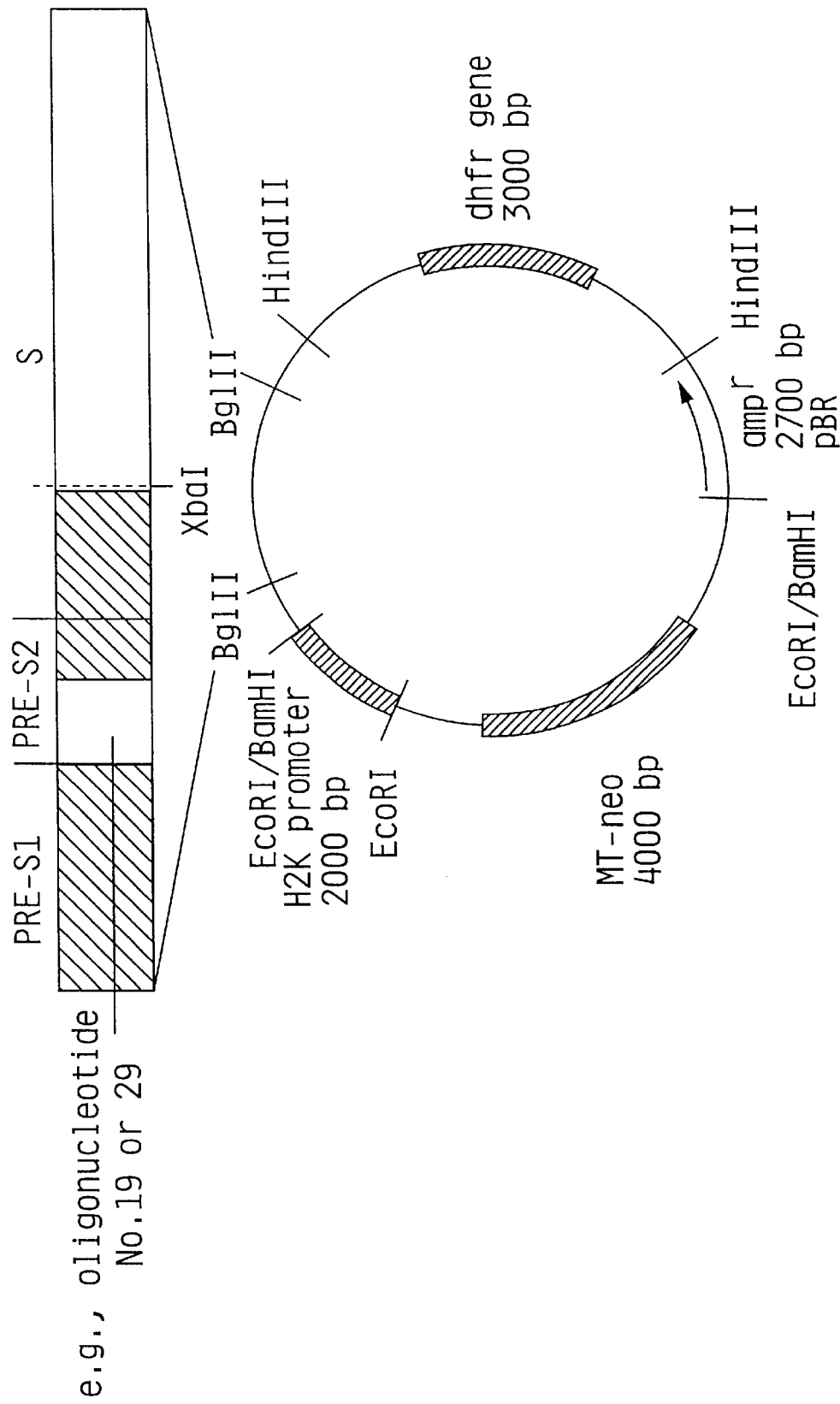
Figure 4A:
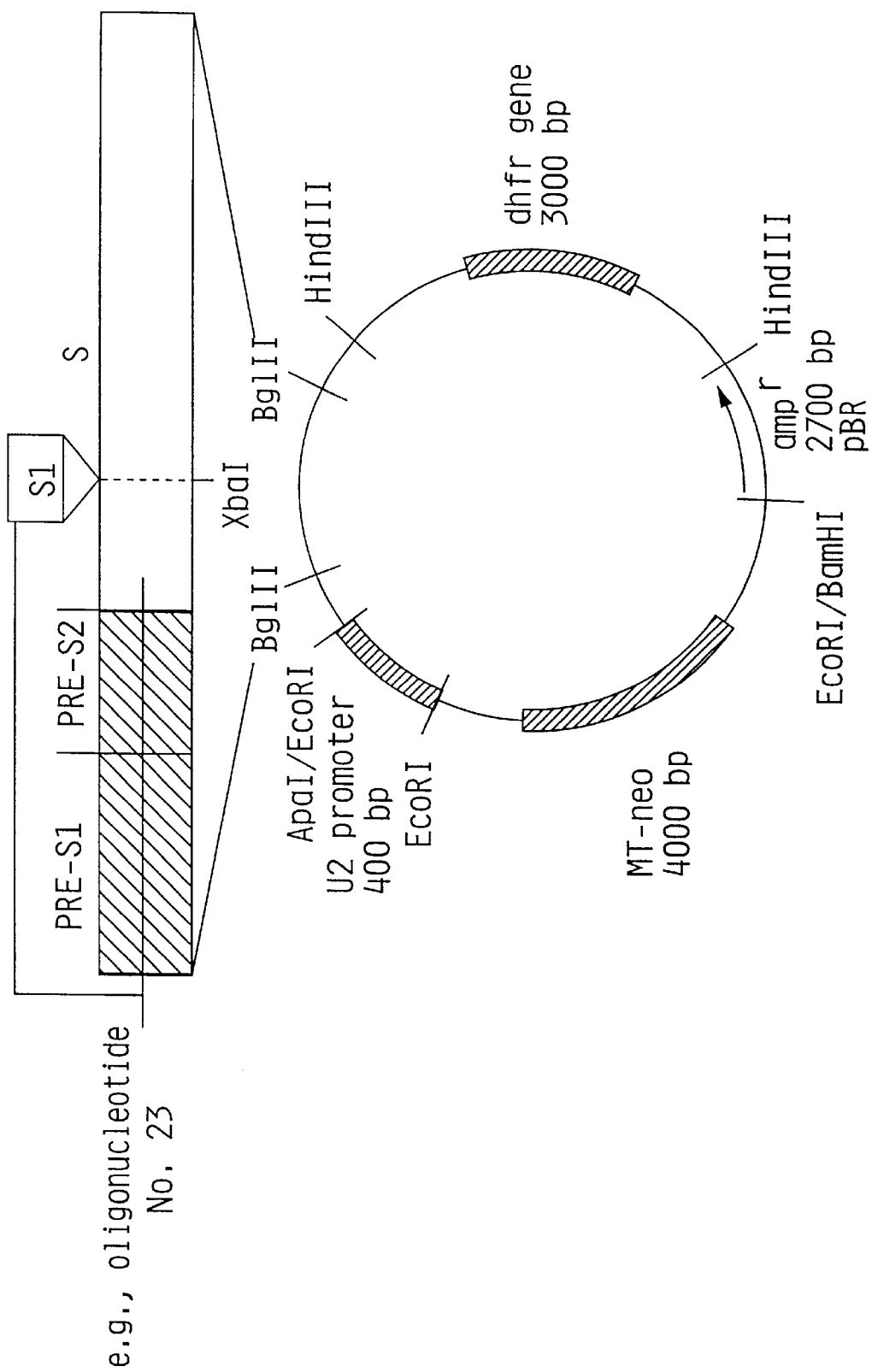
Figure 4B:
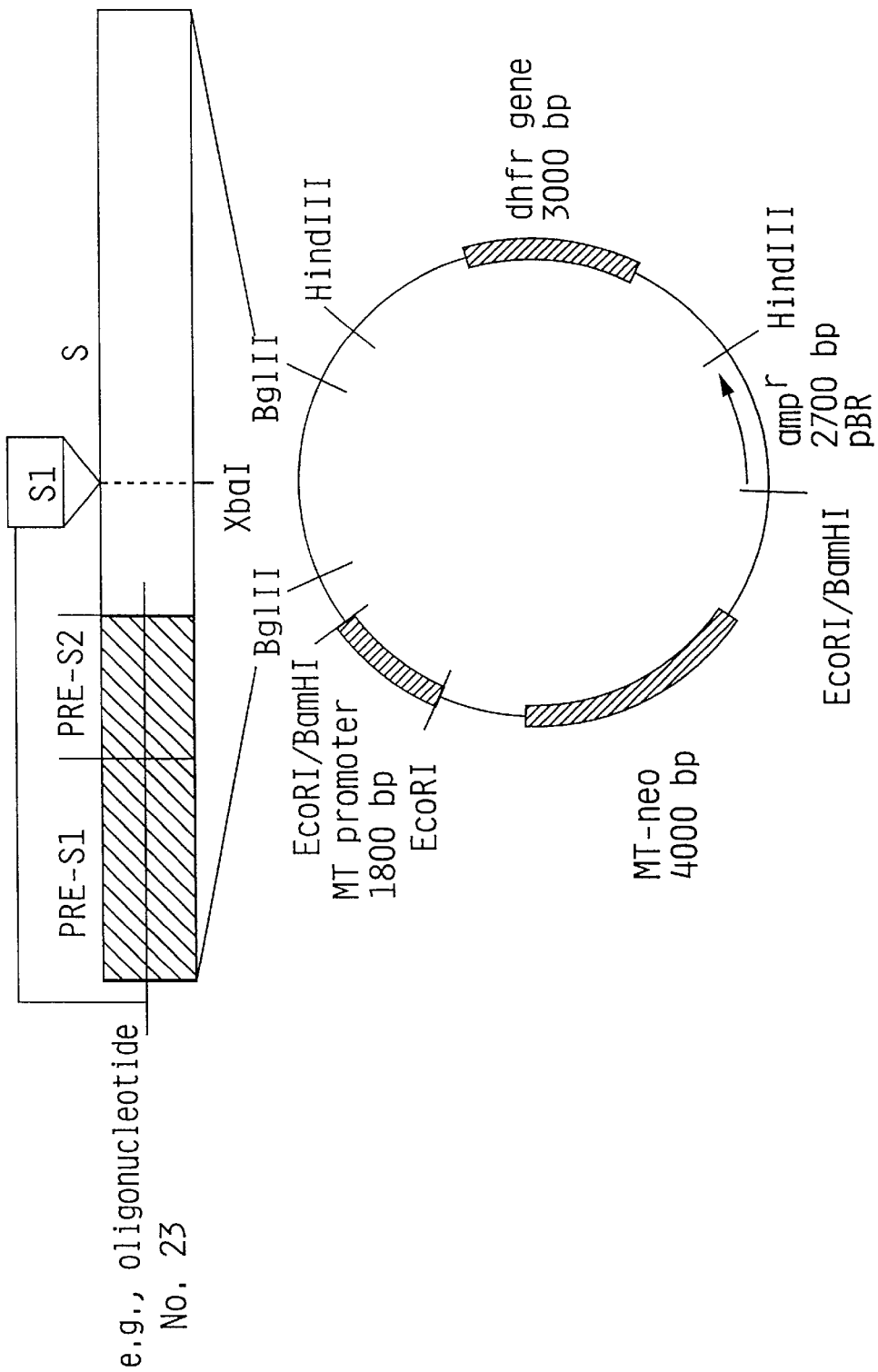
Figure 5A:
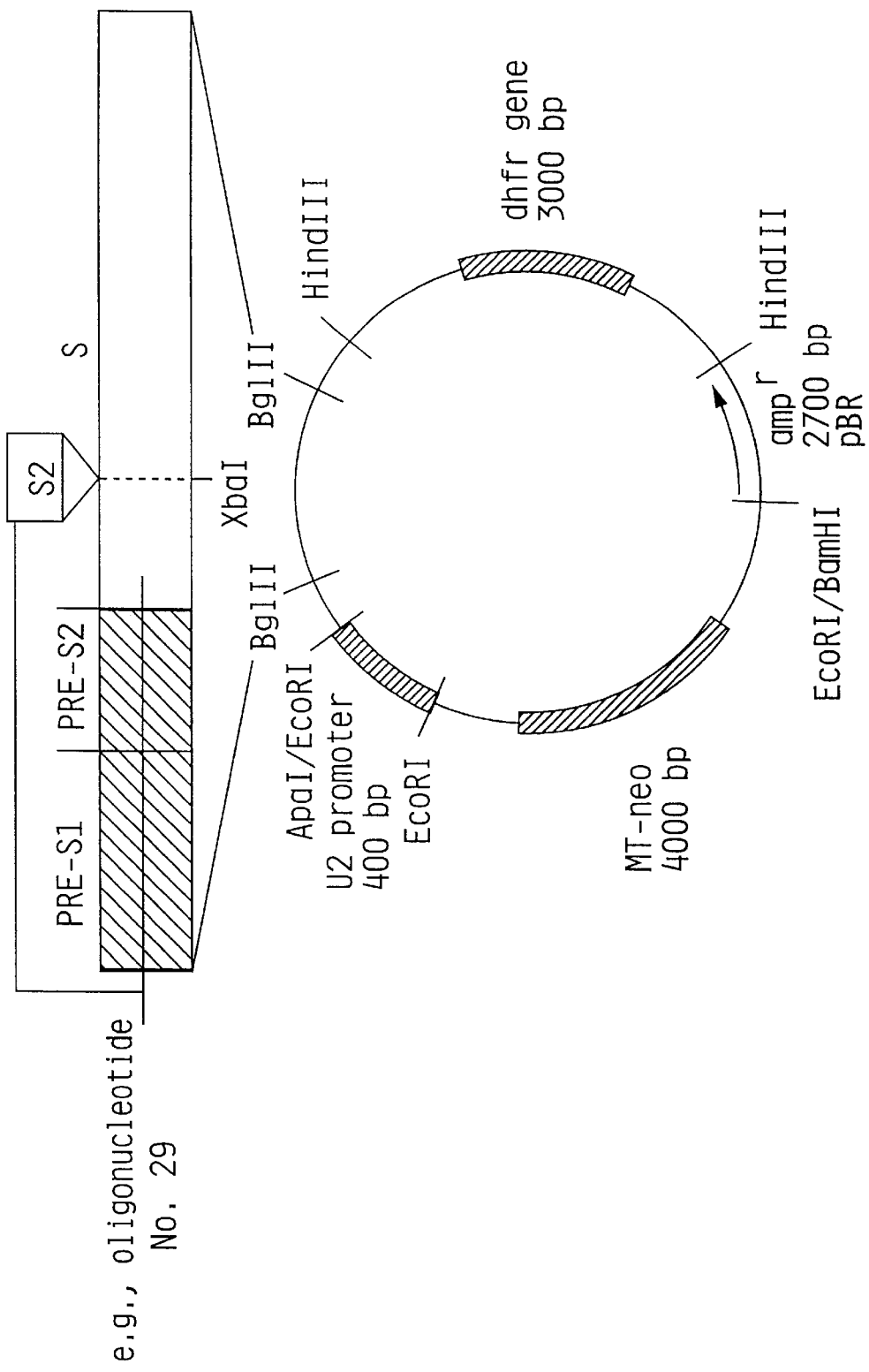
FIGS. 5A–5C shows gene constructs encoding a polypeptide including at least a portion of the HBV pre-S2 region inserted within the S region at the XbaI site within S with a total deletion of the pre-S1 region. The gene constructs also include the U2 promoter (FIG. 5A), the MT promoter (FIG. 5B) or the H2K promoter (FIG. 5C). The open boxes at the top of each figure signify inserts derived from the HBV genome, and the extent of deletions are indicated by the shaded segments thereof
Figure 5B:
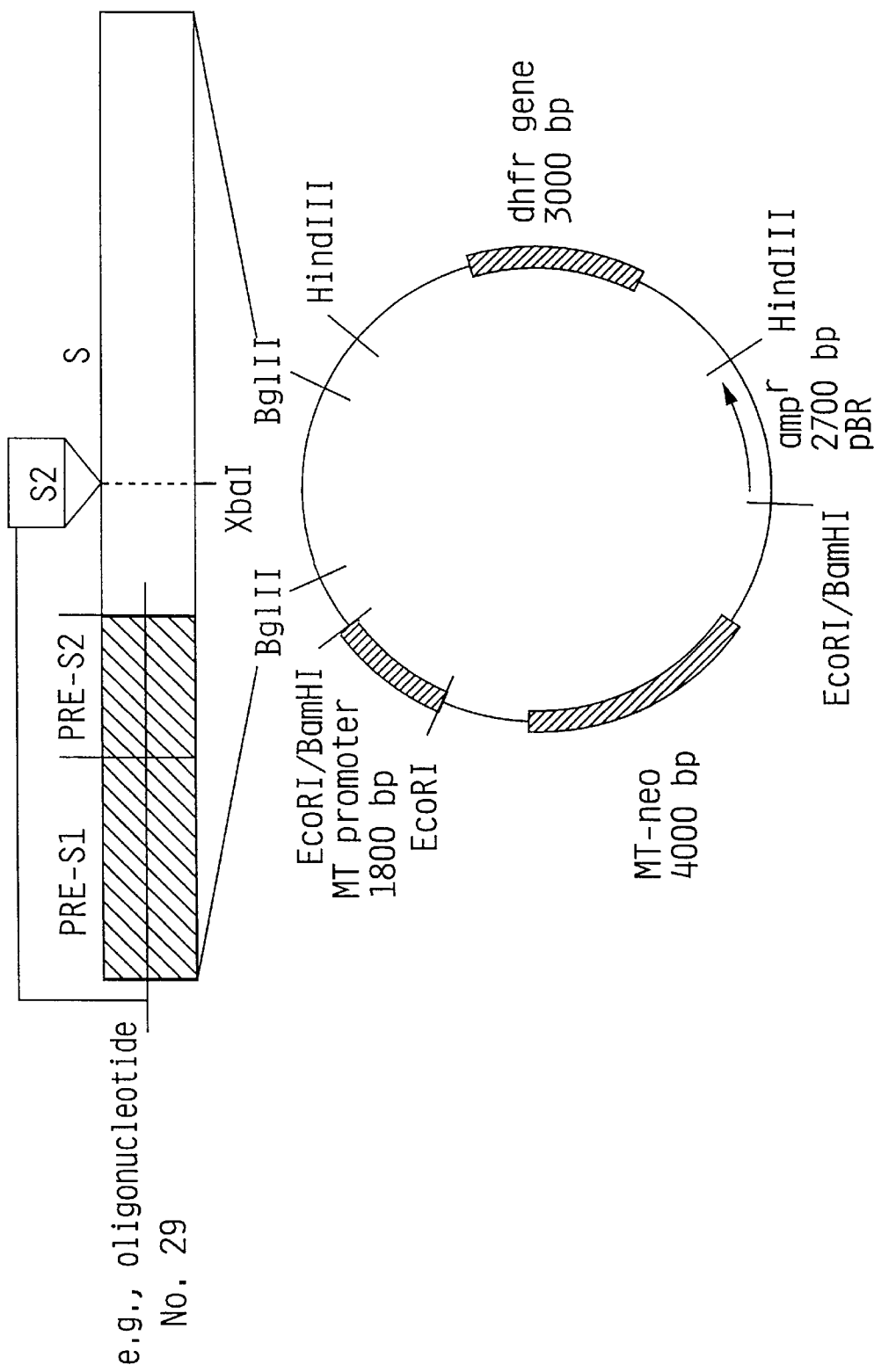
Figure 5C:
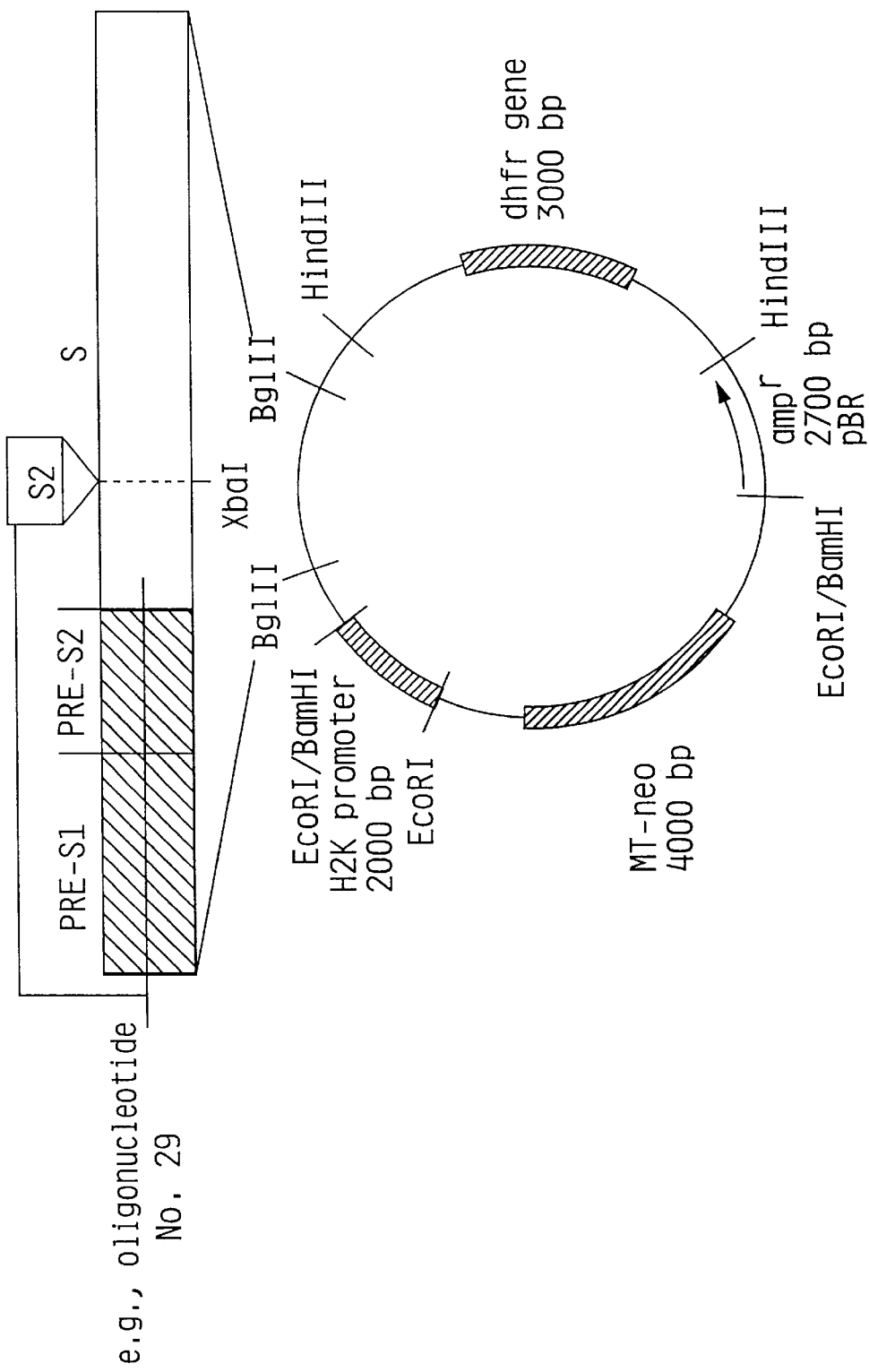
Figure 6A:
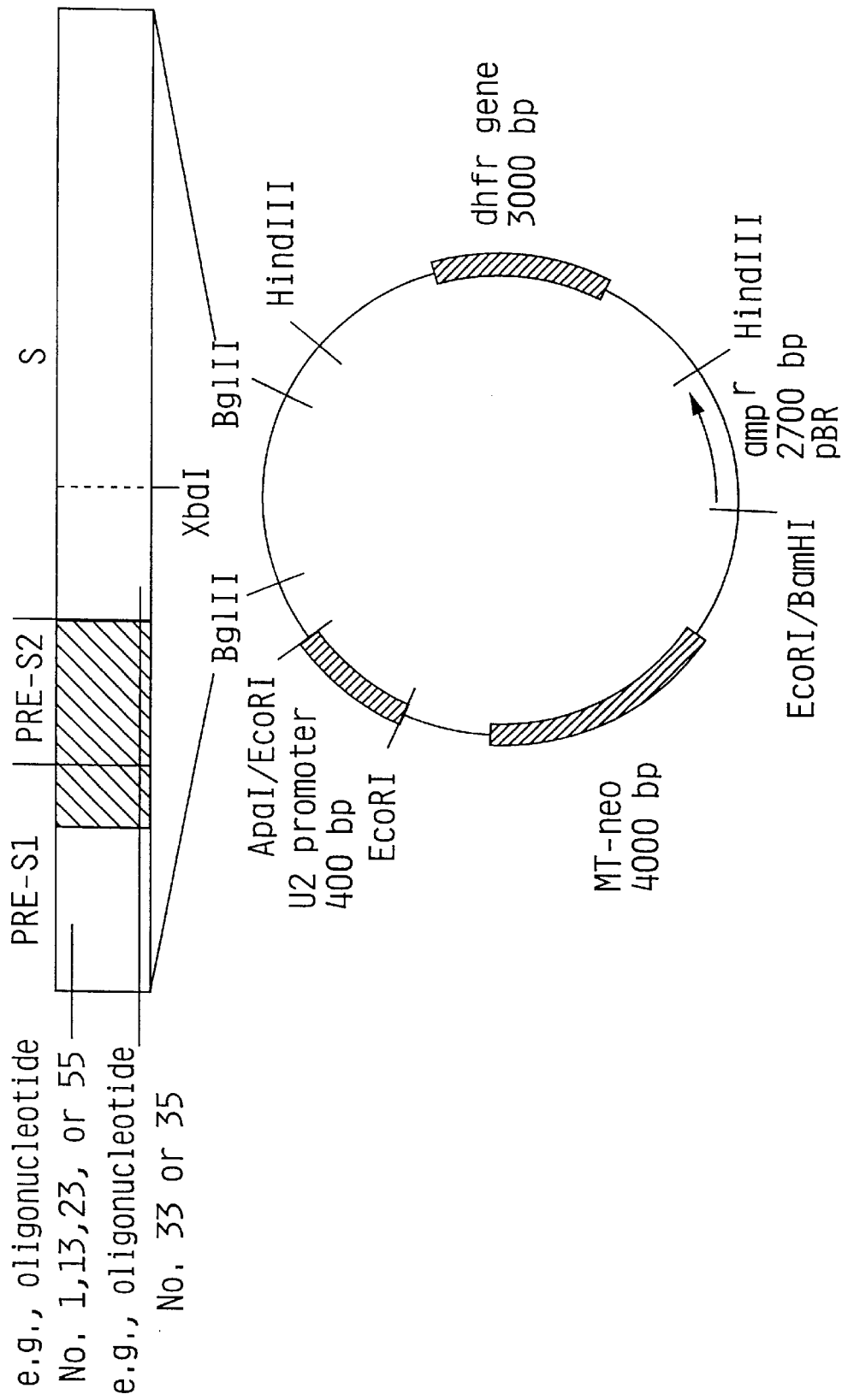
Figure 7A:
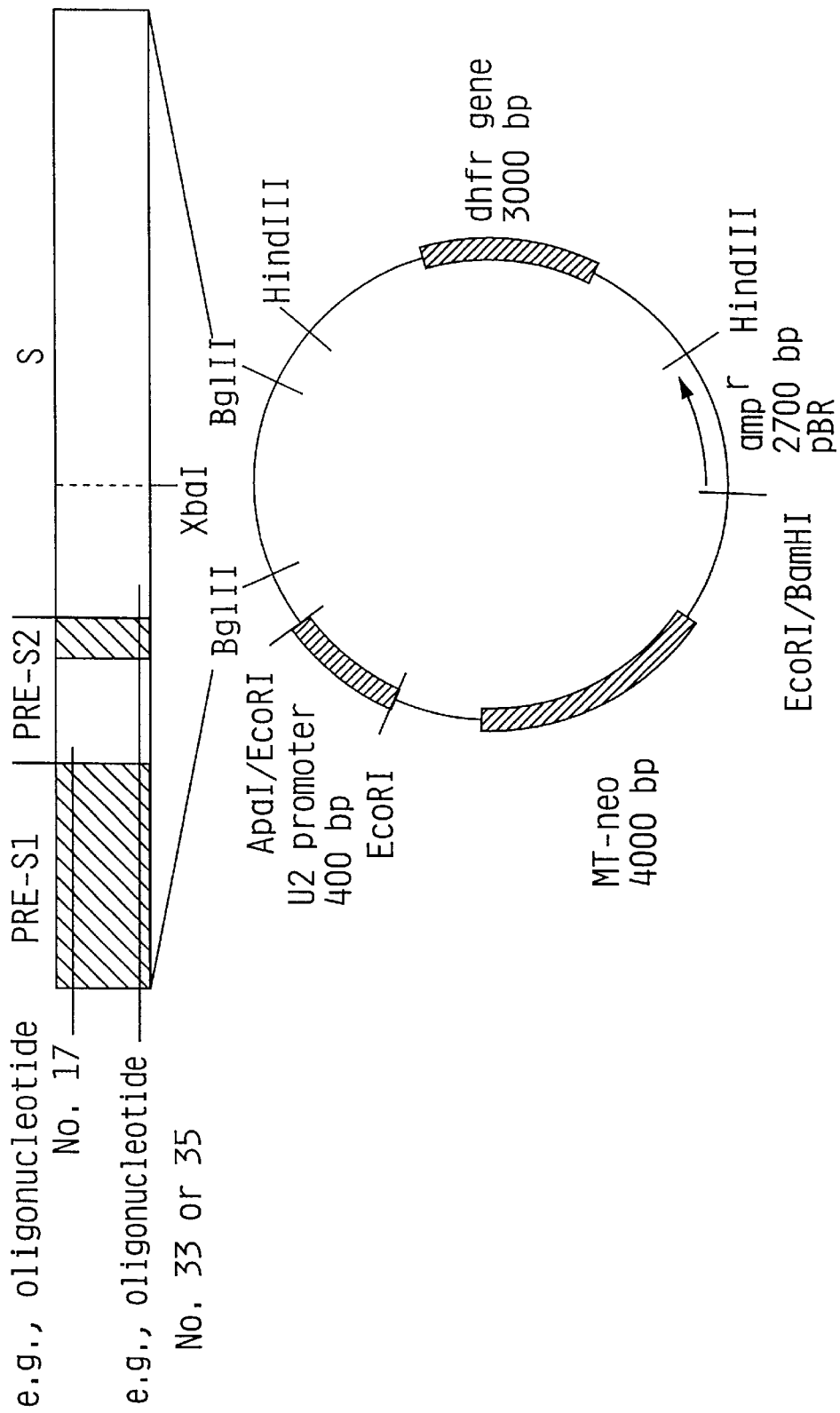
Figure 7C:
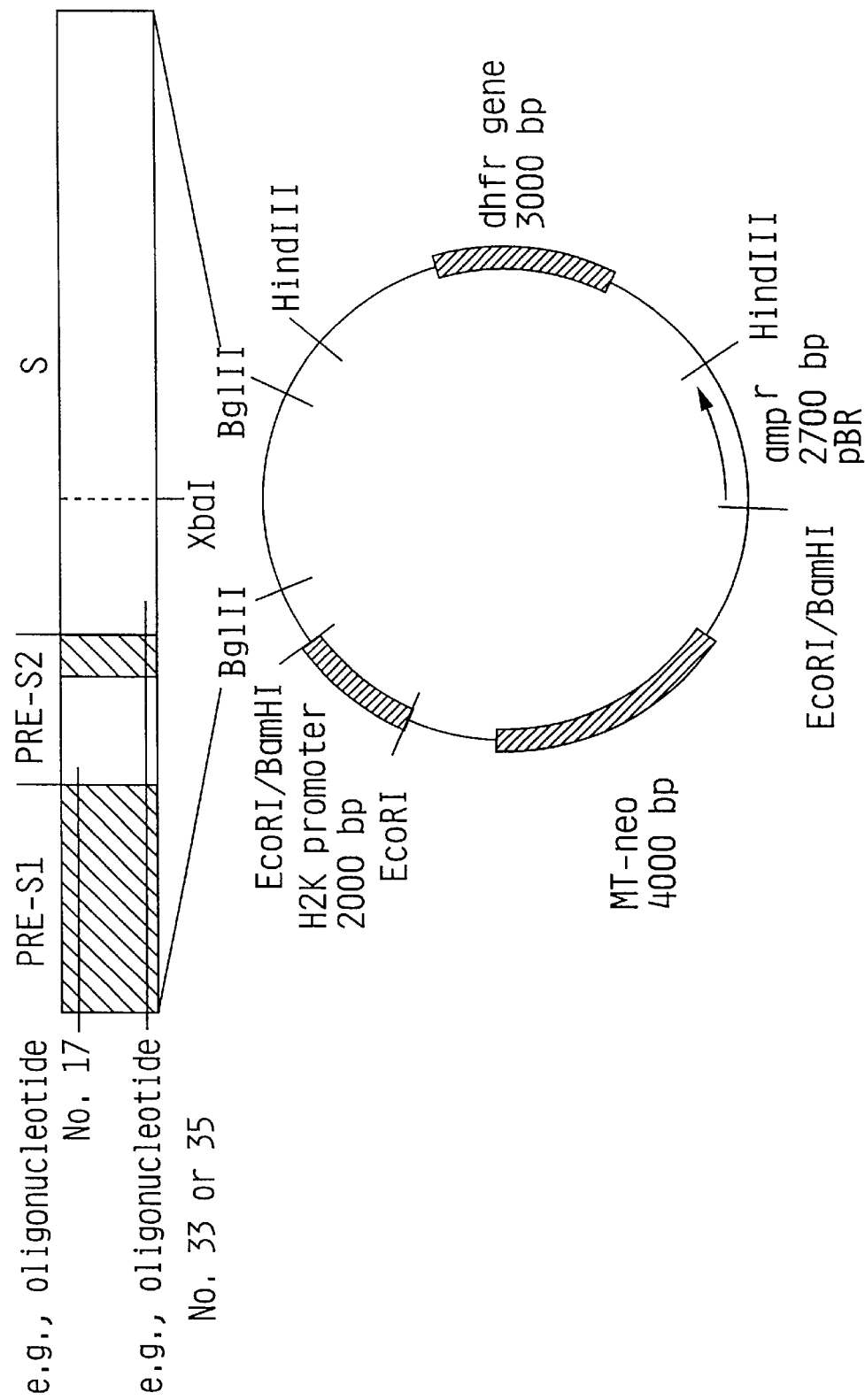
Figure 8A:
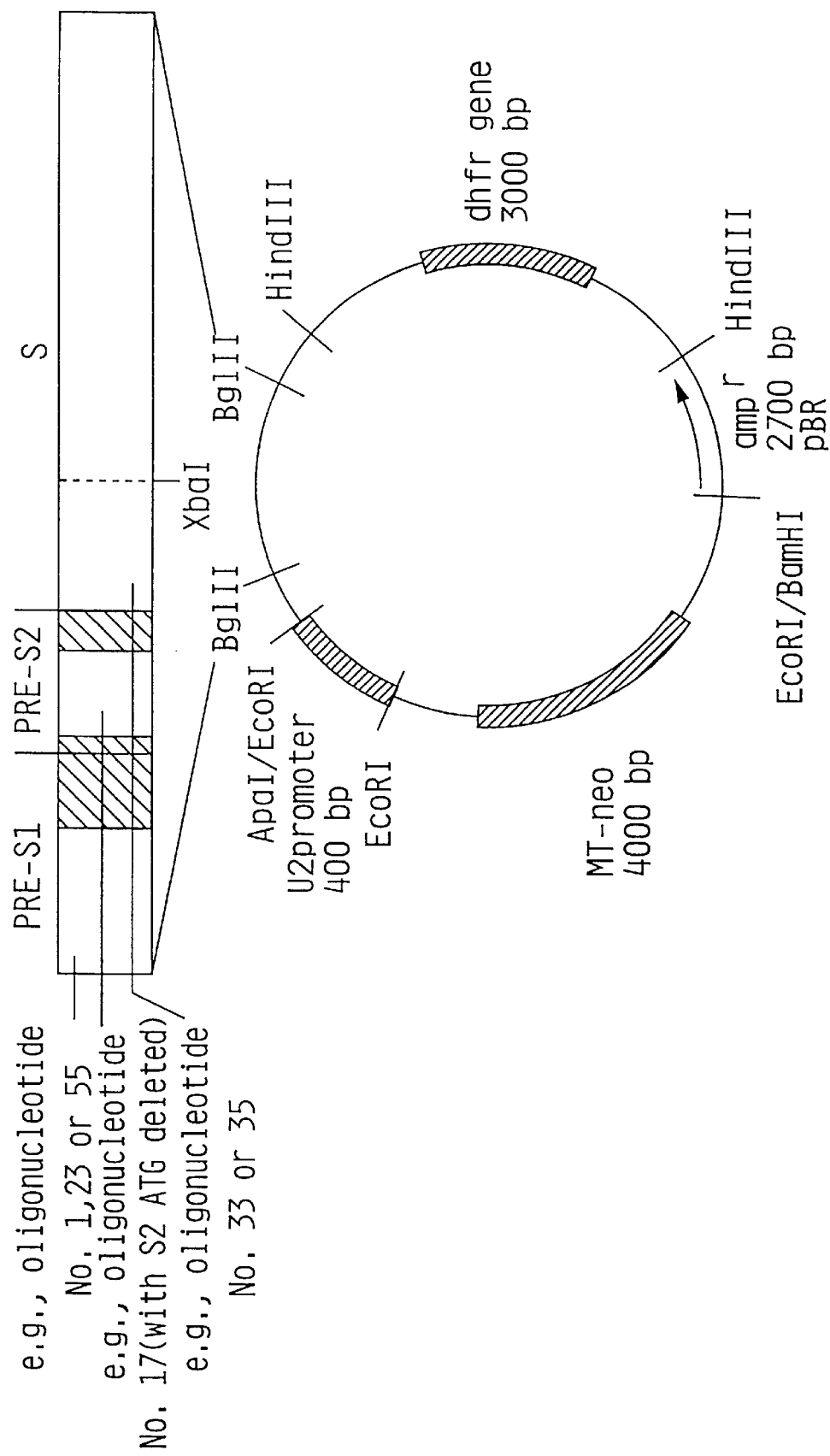
FIGS. 8A–8C shows gene constructs encoding a polypeptide including a portion of the HBV pre-S1 region, a portion of the pre-S2 region, and the S region with deletion of the S ATG. The gene constructs also include the U2 promoter (FIG. 8A), the MT promoter (FIG. 8B) or the H2K promoter (FIG. 8C). The open boxes at the top of each figure signify inserts derived from the HBV genome, and the extent of deletions are indicated by the shaded segments thereof.
Figure 8B:
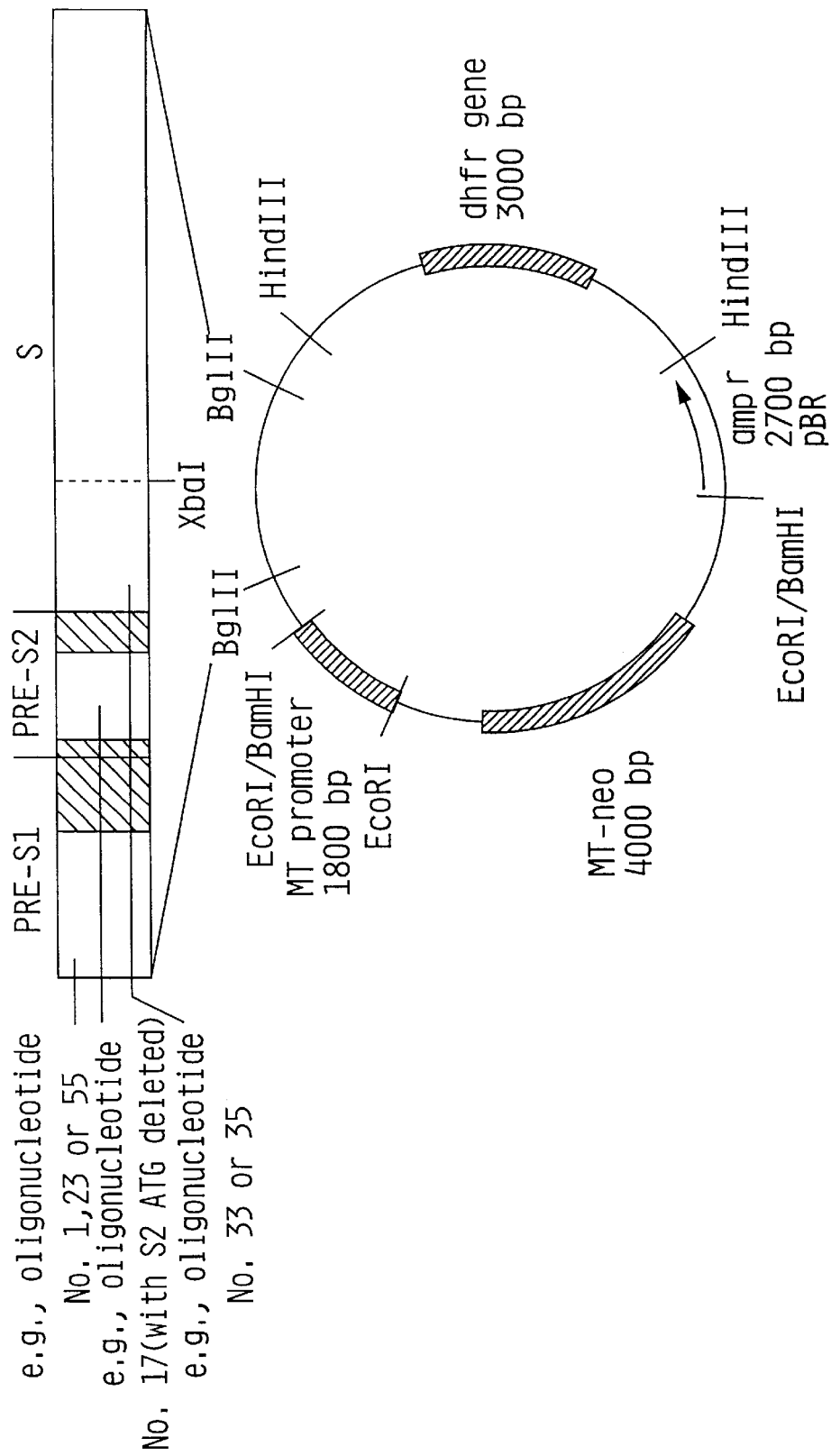
Figure 8C:
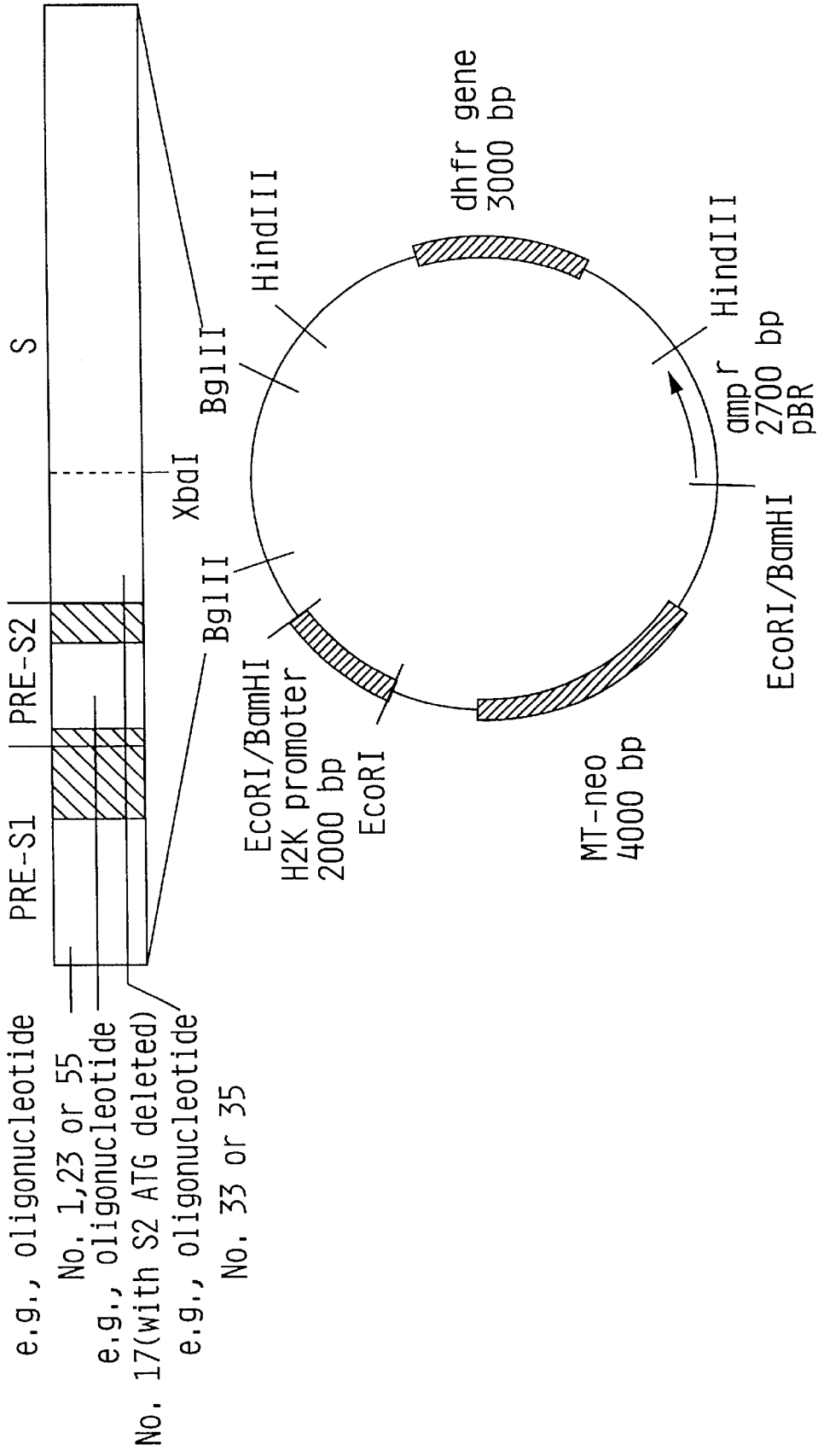

Preferred DNA constructs of the present invention are characterized by the presence of a selection marker selected from the group consisting of dhfr (dihydrofolate reductase), MT-neo (a neomycin resistance sequence coupled to a methallothionein and MT-ecogpt (a resistance-sequence coupled to a methallothionein promoter). The expression rate may be further enhanced by adding to the constructs a dhfr gene as an amplification gene.

HBV nucleotide sequences used in certain constructs of the present invention can be formed or isolated by any means including isolation and ligation of restriction fragments and synthetic oligonucleotides. Constructs specifically described herein were formed by the ligation of synthetic oligonucleotides to a 5' XbaI-BqlII 3' fragment from the S region of the HBV genome shown in Figure IX (hereinafter the "Xbal-BglII fragment") which in derived from a BglII-BglrII HBV fragment including the entire pre-S$_1$-pre-S$_2$-S regions (the "BglI-Bg Fragment"). The pre-S$_1$-pre-S$_2$-S region of the HBV genome is shown in FIG. 9. Oligonucleotides used in making such constructs are summarized in Table I.

TABLE I

Oligonucleotide Duplexes for Vector Construction

| Oligo. No. | Restriction Sites and Schematic Structure | Function | Sequence (5'–3') (sticky ends are underlined) |
|---|---|---|---|
| 1 | MstII-ATG-S1-XbaI | S1 (exchanged flanking sequence ATG) | <u>TCAGG</u>AAATGGAGAACATATCAGGA TTCCTAGGACCCCTTCTCGTGTTACAG GCGGGGTTTTTCTTGTTGACAAGAATC CTCACAATACCGCAGAGT |
| 13 | MstII-ATA-S1-XbaI | S1 (exchanged flanking sequence ATA) | <u>TCAGG</u>AAATAGAGAACATATCAGGA TTCCTAGGACCCCTTCTCGTGTTACAGG CGGGGTTTTTCTTGTTGACAAGAATCCT CACAATACCGCAGAGT |
| 17 | BglII-ATG-S2-EcoRI | S2 (exchanged flanking sequence ATG) | <u>GATC</u>TACCTGAACATGGAGTGG |
| 19 | MstII-ATG(S)-S2-XhoI | S2 (20 amino acids; with S ATG) | <u>TCAGG</u>CGCTGAACATGGAGAACATCTCC AGTTCAGGAACAGTAAACCCTGTTCTGA CTACTGCCTCTCCCTTATCGTCAATCTTC |
| 23 | BglII-ATG(S)-S1-XbaI | S1 (28 amino acids; with S ATG) | <u>GATC</u>TTTAACATGGAGAACAATCCTCTG GGATTCTTTCCCGATCACCAGTTGGATCC AGCCTTCAGAGCAAACACCGCAAATCC AGATTGGGACTTCAATCCCAGT |
| 29 | BglII-ATG(S)-S2-XbaI | S2 (26 amino acids; with S ATG) | <u>GATC</u>TTTAACATGGAGAACCAGTGGAAT TCCACAACCTTCCACCAAACTCTGCAAG ATCCCAGAGTGAGAGGCCTGTATTTCCCT GCTGGTGGCTCCAGT |
| 33 | XbaI-ATA(S)-StyI | S 5' with ATA | <u>CTAG</u>ACCCTGCGCTGAACATAGAGAACA TCACATCAGGATTCCTAGGACCCCTTCTC GTGTTACAGGCGGGGTTTTTCTTGTTGACA AGAATCCTCACAATACCGCAGAGC |
| 35 | XbaI-ATA(S)-HpaI-StyI | S 5' with ATA | <u>CTAG</u>ACCCTGTGGTTAACATAGAGAACA TCACATCAGGATTCCTAGGACCCCTTCTC GTGTTACAGGCGGGGTTTTTCTTGTTGACA AGAATCCTCACAATACCGCAGAGC |
| 37 | BglII-S1-HpaI | S1 | <u>GATC</u>TTTAACATGGAGAACAATCCTCTG GGATTCTTTCCCGATCACCAGTTGGATCC AGCCTTCAGAGCAAACACCGCAAATCC AGATTGGGACTTCAATGTT |
| 39 | EcoRI-XbaI-XhoI-ATA(S)-StyI | S 5' with ATA | <u>AATT</u>CTAGACTCGAGTCTGAACATAGAG AACATCACATCAGGATTCCTAGGACCCC TTCTCGTGTTACAGGCGGGGTTTTCTTGT TGACAAGAATCCTCACAATACCGCAGA GC |
| 43 | StyI-S2-XhoI | S 3' | <u>CTAGG</u>AACAGTAAACCCTGTTCTGACTA CTGCCTCTCCCTTATCGTCAATCTTCTCTA GGATTGGGGAC |
| 45 | BglII-ATG(S)-S1-poly alanine-XbaI | S1 (17 amino acids; with S ATG); poly alanine sequence | <u>GATC</u>TTTAACATGGAGAACGATCACCAG TTGGATCCAGCCTCCAGAGCAAACACCG CAGCCGCCGCCGCCGCCGCCGCCGCCG CCGCCGCCGCCGCCAAT |
| 49 | XbaI-S2-StyI | S 3' | <u>CTAG</u>ACACAGTAAACCCTGTTCTGACTA CTGCCTCTCCCTTATCGTCAATCTTCTCGA GGATTGGGGAC |
| 55 | BglII-S1-XbaI | S1 (28 amino acids) | <u>GATC</u>TTTAACATGGAGACCAATCCTCTG GGATTCTTTCCCGATCACCAGTTGGATCC AGCCTTCAGAGCAAACACCGCAAATCC AGATTGGGACTTCAAT |

The oligonsotides in Table I were combined with the xbaI-BglII fragment to produce constructs with desired features. In certain constructs adapter oligonucleotide sequences (Table II) were used to create proper matching sticky ends on the oligonucleotides and other construct components.

TABLE II

Oligonucleotide Duplexes (Adapter Sequences)

| Oligo. No. | Restriction Sites and Schematic Structure | Sequence (5'-3') |
|---|---|---|
| 2 | ApaI-BglII-HindIII | CTTAGATCTTTA CCGGGAATCTAGAAATTCGA |
| 4 | MstII-XhoI | TCAGGAC CCTCAGCT |

TABLE II-continued

Oligonucleotide Duplexes (Adapter Sequences)

| Oligo. No. | Restriction Sites and Schematic Structure | Sequence (5'-3') |
|---|---|---|
| 7 | EcoRI-HindIII-BglII | AATTCAAGCTTA<br>GTTCGAATCTAG |
| 9 | SalI-BglII-BamHI | TCGACAGATATG<br>GTCTAGACCTAC |
| 15 | EcoRI-BglII | AATTCCCCGGGA<br>GGGGCCCTCTAG |
| 27 | EcoRI-BglII-BnamHI-HindIII | AATTCAGATCTGGATCCGAGCTCA<br>GTCTAGACCTAGGCTCGAGTTCGA |
| 31 | BamHI-HindIII | GATCCTTA<br>GAATTCGA |
| 41 | ApaI-BglII-XhoI | CAAAAGATCT T TTC<br>CCGGGT TT TCTAGAAAAGAGCT |
| 47 | XbaI-polyalanine-XhoI | CTAGAC(2OH GCC)GAC<br>TG(2OH CGG)CTGAGCT |
| 53 | EcoRI-BglII-XbaI-XhoI | AAT TCATCCAGATCTAATTCTC TAGATTAC<br>GTAGGTCTAGATTAAGAGATCTAATGAGCT |
| 57 | XhoI-XbaI | TCGAGGAGTCGACCTAGT<br>CCTCAGCTGGATCAGATC |
| 61 | BglII-EcoRI-BglII | GATCTAATTGAATTCAATTA<br>ATTAACTTAAGTTAATCTAG |
| 63 | EcoRI-SalI-EcoRI | AATTATGTCGACTA<br>TACAGCTGATTTAA |

Other adaptor sequences may be used to combine desired oligonucleotides from Table I with the XbaI-BglII fragment, other restriction fragments, oligonucleotides and other construct components. The necessary sequences of such other adapter sequences will be readily apparent to those skilled in the art from consideration of tables of restriction sites [e.g., that found at pages 121–128 of *Methods in Enzymology*, volume 152, "Guide to Molecular Cloning Techniques," ad. Borger and Kimmel (Academic Press 1987) which is incorporated herein in its entirety by reference] and the sequences of the various nucleotides to be combined. Adapter sequences can also be used to introduce additional restriction sites into constructs of the present invention. It should be noted that adapter sequences must be selected or designed so that the proper reading frame is maintained throughout the HBV sequence.

Preferred gene constructs which were used to transfect host cells were prepared by recombinant DNA techniques in accordance with the present invention. Preferred embodiments of constructs with an enhanced expression rate are shown in Figures I-VIII and are schematically represented by the following:

pU2-structural gene pU2-structural gene-dhfr pU2-structural gene-dhfr-MT-neo pU2-structural gene-dhfr-MT-egpt pMT-structural gene-dhfr pMt-structural gene-dhfr-MT-neo pMT-structural gene-dhfr-MT-egpt pH2K-structural gene-dhfr pH2K-structural gene-MT-neo pH2K-structural gene-MT-egpt pH2K-structural gene-dhfr-MT-neo pH2K-structural gene-dhfr-MT-egpt Each of the constructs shown in Figures I-VIII contain, in addition to a HBV sequence, a neomycin selection marker with the MT promoter, an ampicillin selection marker, a dhfr selection/amplification gene and a promoter for the HBV sequence. The promoter for the HBV sequence is preferably the U2 promoter, the MT promoter or the H2K promoter. Isolation of fragments containing the various promoters, the selection markers and amplification gene is described below. The HBV sequences in the constructs of FIG. 1–8 are schematically represented by a rectangular bar in each figure which indicates the oligonucleotides and/or adapter sequences from Tables I and II which were combined with the XbaI-BglII fragment. Shaded areas within the bar indicated generally regions of the entire pre-$S_1$-pre-$S_2$-S region which are not found in the specific construct. Oligonucleotides from Table I which can be used to construct each type of HBV sequence are indicated in the figures.

Figure 10A:
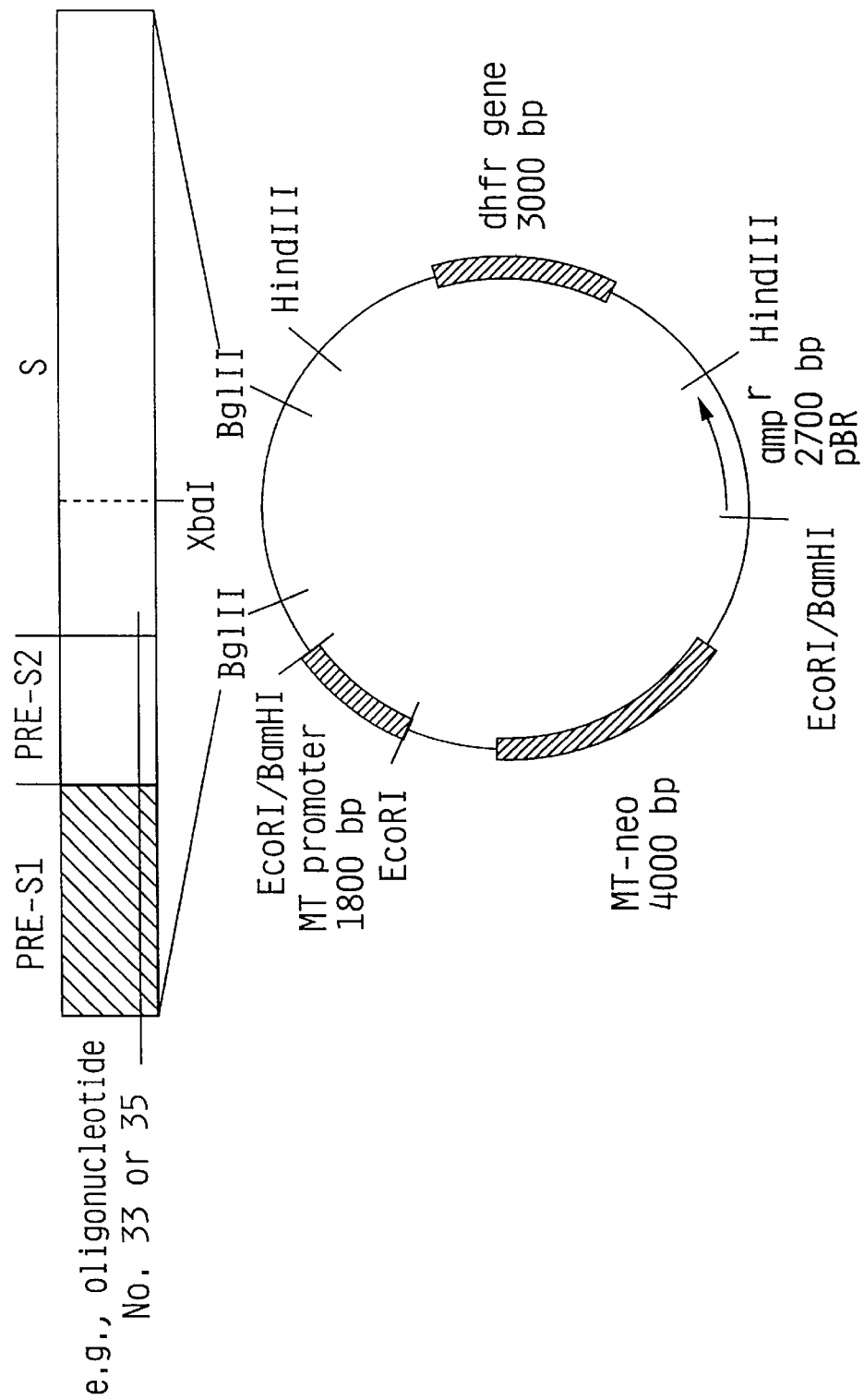

FIG. 10 depicts two additional constructs for expression of peptides including sequence from the pre-S2 region under the control of the MT promoter.

Constructs have also been made which include the entire BglII-BglII fragment from the HBV genome under the control of the US promoter. These constructs have produced peptides which include a deletion in the S region as indicated by Western blot analysis.

The above-cited promoters are specially preferable when their use is coupled with a modulation method using the dhfr gene and methotrexate to enhance the expression. This is achieved when in addition to the selection marker the dhfr minigene is also introduced into the plasmid sequence. It is essential that the dhfr gene is located on the same plasmid together with the structural gene to be expressed. An enhancement of the expression rate of the structural gene can then be obtained by adding methotrexate in the micromolar concentration range. Thereby a manyfold enhancement of the expression rate is achieved.

Suitable cells are e.g. VERO cells (monkey kidney cell line), 3T3-cells (murine fibroblast line), C127-cells (murine fibroblast line), L-cells and CHO—cells (Chinese hamster cells, which are either positive or negative in dehydrofolate reductase).

As a stop signal it is preferred to use a stop signal from a eukaryotic cell. Preferably the stop signal of the caseine DNA-sequence is used. As used throughout the following examples, "HBV protein" refers generically to any protein produced in accordance with the present invention which corresponds to HBsAg sequences.

EXAMPLE 1

Particle Purification Procedures

1. Fractionated Precipitation with Polyethylene Glycol (PEG)

The supernatant of HBV protein producing cultures was collected and split into portions of 2,400 ml. To each portion 144 g of PEG 6000 (Serva) were added and dissolved by stirring at room temperature for 20 minutes and was stirred for another 6 hours at 4° C. The precipitate was separated by centrifugation in 500 ml bottles an a GS 3 rotor at 9.000 rpm (15,000×g) for 30 minutes at 10° C. The supernatant was collected and 144 g of PEG 6000 were added and dissolved as described above. The solution was stirred at 4° C. for 3 hours. The precipitate from this solution was harvested as described above except that centrifugation was continued for 60 minutes.

2. Gel Chromatography

The material obtained after PEG precipitation was redissolved in 20 ml PBS and submitted to gel chromatography on A-5m (BioRad). Column dimensions were 25×1000 mm and 480 ml bed volume. In a typical fractionation run 1,000 ug of PEG precipitated HBV protein in 10 to 15 ml was loaded and eluted with PBS at a speed of 6 drops/min (18 ml/h) 3 ml fractions were collected. HBV protein eluted with the first peak. Collected fractions were submitted to a CsCl gradient.

3. Sedimentation in CsCl Gradient

About 30 fractions covering the first peak in column chromatography on A-5m and containing prepurified HBV protein were collected to approximately 100 ml. This solution was adjusted to a density of 1.30 g/cc with CsCl and subsequently transferred to a nitrocellulose tube fitting into a SW 27/28 rotor (Beckman). A gradient was set by underlaying 4 ml of a CsCl solution of 1.35 g/cc and by overlaying 4 ml of 1.25 g/cc followed by 4 ml of 1.20 g/cc density. This gradient had been run at 28,000 rpm for 50 hours at 10° C. Thereafter the gradient was fractionated and purified HBV protein floating in the 1.20 q/cc density layer was collected. The solution was desalted by three cycles of dialysis in bags against water.

EXAMPLE 2

Quantitative Determination of HBV Protein

1. With Radioimmunoassay

In the AUSRIA II-125 "sandwich" radioimmunoessay (commercially available from Abbot), beads coated with guinea pig antibody to Hepatitis B Surface Antigen (Anti-HBs) were incubated with serum or plasma or purified protein and appropriate controls. Any HBsAg present was bound to the solid phase antibody. After aspiration of the unbound material and washing of the bead, human 125T-Anti-HBs was allowed to react with the antibody-antigen complex on the bead. The beads were then washed to remove unbound $^{125}$I-Anti-HBs.

)-Anti-HBs HBsAg

)-Anti-HBs . HBsAg 125I-Anti-HBs

)-Anti-HBs . HBsAg . 125-Anti-HBs

The radioactivity remaining on the beads was counted in a gamma scintillation counter.

2. With ELISA

In the Enzygnost HBsAg micro "sandwich" assay (commercially available from Behring), wells were coated with anti-HBs. Serum plasma or purified protein and appropriate controls were added to the wells and incubated. After washing, peroxidase-labelled antibodies to HBsAg were reacted with the remaining antigenic determinants. The unbound enzyme-linked antibodies are removed by washing and the enzyme activity on the solid phase is determined. The enzymatically catalyzed reaction of hydrogen peroxide and chromogen was stopped by adding diluted sulfuric acid. The colour intensity was proportional to the HBsAg concentration of the sample and was obtained by photometric comparison of the colour intensity of the unknown samples with the colour intensities of the accompanying negative and positive control sera.

EXAMPLE 3

Preparation of a Construct of the Present Invention Containing the Methallothionein Promoter 1) Isolation of the MI Promoter The plasmid pBPV-342-12 (commercially available from ATCC) was digested with the endonucleases BglII and BamHI. Three DNA molecules were generated. The fragment of interest contains the methallothionein promoter and a pBR32Z sequence comprising 4.5 kb and is easily detectable from the other fragments (2.0 kb and 7.6 kb).

The reaction was performed in a total volume of 200 ul of reaction buffer at a final concentration of 0.5 ug/ul DNA including 100 units of each restriction enzyme. The completion of the digestion was checked after incubation at 37° C. for three hours by agarose gel electrophoresis at a 0.8% agarose gel. The reaction was stopped by adding 4 ul 0.5 M EDTA.

The 4.5 kb fragment was separated from the other fragments by preparative 1.2% agarose gel electrophoresis. The DNA was eluted from the agarose gel on DE-81 whatman filter paper from which the DNA was removed in a high salt buffer. The DNA was purified by a phenol/chloroform extraction and two ethanol precipitations.

2) Ligation of the 2.3 kb MBV BglII-BglII Fragment

A 2.3 kb BglII-BglII fragment containing the HBV pre-$S_1$,pre-$S_2$ and S coding regions was isolated from HBV-containing DNA. The 2–3 kb fragment was ligated together with the 4.5 kb fragment (obtained as described in C1) containing the methallothionein promoter.

2 ul of the 2.3 kb fragment were mixed with 3 ul of the 4.5 kb fragment and ligated together in a total volume of 10 ul ligation buffer, containing 2 unit $T_4$-DNA ligase and 2 mM ATP at 14° C. overnight.

The ligation mixture was added to 150 ul competent bacterial cell suspension for DNA up-take. After the DNA up-date the bacterial cells were spread on LB agar plate containing 50 ug/ml ampicillin at volumes of 50 to 300 ul cell suspension per plate. The agar plates were incubated at 37° C. overnight. Single isolated bacterial colonies were screened for the presence of a plasmid containing the desired fragments.

3) Screening for Desired Plasmid Containing Bacterial Colonies.

Single colonies were picked with a toothpick and transferred to a LB-ampicillin media containing tube (5 ml). The tubes were incubated overnight at 37° C. by shaking rapidly. A mini-plasmid preparation of each grown bacterial suspension was made. The different resulting DNAs were proved by digestion with the restriction endonuclease EcoRI. Two molecules were expected, a 2.2 kb fragment and a 4.6 kb fragment. The digestion was analysed by agarose gel electrophoresis. Plasmid DNA was isolated from the bacterial cells.

4) Conversion of a Part of the HBV-gene Sequence.

The plasmid resulting from (3) above was digested with the endonucleases BglII and XbaI. Two molecules were expected. one 550 bp fragment and one 6.250 kb fragment which was isolated after agarose gel electrophoresis.

The 6.250 kb fragment was ligated together with oligomecleotide No.55 from Table I. The ligation mixture was added to 150 ul competent bacterial cell suspension for DNA up-take. Single isolated bacterial colonies were screened for the presence of the desired plasmid. The new plasmid was proved by a digestion with the endonucleases EcoRI and BglII. Two molecules were expected, one 1.9 kb and one 4.450 kb.

5) Insertion of a Neomycin Selection Marker.

The plasmid resulting from (4) above was linearized by digestion with the restriction enzyme EcoRI. The reaction was performed in a total volume of 50 ul and a final concentration of 1 ug/ul plasmid DNA. 50 units of ECoRI were added and the digestion was proved after incubation at 37° C. for three hours by agarose gel electrophoresis. The reaction was stopped by adding 1 ul of 0.5 M EDTA and the DNA was precipitated with a final concentration of 0.3 M sodium acetate and 3–4 volumes of ethanol at –80° C. for 30 minutes. The precipitated DNA was dissolved in 50 ul distilled water.

2 ul of the linearized plasmid were mixed with 3 ul of the DNA fragment containing the methallothionein promoter and the neomycin selection gene [isolated from the plasmid pMT-neo-E (available from ATCC) by digestion with the endonuclease EcoRI as a 4kb fragment], and ligated together. Single bacterial colonies were screened for the presence of the desired plasmid.

6) Additional of the dhfr Amplification Gene dhfr

The plasmid pdhfr3.2 (available from ATCC) was digested with the restriction endonuclease HindIII. Two molecules were generated, one of 3,000 bp containing the dhfr gene sequence and one of 3,400 bp. The 3,000 bp fragment was isolated and ligated into the plasmid resulting from (5) above which was previously opened by digestion with HindIII. The resulting plasmid is represented by FIG. 1B.

EXAMPLE 4

1) Isolation of a Fragment Containing the U2 Promoter Sequence

The plasmid pUC-8-42 (available from Exogene ) was digested with the restriction endonucleases EcoRI and ApaI. Two DNA molecules were generated. The fragment of interest contains the U2-promoter comprising 340 bp and is easily detectable from the other fragment (3160 bp). The digestion was performed in a total volume of 200 ul of reaction buffer at a final concentration of 0.5 ug/ul DNA including 100 Units of each restriction enzyme. The completion of the digest was checked after incubation a 37° C. for three hours by agarose gel electrophoresis in a 0.7% agarose gel. The reaction was stopped by adding 4 ul 0.5 M EDTA. The 340 bp fragment was separated from the plasmid DNA by preparative 1.2% agarose gel electrophoresis. The DNA was eluted from the agarose gel on DE-81 Whatman filter paper from which the DNA was removed in a high salt buffer. The DNA was purified by a phenol/chloroform extraction and two ethanol precipitations.

2) Insertion of the Fragment Containing the Promoter Sequence into a Polylinker Plasmid The plasmid pSP165 (commercially available from Promega Biotec) containing a polylinker sequence (containing the following restriction sites: EcoRI, SacI, SmaI, AvaI, BamHI, BglII, SalI, PstI, HindIII) was linearized with the restriction enzyme EcoRI. The reaction was performed in a total volume of 50 ul and a final concentration of 1 ug/ul plasmid DNA. 50 Units of EcoRI were added an the digestion was proved after incubation at 37° C. for three hours by agarose gel electrophores. The reaction was stopped by adding 1 ul of 0.5 M EDTA and the DNA was precipitated with a final concentration of 0.3 M sidium acetate and 3–4 volumes of ethanol at –80° C. for 30 minutes. The precipitated DNA was dissolved in 50 ul distilled water.

2 ul of plasmid DNA were mixed with 10 ul of the fragment DNA containing the V2 promoter sequence, and ligated together in a total volume of 25 ul of ligation buffer containing 2 units T4-DNA ligase and mM ATP at 14° C. overnight. Thereafter the DNA was purified by phenol/chloroform extractions followed by two ethanol precipitations and dissolved in 10 ul distilled water. The resulting sticky ends of EcoRI and ApaI had to be converted into blunt ends and ligated. The blunt ends were converted by a removing reaction with the Mung bean nuclease as follows: to 25 ul DNA (1 ug/ul concentration) reaction buffer, 20 units of enzyme and a final concentration of 1% glycerol to the reaction volume of 35 ul were added. After an incubation for 30 minutes at 30° C. the DNA was purified by phenol/chloroform extractions followed by two ethanol precipitations. The DNA was dissolved again in 5 ul distilled water. The resulting blunt ends were ligated together in 15 ul reaction volume containing 10× more T4 ligase then used above and 2 mM ATP at 14° C. overnight.

The ligation mixture was added to 150 ul competent bacterial cell suspension for DNA up-take. After the DNA up-take the bacterial cells were spread on LB agar plates containing 50 ug/ml ampicillin at volumes of 50 to 300 ul cell suspension per plate. The agar plates were incubated at 37° C. overnight. Single isolated bacterial colonies were screened for the presence of a plasmid containing the desired U2-promoter fragment.

3. Screening for Desired Plasmid Containing Bacterial Colonies

Single colonies were picked with a toothpick and transferred to a LB-ampicillin containing tube (5 ml). The tubes were incubated overnight at 37° C. by shaking rapidly. A mini plasmid preparation of each grown bacterial suspension was made. The different resulting plasnid was proved by digestion with both restriction endonucleases EcoRI and HindIII. Two molecules were found, a 400 bp fragment containing the U2 promoter sequence and the plasmid of 2,700 bp. The digestion was analysed by agarose gel electrophoresis. The resulting plasmid was isolated from the bacterial cells.

4) Insertion of the Neomycine Selection Marker

The plasmid pBPV-342-12 (commercially available from ATCC) was digested with the endonuclease EcoRI and BamHI. Two molecules were isolated, one containing the MT promoter together with the neomycin selection gene of 4,000 bp and the plasmid of 10,000 bp.

The plasmid resulting from (3) above was linearized with EcoRI and ligated together with the 4,000 bp fragment containing the MT-promoter together with the neomycin selection gene. The resulting sticky ends were also converted into blunt ends and ligated together as described above.

After bacterial transformation, colony selection and mini plasmid preparation, the resulting plasmids were analysed by a digestion with the restriction enzymes EcoRI and HindIII. Two DNA molecules were isolated, a 400 bp fragment and a 6,700 bp fragment.

5) Ligation of the BglII-BglII Fragment

The plasmid resulting from (4) above was linearized with BglII. The 2.3 kb-BglII-BglII fragment was ligated together with the linearized plasmid. Bacterial colonies were analysed to find the resulting plasmid. The plasmid-DNA was digested with EcoRI and two resulting fragments were obtained, a 700 bp fragment (containing the promoter and a part of the HBV-sequence) and a 8,700 bp fragment (containing the rest of the HBV-sequence, MT-neo and plasmid).

6) Alterations within the HBV-sequence

The plasmid resulting from (5) above was digested with the endonucleases BglII and MstII. Two molecules were generated, one of 300 bp containing part of the pre-S sequence and the other (9,100 bp) which was eluted as described above. This 9,100 bp fragment was ligated to another BglII/MstII 216 bp fragment (sequence formed in two steps (i.e., a separate transfection for each construct) or in a single step (i.e., one transfection using preparation of both constructs). Cotransfection was confirmed either by use of different selection markers on the two constructs or by detection of secretion of expression products of both constructs by immunoassay.

Alternatively, a sequence encoding the HBV peptide sequence of the present invention and a separate sequence encoding the entire S protein could be combined in a single construct.

EXAMPLE 7

General Procedures

General procedures useful in practicing the present invention may be found in (1) *Methods of Enzymology*, volume 152, "Guide to Molecular Cloning Techniques," ed. Borger 3nd Kimmel (Academic Press 1987), and (2) Maniatis et al., "Molecular Cloning: A Laboratory Manual," (Cold Spring Harber Laboratory 1982), both of which are incorporated herein in their antirety by reference. Specific techniques employed are described below.

1) Digestion with Endonucleases and Isolation of Fragments

The restriction endonucleases used were: BglII, BamHI, HindIII, EcoRI, XbaI, MstII, XhoI, Pf1MI, commercially available from Gibco/BRL with their respective restriction buffers (10=).

```
= AGATCTACAGCATGGGGCAGAATCTTTCCACCAGCAATCCTCTGGGATTCTTTCCCGACCA
  BglII    S1

CCAGTTGGATCCAGCCTTCAGAGCAAACACCGCAAATCCAGATTGGGACTTCAATCCCAA

CAAGGACACCTGGCCAGACGCCAACAAGGTAGGAGCTGGAGCATTCGGCCTGGGTTTCAC

CCCACCGCACGGAGGCCTTTTGGGGTGGAGCCCTCAGG)
                                MstII
``` coding for an altered pre-$S_1$ gene sequence.

The desired plasmid was digested with EcoRI and two resulting fragments were isolated, a 616 bp fragment and a 8,700 bp fragment.

EXAMPLE 5

Isolation of the H2K Promoter

The H2K promoter was isolated as an EcoRI/BglII fragment (2kb) from psp65H2 (available from Exogene).

Isolation of the egpt Selection Marker

The fragment containing the methallothionein promoter and the egpt-selection gene was isolated by digestion of the plasmid pMSG (available front Pharmacia) with the restriction enzyme EcoRI as a 3.6 kb fragment.

All other plasmid constructions were made in similar ways by combining fragments containing the necessary components and employing desired oligonucleotides and adapter sequences (where necessary).

EXAMPLE 6

Transfection of Mammalian Cells with Constructs of the Present Invention

In order to achieve secretion of substantial amounts of the HBV peptides encoded by constructs of the present invention, mammalian cells must be transfected with both the construct of the present invention and a construct which will express entire S protein. The cotransfection was per- Unless otherwire indicated, restriction digests were performed and fragments were isolated as follows. Reactions typically contained 1–5 ug DNA.

- distilled water was added to the DNA in an eppendorf tube to a final volume of 8 ul
- 1 ul of the appropriate 10×digestion buffer was added
- 1 ul (containing 5–10 U) restriction enzyme was added and mixed carefully
- the reaction tube was incubated for 1 hour at 37° C.
- digestion was stopped by adding 0.5 M EDTA (pH 8.0) to a final concentration of 10 mM
- if the DNA was analysed directly on a gel, 1 ul of gel-loading dye III (Maniatis) was added, mixed and the sample was loaded into the slots of a 0.8% agarose gel.

The agarose gel normally contains 0.8% agarose 1×running buffer (TBE, Maniatis). Where a fragment (about 100–1000 bp) was isolated from an agarose gel the agarose was increased to 1.2 to 1.4%.

2) Competent Bacterial Cells

From a dense overnight culture, 1 ml of the bacterial cell suspension was added to 100 ml fresh growth medium (L-broth). The cells were grown at 37° C. to a density of $OD_{600}=0.7$ which was reachad within 2 hours with vigorous shaking in a 500 ml Erlenmeyer flask. Growth was atopped by chilling the culture on ice for 10 minutes. From this culture, 3 ml were taken for harvesting the exponential bacterial cells at 3,000 rpm for 5 minutes. The cells were resuspended in 1.5 ml of 50 mM $CaCl_2$ in 10 mM Trio, pH 8.0, and incubated on ice for another 15 minutes. The cells were harvested once more by centrifugation at 3,000 rpm for 5 minutes and resuspended in 200 ul of 50 mM CaCl$_2$ in 10 mM Tris, pH 8.0, and used directly.

3) Transformation of Competent Bacterial Cells

The DNA to be transformed was suspended in 10 mM Tris, pH 7.5, 1 mM EDT 70 ul and added to the 200 ul bacterial cell suspension for DNA take-up. The mixture was incubated on ice for 30 minutes and then 1 ml L-broth was added. The mixture was incubated at 42° C. for 2 minutes and at 37° C. for 40 minutes. After the incubation, the cells were spread on agar plates containing 50 ug ampicillin/ml agar at volumes of 50–300 ul cell suspension per plate. The agar plates were incubated at 37° C. overnight. After this incubation period, single isolated bacterial colonies were formed.

4) Plasmid DNA Isolation 1 liter of plasmid-bearing cells was grown to 0.5 OD$_{600}$ in L-broth and amplified for 20 hours with 200 ug/ml chloramphenicol. The culture was then centrifuged at 4,000 rpm for 20 minutes in JA-10 rotor, 4° C. The pellet was resuspended in 18 ml cold 25% sucrose, 50 mM Tris, pH 8.0, transferred to a 250 ml Erlenmeyer flask and kept on ice. 6 ml 5 mg/ml lysozyme in 250 mM Tris, pH 8.0 was added and the mixture was left to stand 10–15 minutes. 6 ml 250 mm EDTA, pH 8.0, was added, mixed gently and incubated for 15 minutes on ice. 30 ml detergent (0.01% Triton X-100; 60 mM EDTA, pH 8.0; 50 mM Tris, pH 8.0) was added and the mixture was incubated for 30 minutes on ice. After incubation, the mixture was centrifuged at 25,000 rpm 90 minutes in SW28 rotor, 4° C.

Pronase was added to supernatant fluid to 250 ug/ml and incubated 30 minutes, 370° C. The solution was extracted with phenol once with ½ volume phenol equilibrated with 10 mM Tris, pH 8.0, 1 mM EDTA. The aqueous layer was removed. Sodium acetate was then added to a final concentration of 300 mM, followed by the addition of 3 volumes cold 100% ethanol and thorough mixing. The mixture was stored at −20° C. overnight.

The mixture was thawed and centrifuged. The pellet was resuspended in 6 ml 10 mM Tris, 10 mM EDTA, pH 8.0. 9.4 g CsCl and 0.65 ml of 6 mg/ml ethidium bromide were added and the volume was brought up to 10 ml with sterile double-distilled water. The 10 ml aliqnots were put into Beckman heat-sealable gradient tubes and centrifuged, 50,000 rpm, 48 hours in Ti70.1 Beckman rotor.

Plasmid bands were visualized with UV and removed with syringe and 18 gauge needle by piercing the side of the tube. Ethidium bromide was removed from the plasmid fractions by 3 successive extractions with equal volumes of isobutanol. Fractions were then (1) dialyzed against one 2-liter lot of 10 mM Tris, pH 7.4, 1 mM EDTA, pH 7.5, 5 mM NaCl for 2 hours or more at 4° C.; and (2) phenol extracted once with ⅓ volume phenol equilibrated as above. Sodium acetate was then added to a final concentration of 300 mM, followed by addition of two volumes of 100% ethanol. Precipitate formed at −20° C. overnight, or at −70° C. for 30 minutes.

5) Mini-Plasmid Preparation 1 ml of an overnight bacteria culture was put into an eppendorf tube and centrifugated for 20 minutes. The supernatant was removed. 100 ul of 50 mM glucose, 25 mM Tris (pH 8.0), 10 mM EDTA (pH 8.0) was added to the pellet, mixed by vortex and incubated for 5 minutes at room temperature. 200 ul of 0.2 N NaOH, 1% SDS was added, mixed by vortex and incubated for 5 minutes on ice. 150 ul 3 M Sodium acetate (pH 4.8) was added, mixed by vortex and incubated for 5 minutes on ice. After centrifugation for 5 minutes at 13,000 rpm the supernatant was decanted into a fresh appendorf tube. 3 volumes of 100% ethanol were supplemented, mixed well and incubated for 30 minutes at −80° C., then centrifuged for 10 minutes at 13,000 rpm. The ethanol was removed, the pellet washed with 70% ethanol, lyophilized and dissolved in 20 ul distilled water. 5 ul of this plasmid DNA solution were used directly for restriction analysis.

6) Nick Translation

Nick translation was performed according to Rigby et al., J. Mol. Biol., Vol. 113, pp. 237–251, 1977, which is incorporated herein by reference. The reaction mixture for $^{32}$P-labeling of DNA contained 0.5 ug of a HBV fragment, in a total volume of 30 ul with 50 mM Tris, pH 7.8, 5 mM MgCl$_2$, 10 mM mercaptoethanol, 0.1 mM dATP, 0.1 mM dGTP, 0.1 mM dTTP, 50 uCi $^{32}$P-dCTP, 10 units DNA polymerase I, 3 ul of a 2×10$^{-5}$ fold dilution of 1 mg/ml DNase I and is incubated for 90 minutes at 15° C., yielding 3×10$^6$ to 12×10$^6$ total cpm, i.e. 1×10$^7$ to 5×10$^7$ cpm/ug DNA.

7) Southern Blot Analysis

To characterize the organization within the host cell genome of the vectors of this invention, chromosomal DNA from cell lines producing particles of this invention-were isolated and digested with the appropriate restriction enzyme (s) and analysed by the method of Southern (J. Mol. Biol., Vol. 98, pp. 503–517, 1975), which is incorporated herein by reference, using a $^{32}$P-labeled DNA probe. Following digestion of the chromosomal DNA (20 ug) with the restriction enzyme BglII, the resulting fragments were separated by 0.7% agarose, gel electrophoresis. Thereafter, the DNA was denatured by exposing to 366 nm UV light for 10 minutes and by incubation in a solution of 0.5 M NaOH and 1 M NaCl for 45 minutes. The gels were neutralized by incubation in 0.5 M Tris, 1.5 M NaCl, pH 7.5 for 60 minutes. The DNA was transferred to a nitrocellulose filter by soaking in 3 M NaCl, 0.3 M Sodiumcitrate (20×SSC) for 20 hours through the gel by covering the top of the nitrocellulose filter with a staple of dry paper towals. The nitrocellulose filter was kept for 2 hours in a vacuum oven at 80° C. A radioactive DNA probe from the BglII fragment of the pHBV (2.3 kb) was prepared by nick translation.

For hybridization with the DNA probe, the nitrocellulose filter was sealed in a plastic bag containing 10 ml of prehybridization mixture: 50% formamide, 5×SSC, 50 mM Sodiumphosphate, pH 7.0, 5×Denhardt's solution, 250 ug/ml denatured salmon sperm DNA. The filter was incubated in this mixture for 4 hours at 45° C., after which the pre-hybridization mixture was replaced by the hybridization mixture: 50% formamide, 5×SSC, 20 ml Sodiumphosphate, pH 7.0, 1×Denhardt's solution, 100 ug/ml denatured salmon sperm DNA, 5×10$^5$ cmp/ml $^{32}$P-probe. The filter, after incubating in the hybridization mix for 18 hours at 45° C., was washed three times, 5 minutes each, in 0.1×SSC, 0.1% SDS at 50° C. The filter was dried at 60° C. for 10 minutes and exposed to two X-ray films (XAR-5, KODAK) between two intensifying screens and kept at −80° C. The first X-ray film is developed after 3 days' exposure; the second film after 7 days' exposure.

8) Preparation of Mammalian Cells and DNA Precipitate for Transfection

The recipient cells (C127 or CHO-cells available from ATCC) were seeded in normal growth medium (DMEM+ 10% Fetal Calf Serum,Glycose and Glutamin) into petri-dishes (1–2×10$^6$ cells per dish, ¢ 10 cm) at day 1. The next day the medium was removed (4 hours before the DNA precipitate was added onto the cells), and the cells were washed twice with 1×PBS. Then 8 ml DMEM without FCS were added. 4 hours later the DNA precipitate (prepared as described below) was added to the cells. Again after 4 hours the madium was removed, 3 ml of Glycerol-Mix (50 ml 2×TBS buffer, 30 ml glycerol, 120 ml distilled water) were added. The Glycerol-Mix was immediately removed after an incubation at 37° C. for 3 minutes and the cells were washed with 1×PBS. The calls were cultivated overnight with 8 ml of DMEM with 10% FCS.

After 48 hours, the cells were recovered from the dish by treating with Trypain-EDTA-Solution (0.025% Trypsin+1 mM EDTA). Afterwards, to remove the Trypsin-EDTA the cells were washed with 1×PBS, suspended in DMEM with 10% FCS and distributed into 24 costar-well-plates (cells from one dish into four 24-well-plates). When the cells had grown wall, selection medium was added (concentration 0.5–1mg/ml of neomycin,or xanthine: 250 μg/ml, hypoxanthine: 15 μg/ml (or adenine: 25 μg/ml), thymidine: 10 μg/ml,aminopterine 2 μg/ml mycophenolic acid: 25 μg/ml for eco-gpt, for example). The medium was changed every week. The first growing cell colonies were seen after 2 weeks.

To 10 ug of plasmid DNA and 20 ug of carrier-DNA (salmon-sperm DNA, calf-thymus DNA) TE-buffer (10 mM Trix-HCl, 1 mM EDTA, pH 7.05) was added to a final volume of 440 ul and mixed together with 60 ul 2 M $CaCl_2$. Then the same amount of 2×TBS (Hepes 50 mM, NaCl 280 mM, $Na_2HPO_4$ 1.5 mM, pH 7.05) was added and mixed well. The precipitation solution was incubated for 30 minutes at 37° C. and added directly to the cells which should be transfected.

EXAMPLE 8

Culturing of Transfected Cells to Secrete Protein

The selected cells are treated for further cultivation in normal growth medium as described in section 8.

EXAMPLE 9

F) Preparation of the Adjuvant of Purified Particles

To the desired concentration of antigen particles suspended in sterile saline, 1:10,000 volume Thimerosol, ⅟₁₀ volume of filter-sterilized 0.2 M Al K(S04)$_2$:12 H$_2$O were added. The pH was adjusted to 5.0 with sterile 1 N NaOH and the suspension seas stirred at room temperature for 3 hours. The alum-precipitated antigen was recovered by centrifugation for 10 minutes at 2,000 rpm, resuspended in sterile normal saline containing 1:10,000 Thimerosol and aliquotad under sterile conditions.

EXAMPLE 10

Figure 11:
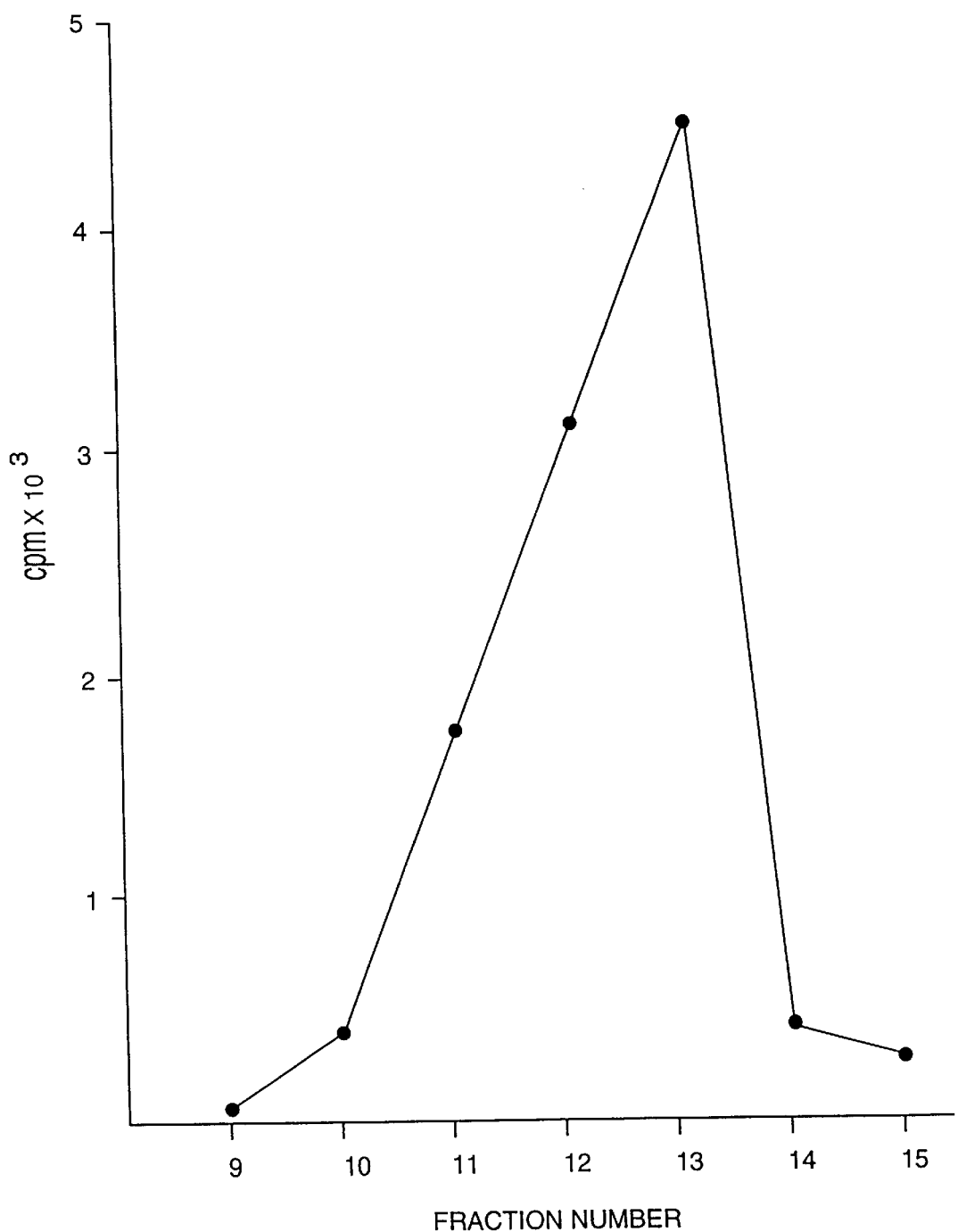
FIGS. 11 and 12 show the results obtained by caesium chloride sedimentation of immunogenic particles according to example 10.
Figure 12:
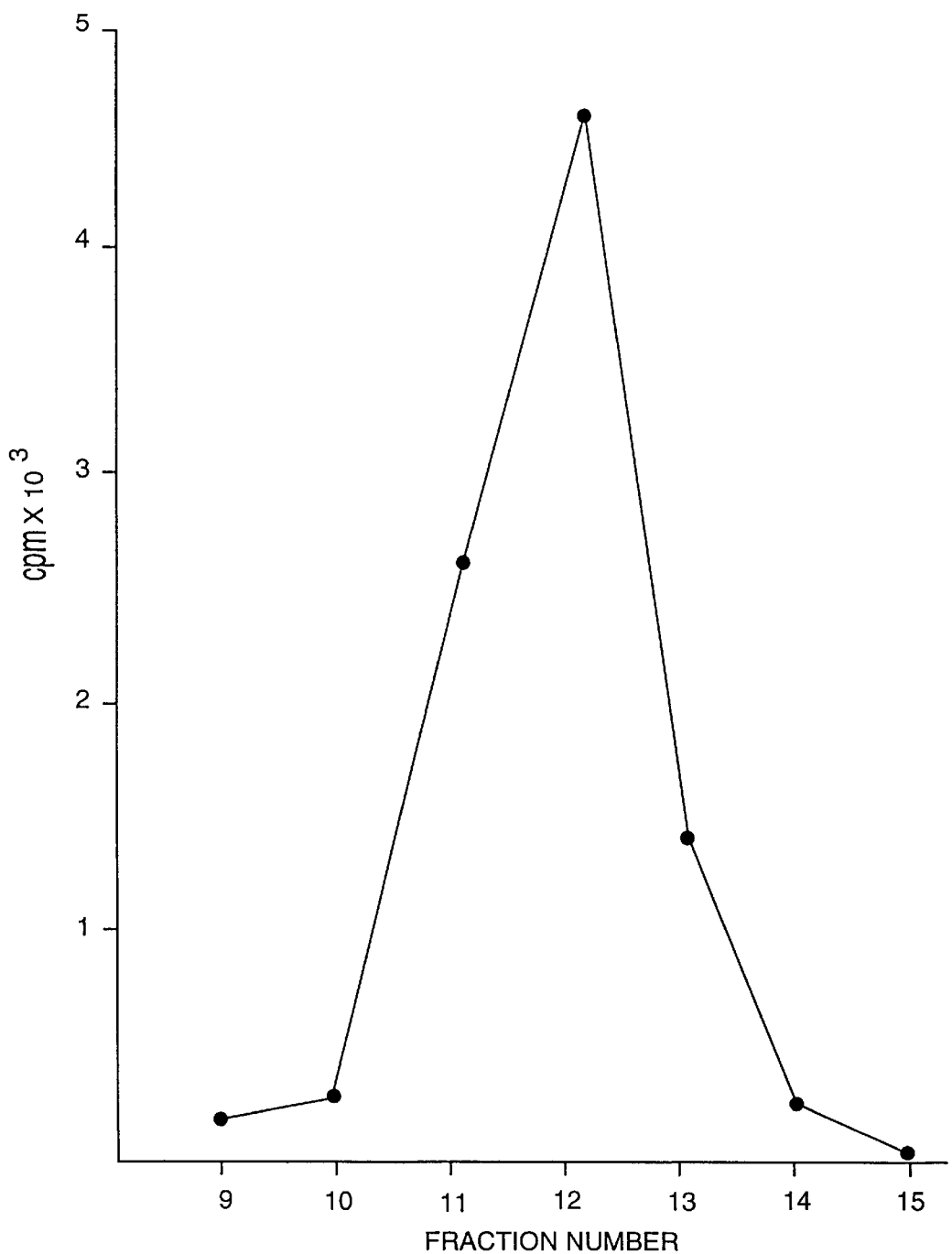

| Table III: | shows the ELISA data of the purified HBs antigen particle produced from any HBV sequence construct of the present invention including the pre-S$_1$ region with total deletion of pre-S$_2$ and deletions upstream of the pre-S$_2$ ATG and the S region with deletion of the S ATG and downstream the S ATG through the XBaI site (e.g. the construct of FIG. I-1) with the anti-pre-S$_1$ monoclonal antibody MA 18/7. The fractions 9–15 (FIG. XI) were pooled after CsCl sedimentation. |
|---|---|
| Table IV: | shows the ELISA data of the purified HBS antigen particle produced from any HBV sequence construct of the present invention including the pre-S$_1$ region with total deletion of pre-S$_2$ and deletions upstream of the pre-S$_2$ ATG and the S region with deletion of the S ATG and downstream the S ATG through the XBaI site (e.g., the construct of FIG. 1A with the anti-pre-S$_2$ monoclonal antibody MQ 19/10. The fractions 9–15 (FIG. 11) were pooled after CsCl sedimentation. |
| Table V: | shows the ELISA data of the purified HBs antigen particle produced from an HBV sequence construct of the present invention including the pre-S$_2$ region with none of the pre-S$_1$ region and deletions upstream of the S ATG and downstream of the S ATG through the XBaI site, and the S region with deletion of the S ATG (e.g. the construct of FIG. 2A) with the anti-pre-S$_1$ monoclonal antibody MA 18/7. The fractions 9–15 (FIG. 12) were pooled after CsCl sedimentation. |
| Table VI: | shows the ELISA data of the purified HBS antigen particle produced from on HBV sequence construct of the present invention including the pre-S$_2$ region with none of the pre-S$_1$ region and deletions upstream of the S ATG and downstream of the S ATG through the XBaI site, and the S region with deletion of the S ATG (e.g. the construct of FIG. 2A) with the anti-pre-S$_2$ monoclonal antibody MQ 19/10. The fractions 9–15 (FIG. 12) were pooled after CsCl sedimentation. |

TABLE III

| CsCl-gradient | ELISA Measurement Monoclonal Antibody MA 18/7 |
|---|---|
| Fraction No. 9–15 (pooled) | $E_{492}$ = 0.839 |

TABLE IV

| CsCl-gradient | ELISA Measurement Monoclonal Antibody MQ 19/10 |
|---|---|
| Fraction No. 9–15 (pooled) | $E_{492}$ = 0.000 |

TABLE V

| CsCl-gradient | ELISA Measurement Monoclonal Antibody MA 18/7 |
|---|---|
| Fraction No. 9–15 (pooled) | $E_{492}$ = 0.000 |

TABLE VI

| CsCl-gradient | ELISA Measurement Monoclonal Antibody MQ 19/10 |
|---|---|
| Fraction No. 9–15 (pooled) | $E_{492}$ = 1.028 |

Table VII: shows the ELISA data of the purified HBs antigen particle produced from any HBV sequence construct of the present invention including the pre-$S_1$ region with total deletion of pre-$S_2$ and deletions upstream of the pre-$S_2$ ATG and the S region with deletion of the S ATG (e.g., the construct of FIG. 6B) with the anti-pre-$S_1$ monoclonal antibody MA 18/7. The fractions 9–15 (FIG. 11) were pooled after CsCl sedimentation.

Table VIII: shows the ELISA data of the purified HBs antigen particle produced from any HBV sequence construct of the present invention including the pre-$S_1$ region with deletions upstream of the pre-$S_2$ ATG with deletion of the S ATG (e g., the construct of FIG. 6B) with the anti-pre-$S_2$ monoclonal antibody MQ 19/10. The fractions 9–15 (FIG. 11) were pooled after CsCl sedimentation.

Table IX: shows the ELISA data of the purified HBs antigen particle produced from an HBV sequence construct of the present invention including the pre-$S_2$ region with none of the pre-$S_1$ region and deletions upstream of the S ATG and the S region with deletion of the S ATG (e.g., the construct of FIG. 7B) with the anti-pre-$S_1$ monoclonal antibody MA 18/7. The fractions 9–15 (FIG. XII) were pooled after CsCl sedimentation.

Table X: shows the ELISA data of the purified HBs antigen particle produced from an HBV sequence construct of the present invention including the pre-$S_2$ region with deletions upstream of the S ATG with deletion of the S ATG (e.g., the construct of FIG. 7B) with the anti-pre-$S_2$ monoclonal antibody MQ 19/10. The fractions 9–15 (FIG. 12) were pooled after CsCl sedimentation.

TABLE VII

| CsCl-gradient | ELISA Measurement Monoclonal Antibody MA 18/7 |
|---|---|
| Fraction No. 9–15 (pooled) | $E_{492} = 1.273$ |

TABLE VIII

| CsCl-gradient | ELISA Measurement Monoclonal Antibody MQ 19/10 |
|---|---|
| Fraction No. 9–15 (pooled) | $E_{492} = 0.000$ |

TABLE IX

| CsCl-gradient | ELISA Measurement Monoclonal Antibody MA 18/7 |
|---|---|
| Fraction No. 9–15 (pooled) | $E_{492} = 0.000$ |

TABLE X

| CsCl-gradient | ELISA Measurement Monoclonal Antibody MQ 19/10 |
|---|---|
| Fraction No. 9–15 (pooled) | $E_{492} = 0.985$ |

Figure 13:
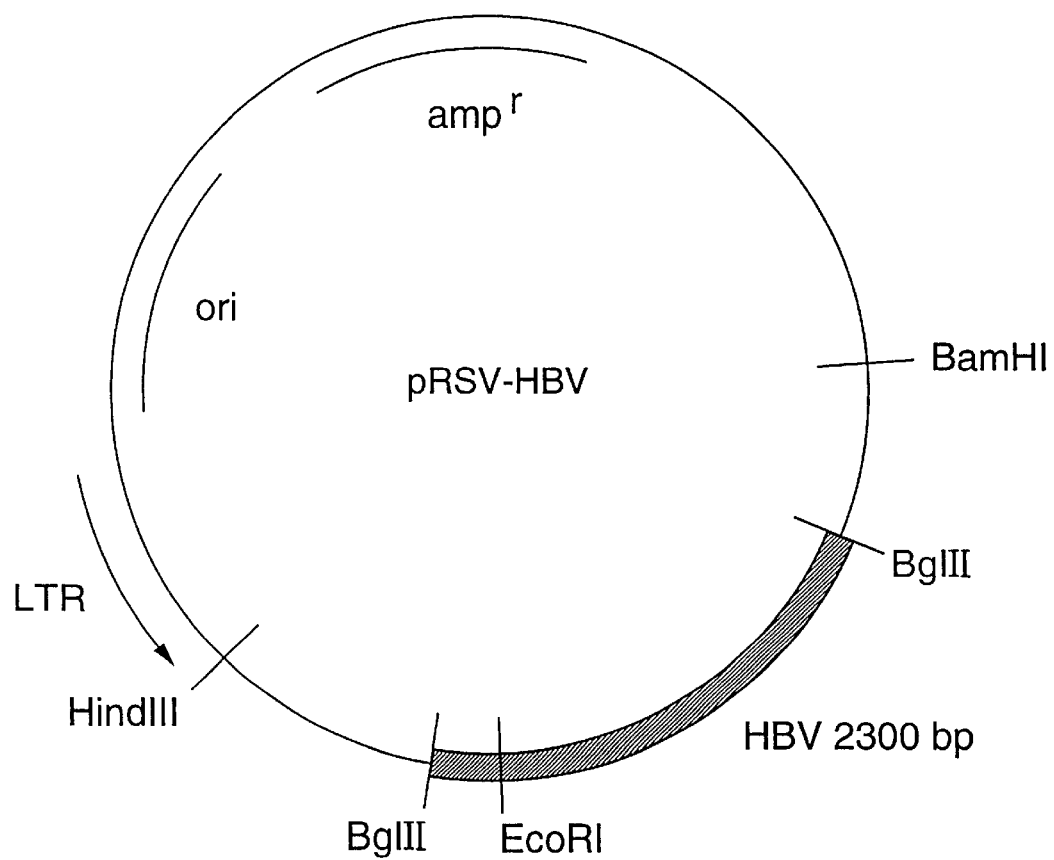
FIG. 13 shows a prior art construct shown in Table XI.
Figure 14:
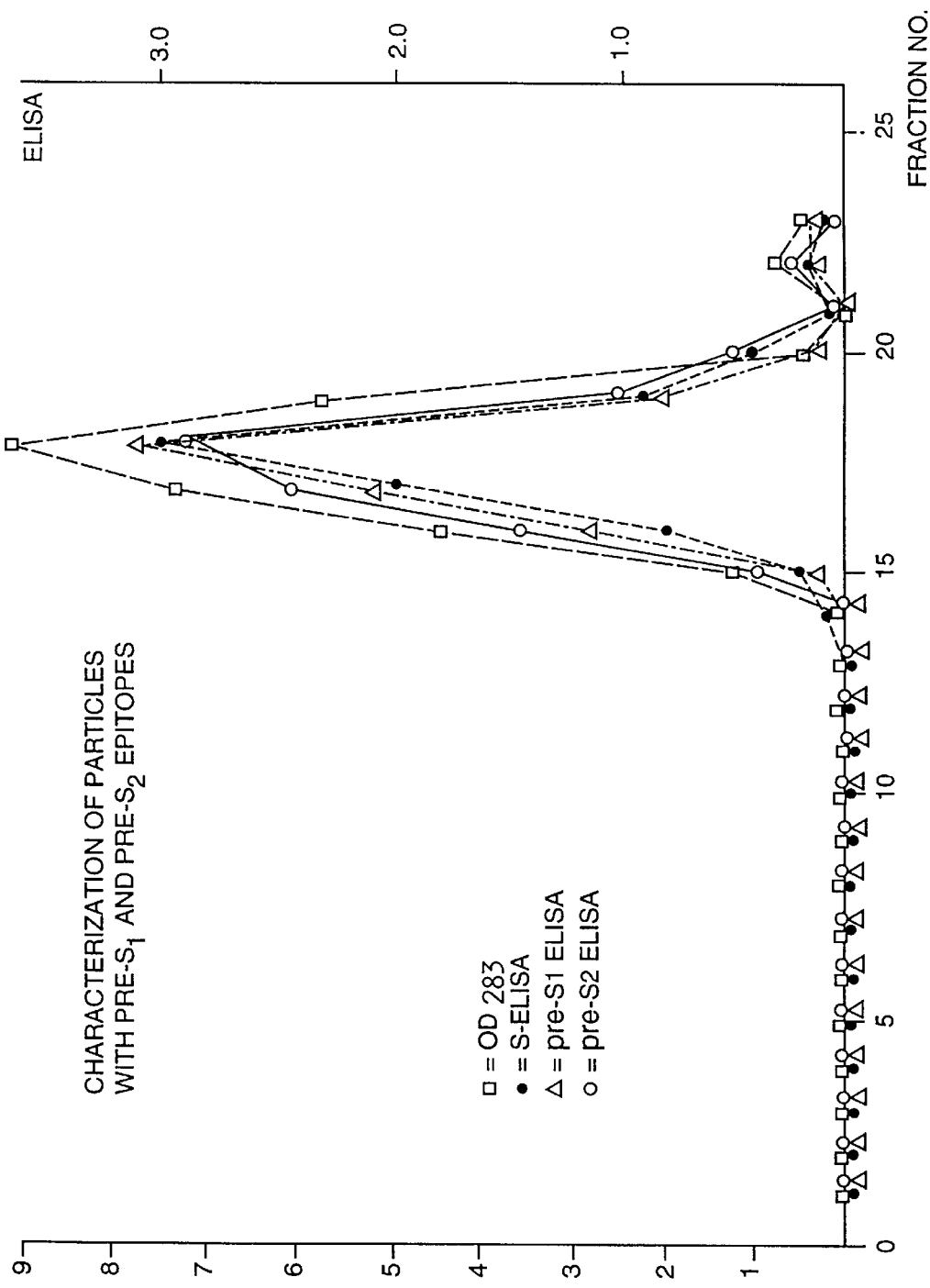
FIG. 14 shows the characterisation of particles derived from a construct according to a further embodiment of the present invention.

Table XI: shows the ELISA data of purified HBs antigen particles produced by construct including the entire pre-$S_1$ - pre-$S_2$ - S region under control of the LTR region of rous sarcoma virus after stimulation with stimulating substances (e.g. PMA) and the additional cotransfection with S (FIG. 13).

TABLE XI

| CsCl-gradient | ELISA Measurement Monoclonal Antibody MA 18/7 |
|---|---|
| Fraction No. 9–15 (pooled) | $E_{492} = 0.125$ |

FIG. XIV: shows the characterisation of the particles derived from gene constructs according to table III (FIG. 1A) and table V (FIG. 2A) cotransfected in C127 after purification in the CsCl gradient. The fraction collected had a smaller volume.

Table XII: shows the serotyping of particles according to FIG. 1A having the S sequence done in the Pettenkofer Institute.

TABLE XII

Results:
adw/ayw: positive

From the foregoing, it will be obvious to those skilled in the art that various modifications in the above-described compositions and methods can be made without departing from the spirit and scope of the invention. Accordingly, the invention may be embodied in other specific forms without departing from the spirit or essential characteristics thereof. Present embodiments, therefore, are to be considered in all respects as illustrative and not restrictive, the scope of the invention being indicated by the appended claims rather than by the foregoing description, and all changes which come within the meaning and range of equivalency of the claims are therefore intended to be embraced therein.

What is claimed is:

1. A polypeptide, wherein the polypeptide is prepared by recombinant DNA processes from gene constructs in cultured host cells, and wherein the polypeptide comprises:
 a first amino acid sequence, wherein the first amino acid sequence exhibits the antigenicity of an HBV pre-S1 epitope; and
 a second amino acid sequence, wherein the second amino acid sequence comprises all or a portion of an HBV surface antigen peptide having the capacity to be assembled into particles; and wherein the polypeptide:

does not comprise the entire sequence of amino acids of an HBV pre-S1 peptide;

exhibits the antigenicity of the HBV pre-S1 epitope; and when produced from the gene constructs in the cultured host cells, retains the capacity of the second amino acid sequence to be assembled into particles.

2. A polypeptide, wherein the polypeptide is prepared by recombinant DNA processes from gene constructs in cultured host cells, and wherein the polypeptide comprises:

a first amino acid sequence, wherein the first amino acid sequence exhibits the antigenicity of an HBV pre-S1 epitope; and a second amino acid sequence, wherein the second amino acid sequence comprises all or a portion of an HBV surface antigen peptide having the capacity to be assembled into particles; and wherein the polypeptide:

does not comprise the entire sequence of amino acids of an HBV pre-S1 peptide;

does not comprise an amino acid sequence which exhibits the antigenicity of an HBV pre-S2 epitope;

exhibits the antigenicity of the HBV pre-S1 epitope; and when produced from the gene constructs in the cultured host cells, retains the capacity of the second amino acid sequence to be assembled into particles.

3. A polypeptide, wherein the polypeptide is prepared by recombinant DNA processes from gene constructs in cultured host cells, and wherein the polypeptide comprises:

a first amino acid sequence, wherein the first amino acid sequence exhibits the antigenicity of an HBV pre-S1 epitope; and a second amino acid sequence, wherein the second amino acid sequence comprises all or a portion of an HBV core antigen peptide having the capacity to be assembled into particles; and wherein the polypeptide:

does not comprise the entire sequence of amino acids of an HBV pre-S1 peptide;

exhibits the antigenicity of the HBV pre-S1 epitope; and when produced from the gene constructs in the cultured host cells, retains the capacity of the second amino acid sequence to be assembled into particles.

4. A polypeptide, wherein the polypeptide is prepared by recombinant DNA processes from gene constructs in cultured host cells, and wherein the polypeptide comprises:

a first amino acid sequence, wherein the first amino acid sequence exhibits the antigenicity of an HBV pre-S1 epitope; and a second amino acid sequence, wherein the second amino acid sequence comprises all or a portion of an HBV core antigen peptide having the capacity to be assembled into particles; and wherein the polypeptide:

does not comprise the entire sequence of amino acids of an HBV pre-S1 peptide;

does not comprise an amino acid sequence which exhibits the antigenicity of an HBV pre-S2 epitope; and exhibits the antigenicity of the HBV pre-S1 epitope; and when produced from the gene constructs in the cultured host cells, retains the capacity of the second amino acid sequence to be assembled into particles.

5. A particle comprising a polypeptide, wherein the polypeptide is prepared by recombinant DNA processes from gene constructs in cultured host cells, and wherein the polypeptide comprises:

a first amino acid sequence, wherein the first amino acid sequence exhibits the antigenicity of an HBV pre-S1 epitope; and a second amino acid sequence, wherein the second amino acid sequence comprises all or a portion of an HBV surface antigen peptide having the capacity to be assembled into particles; and wherein the polypeptide:

does not comprise the entire sequence of amino acids of an HBV pre-S1 peptide;

exhibits the antigenicity of the HBV pre-S1 epitope; and when produced from the gene constructs in the cultured host cells, retains the capacity of the second amino acid sequence to be assembled into particles.

6. A particle comprising a polypeptide, wherein the polypeptide is prepared by recombinant DNA processes from gene constructs in cultured host cells, and wherein the polypeptide comprises:

a first amino acid sequence, wherein the first amino acid sequence exhibits the antigenicity of an HBV pre-S1 epitope; and a second amino acid sequence, wherein the second amino acid sequence comprises all or a portion of an HBV surface antigen peptide having the capacity to be assembled into particles; and wherein the polypeptide:

does not comprise the entire sequence of amino acids of an HBV pre-S1 peptide;

does not comprise an amino acid sequence which exhibits the antigenicity of an HBV pre-S2 epitope;

exhibits the antigenicity of the HBV pre-S1 epitope; and when produced from the gene constructs in the cultured host cells, retains the capacity of the second amino acid sequence to be assembled into particles.

7. A particle comprising a polypeptide, wherein the polypeptide is prepared by recombinant DNA processes from gene constructs in cultured host cells, and wherein the polypeptide comprises:

a first amino acid sequence, wherein the first amino acid sequence exhibits the antigenicity of an HBV pre-S1 epitope; and a second amino acid sequence, wherein the second amino acid sequence comprises all or a portion of an HBV core antigen peptide having the capacity to be assembled into particles; and wherein the polypeptide:

does not comprise the entire sequence of amino acids of an HBV pre-S1 peptide;

exhibits the antigenicity of the HBV pre-S1 epitope; and when produced from the gene constructs in the cultured host cells, retains the capacity of the second amino acid sequence to be assembled into particles.

8. A particle comprising a polypeptide, wherein the polypeptide is prepared by recombinant DNA processes from gene constructs in cultured host cells, and wherein the polypeptide comprises:

a first amino acid sequence, wherein the first amino acid sequence exhibits the antigenicity of an HBV pre-S1 epitope; and a second amino acid sequence, wherein the second amino acid sequence comprises all or a portion of an HBV core antigen peptide having the capacity to be assembled into particles; and
wherein the polypeptide:
does not comprise the entire sequence of amino acids of an HBV pre-S1 peptide;
does not comprise an amino acid sequence which exhibits the antigenicity of an HBV pre-S2 epitope; and
exhibits the antigenicity of the HBV pre-S1 epitope; and
when produced from the gene constructs in the cultured host cells, retains the capacity of the second amino acid sequence to be assembled into particles.

9. A vaccine comprising a particle comprising a polypeptide, wherein the polypeptide is prepared by recombinant DNA processes from gene constructs in cultured host cells, and wherein the polypeptide comprises:
a first amino acid sequence, wherein the first amino acid sequence exhibits the antigenicity of an HBV pre-S1 epitope; and
a second amino acid sequence, wherein the second amino acid sequence comprises all or a portion of an HBV surface antigen peptide having the capacity to be assembled into particles; and wherein the polypeptide:
does not comprise the entire sequence of amino acids of an HBV pre-S1 peptide;
exhibits the antigenicity of the HBV pre-S1 epitope; and
when produced from the gene constructs in the cultured host cells, retains the capacity of the second amino acid sequence to be assembled into particles.

10. A vaccine comprising a particle comprising a polypeptide, wherein the polypeptide is prepared by recombinant DNA processes from gene constructs in cultured host cells, and wherein the polypeptide comprises:
a first amino acid sequence, wherein the first amino acid sequence exhibits the antigenicity of an HBV pre-S1 epitope; and
a second amino acid sequence, wherein the second amino acid sequence comprises all or a portion of an HBV surface antigen peptide having the capacity to be assembled into particles; and
wherein the polypeptide:
does not comprise the entire sequence of amino acids of an HBV pre-S1 peptide;
does not comprise an amino acid sequence which exhibits the antigenicity of an HBV pre-S2 epitope;
exhibits the antigenicity of the HBV pre-S1 epitope; and
when produced from the gene constructs in the cultured host cells, retains the capacity of the second amino acid sequence to be assembled into particles.

11. A vaccine comprising a particle comprising a polypeptide, wherein the polypeptide is prepared by recombinant DNA processes from gene constructs in cultured host cells, and wherein the polypeptide comprises:
a first amino acid sequence, wherein the first amino acid sequence exhibits the antigenicity of an HBV pre-S1 epitope; and
a second amino acid sequence, wherein the second amino acid sequence comprises all or a portion of an HBV core antigen peptide having the capacity to be assembled into particles; and
wherein the polypeptide:
does not comprise the entire sequence of amino acids of an HBV pre-S1 peptide;
exhibits the antigenicity of the HBV pre-S1 epitope; and
when produced from the gene constructs in the cultured host cells, retains the capacity of the second amino acid sequence to be assembled into particles.

12. A vaccine comprising a particle comprising a polypeptide, wherein the polypeptide is prepared by recombinant DNA processes from gene constructs in cultured host cells, and wherein the polypeptide comprises:
a first amino acid sequence, wherein the first amino acid sequence exhibits the antigenicity of an HBV pre-S1 epitope; and
a second amino acid sequence, wherein the second amino acid sequence comprises all or a portion of an HBV core antigen peptide having the capacity to be assembled into particles; and
wherein the polypeptide:
does not comprise the entire sequence of amino acids of an HBV pre-S1 peptide;
does not comprise an amino acid sequence which exhibits the antigenicity of an HBV pre-S2 epitope; and
exhibits the antigenicity of the HBV pre-S1 epitope; and
when produced from the gene constructs in the cultured host cells, retains the capacity of the second amino acid sequence to be assembled into particles.

13. A recombinant DNA molecule comprising an expression control sequence operatively linked to first and second DNA sequences linked in frame, the first and second DNA sequences each encoding for respective discrete regions of a single polypeptide expressed by the recombinant DNA molecule, wherein:
the first DNA sequence comprises a nucleotide sequence encoding a first amino acid sequence, wherein the first amino acid sequence exhibits the antigenicity of an HBV pre-S1 epitope; and
the second DNA sequence comprises a nucleotide sequence encoding a second amino acid sequence, wherein the second amino acid sequence comprises all or a portion of an HBV surface antigen peptide having the capacity to be assembled into particles; and
wherein the polypeptide:
does not comprise the entire sequence of amino acids of an HBV pre-S1 peptide;
exhibits the antigenicity of the HBV pre-S1 epitope; and
when produced by the recombinant DNA molecule in cultured host cells, retains the capacity of the second amino acid sequence to be assembled into particles.

14. A recombinant DNA molecule comprising an expression control sequence operatively linked to first and second DNA sequences linked in frame, the first and second DNA sequences each encoding for respective discrete regions of a single polypeptide expressed by the recombinant DNA molecule, wherein:
the first DNA sequence comprises a nucleotide sequence encoding a first amino acid sequence, wherein the first amino acid sequence exhibits the antigenicity of an HBV pre-S1 epitope; and
the second DNA sequence comprises a nucleotide sequence encoding a second amino acid sequence, wherein the second amino acid sequence comprises all or a portion of an HBV surface antigen peptide having the capacity to be assembled into particles; and
wherein the polypeptide:
does not comprise the entire sequence of amino acids of an HBV pre-S1 peptide;
does not comprise an amino acid sequence which exhibits the antigenicity of an HBV pre-S2 epitope;
exhibits the antigenicity of the HBV pre-S1 epitope; and
when produced by the recombinant DNA molecule in cultured host cells, retains the capacity of the second amino acid sequence to be assembled into particles.

15. A recombinant DNA molecule comprising an expression control sequence operatively linked to first and second DNA sequences linked in frame, the first and second DNA sequences each encoding for respective discrete regions of a single polypeptide expressed by the recombinant DNA molecule, wherein:

the first DNA sequence comprises a nucleotide sequence encoding a first amino acid sequence, wherein the first amino acid sequence exhibits the antigenicity of an HBV pre-S1 epitope; and the second DNA sequence comprises a nucleotide sequence encoding a second amino acid sequence, wherein the second amino acid sequence comprises all or a portion of an HBV core antigen peptide having the capacity to be assembled into particles; and wherein the polypeptide:

does not comprise the entire sequence of amino acids of an HBV pre-S1 peptide;

exhibits the antigenicity of the HBV pre-S1 epitope; and when produced by the recombinant DNA molecule in cultured host cells, retains the capacity of the second amino acid sequence to be assembled into particles.

16. A recombinant DNA molecule comprising an expression control sequence operatively linked to first and second DNA sequences linked in frame, the first and second DNA sequences each encoding for respective discrete regions of a single polypeptide expressed by the recombinant DNA molecule, wherein:

the first DNA sequence comprises a nucleotide sequence encoding a first amino acid sequence, wherein the first amino acid sequence exhibits the antigenicity of an HBV pre-S1 epitope; and the second DNA sequence comprises a nucleotide sequence encoding a second amino acid sequence, wherein the second amino acid sequence comprises all or a portion of an HBV core antigen peptide having the capacity to be assembled into particles; and wherein the polypeptide:

does not comprise the entire sequence of amino acids of an HBV pre-S1 peptide;

does not comprise an amino acid sequence which exhibits the antigenicity of an HBV pre-S2 epitope;

exhibits the antigenicity of the HBV pre-S1 epitope; and when produced by the recombinant DNA molecule in cultured host cells, retains the capacity of the second amino acid sequence to be assembled into particles.

* * * * *